United States Patent
Barrow et al.

(10) Patent No.: US 8,501,773 B2
(45) Date of Patent: Aug. 6, 2013

(54) 4-FLUORO-PIPERIDINE T-TYPE CALCIUM CHANNEL ANTAGONISTS

(75) Inventors: James C. Barrow, Harleysville, PA (US); Craig W. Lindsley, Brentwood, TN (US); William D. Shipe, Chalfont, PA (US); Zhiqiang Yang, Schwenksville, PA (US); David Wisnoski, Quakertown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 924 days.

(21) Appl. No.: 11/922,399

(22) PCT Filed: Jun. 28, 2006

(86) PCT No.: PCT/US2006/025496
§ 371 (c)(1),
(2), (4) Date: Dec. 17, 2007

(87) PCT Pub. No.: WO2007/002884
PCT Pub. Date: Jan. 4, 2007

(65) Prior Publication Data
US 2010/0216841 A1 Aug. 26, 2010

Related U.S. Application Data

(60) Provisional application No. 60/695,073, filed on Jun. 29, 2005.

(51) Int. Cl.
| | | |
|---|---|---|
| *A01N 43/42* | (2006.01) |
| *A01N 43/40* | (2006.01) |
| *A61K 31/47* | (2006.01) |
| *A61K 31/445* | (2006.01) |
| *C07D 211/00* | (2006.01) |
| *C07D 295/00* | (2006.01) |
| *C07D 211/08* | (2006.01) |
| *C07D 401/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |
| *C07D 421/00* | (2006.01) |

(52) U.S. Cl.
USPC .......... 514/314; 514/317; 546/184; 546/192

(58) Field of Classification Search
USPC ................ 514/314, 317; 546/184, 192
See application file for complete search history.

(56) References Cited

U.S. PATENT DOCUMENTS

| | | | |
|---|---|---|---|
| 6,538,002 B1 * | 3/2003 | Finke et al. ................ 514/278 |
| 6,872,741 B2 | 3/2005 | Choi et al. |
| 7,071,213 B2 * | 7/2006 | Friary et al. ............... 514/323 |
| 7,589,109 B2 * | 9/2009 | Uchida et al. ............. 514/323 |
| 7,595,329 B2 * | 9/2009 | Ando et al. ................ 514/322 |
| 2004/0220206 A1 | 11/2004 | Smallheer et al. |
| 2005/0049287 A1 | 3/2005 | Ehring et al. |
| 2005/0054695 A1 | 3/2005 | Ehring et al. |
| 2005/0130966 A1 | 6/2005 | Choi et al. |

FOREIGN PATENT DOCUMENTS
WO WO 2007/002361 1/2007

OTHER PUBLICATIONS

Mahon et al. "Calcium channel blockers in cardiac failure" Progress in cardiovascular disease, Nov.-Dec. 1998, vol. 41(3), pp. 191-206 (abstract provided).*
Shipe et al., "Design, Synthesis, and Evaluation of a Novel 4-Aminomethyl-4-Fluoropiperidine as a T-Type Ca2 Channel Antagonist", J. Med. Chem, Jun. 2008, vol. 51, pp. 3692-3695.
Yang et al., "Discovery of 1,4-Substituted Piperidines as Potent and Selective Inhibitors of T-Type Calcium Channels", J. Med. Chem, Sep. 2008, vol. 51, pp. 6471-6477.

* cited by examiner

*Primary Examiner* — Kendra D Carter
(74) *Attorney, Agent, or Firm* — J. Eric Thies; Gerard M. Devlin

(57) ABSTRACT

The present invention is directed to 4-fluoro-piperidine compounds which are antagonists of T-type calcium channels, and which are useful in the treatment or prevention of neurological and psychiatric disorders and diseases in which T-type calcium channels are involved. The invention is also directed to pharmaceutical compositions comprising these compounds and the use of these compounds and compositions in the prevention or treatment of such diseases in which T-type calcium channels are involved.

10 Claims, No Drawings

4-FLUORO-PIPERIDINE T-TYPE CALCIUM CHANNEL ANTAGONISTS

CROSS REFERENCE TO RELATED APPLICATIONS

This application is a U.S. National Phase application under 35 U.S.C. §371 of PCT Application No. PCT/US2006/025496, filed Jun.28, 2006, which claims priority under 35 U.S.C. §119 from US application No. 60/695,073, filed Jun. 29, 2005.

BACKGROUND OF THE INVENTION

Plasma membrane calcium channels are members of a diverse superfamily of voltage gated channel proteins. Calcium channels are membrane-spanning, multi-subunit proteins that allow controlled entry of Ca2+ ions into cells from the extracellular fluid. Excitable cells throughout the animal kingdom, and at least some bacterial, fungal and plant cells, possess one or more types of calcium channel. Nearly all "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels Multiple types of calcium channels have been identified in mammalian cells from various tissues, including skeletal muscle, cardiac muscle, lung, smooth muscle and brain. A major type of this family are the L-type calcium channels, whose function is inhibited by the familiar classes of calcium channel blockers (dihydropyridines such as nifedipine, phenylalkylamines such as verapamil, and benzothiazepines such as diltiazem). Additional classes of plasma membrane calcium channels are referred to as T, N, P, Q and R.

The "T-type" (or "low voltage-activated") calcium channels are so named because their openings are of briefer duration (T=transient) than the longer (L=long-lasting) openings of the L-type calcium channels. The L, N, P and Q-type channels activate at more positive potentials (high voltage activated) and display diverse kinetics and voltage-dependent properties. There are three subtypes of T-type calcium channels that have been molecularly, pharmacologically, and electrophysiologically identified from various warm blooded animals including rat [J. Biol. Chem. 276(6) 3999-4011 (2001); Eur Neurosci 11(12):4171-8 (1999); reviewed in Cell Mol Life Sci 56(7-8):660-9 (1999)]. These subtypes have been termed α1G, α1H, and α1I. The molecular properties of these channels demonstrate that the amino acid sequences are between 60-70% identical. The electrophysiological characterization of these individual subtypes has revealed differences in their voltage-dependent activation, inactivation, deactivation and steady-state inactivation levels and their selectivities to various ions such as barium (J. Biol. Chem. 276(6) 3999-4011 (2001)). Pharmacologically, these subtypes also have differing sensitivities to blockade by ionic nickel. These channel subtypes are also expressed in various forms due to their ability to undergo various splicing events during their assembly (J. Biol. Chem. 276(6) 3999-4011 (2001)).

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophreniac, cardiac arrhythmia, hypertension, pain, cancer, diabetes, infertility and sexual dysfunction (J Neuroscience, 14, 5485 (1994); Drugs Future 30(6), 573-580 (2005); EMBO J, 24, 315-324 (2005); Drug Discovery Today, 11, 5/6, 245-253 (2006)). The known therapeutic regimens for such treating such diseases and disorders suffer from numerous problems. Accordingly, a more physiological way to treat these diseases and disorders would be highly desirable.

SUMMARY OF THE INVENTION

The present invention is directed to 4-fluoro-piperidine compounds which are antagonists of T-type calcium channels, and which are useful in the treatment or prevention of neurological and psychiatric disorders and diseases in which T-type calcium channels are involved. The invention is also directed to pharmaceutical compositions comprising these compounds and the use of these compounds and compositions in the prevention or treatment of such diseases in which T-type calcium channels are involved.

DETAILED DESCRIPTION OF THE INVENTION

The present invention is directed to compounds of the formula I:

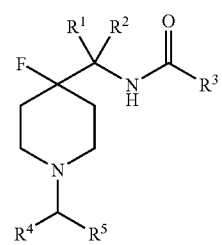

wherein:
$R^1$ and $R^2$ are independently selected from the group consisting of:
  (1) hydrogen, and
  (2) $C_{1-6}$alkyl, which is unsubstituted or substituted with halogen or hydroxyl,
  or $R^1$ and $R^2$ taken together form a $C_{3-6}$cycloalkyl ring, which is unsubstituted or substituted with $C_{1-6}$alkyl or halogen;
$R^3$ is selected from the group consisting of
  (1) phenyl, which is substituted with $R^{3a}$, $R^{3b}$, $R^{3c}$, $R^{3d}$ and $R^{3e}$,
  (2) $C_{1-8}$alkyl, which is unsubstituted or substituted with one or more substituents selected from:
    (a) phenyl, which is substituted with $R^{3a}$, $R^{3b}$, $R^{3c}$, $R^{3d}$ and $R^{3e}$,
    (b) halogen,
    (c) hydroxyl,
    (d) —O—$C_{1-6}$alkyl,
    (e) —$CO_2R^9$, where $R^9$ is independently selected from:
      (i) hydrogen,
      (ii) —$C_{1-6}$alkyl, which is unsubstituted or substituted with 1-6 fluoro,
      (iii) benzyl, and
      (iv) phenyl,
    (f) —$NR^{10}R^{11}$, wherein $R^{10}$ and $R^{11}$ are independently selected from hydrogen, —$C_{1-6}$alkyl, —$C_{1-6}$alkyl-$C_{3-6}$cycloalkyl and —$C_{1-6}$alkyl-O—$C_{1-6}$alkyl, or $R^{10}$ and $R^{11}$ together form a pyrrolidine, piperidine, oxazolidine or morpholine ring, which is unsubstituted or substituted with one or more halogen, $C_{1-6}$alkyl or halogen-substituted $C_{1-6}$alkyl,
(3) $C_{3-10}$ cycloalkyl, which is unsubstituted or substituted with one or more substituents selected from:
  (a) $C_{1-6}$alkyl,
  (b) phenyl, which is substituted with $R^{3a}$, $R^{3b}$, $R^{3c}$, $R^{3d}$ and $R^{3e}$,
  (c) halogen,
  (d) hydroxyl,
  (e) —O—$C_{1-6}$alkyl,
  (f) —$CO_2R^9$,
  (g) —$NR^{10}R^{11}$,
  (h) oxo,
(4) —$C_{1-6}$alkyl-($C_{3-10}$cycloalkyl), which is unsubstituted or substituted with one or more substituents selected from:
  (a) $C_{1-6}$alkyl,
  (b) phenyl, which is substituted with $R^{3a}$, $R^{3b}$, $R^{3c}$, $R^{3d}$ and $R^{3e}$,
  (c) halogen,
  (d) hydroxyl,
  (e) —O—$C_{1-6}$alkyl,
  (O—$CO_2R^9$,
  (g) —$NR^{10}R^{11}$,
  (h) oxo,
(5) heteroaryl, which is substituted with $R^{3a}$, $R^{3b}$, $R^{3c}$, $R^{3d}$ and $R^{3e}$, or oxo;
$R^{3a}$, $R^{3b}$, $R^{3c}$, $R^{3d}$ and $R^{3e}$ are independently selected from the group consisting of:
(1) hydrogen,
(2) halogen,
(3) hydroxyl,
(4) —$C_{1-6}$alkyl,
(5) —O—$C_{1-6}$alkyl,
(6) —$C_{1-6}$alkyl-O—$C_{1-6}$alkyl,
(6) —$CF_3$,
(7) —$OCF_3$,
(8) —$OCHF_2$,
(9) —$OCH_2F$,
(10) —$OCF_2CHF_2$,
(11) —CN, and
(12) —$NR^{10}R^{11}$;
(12) —$NO_2$,
$R^4$ and $R^5$ are independently selected from the group consisting of
(1) hydrogen,
(2) $C_{1-10}$alkyl or $C_{2-10}$alkenyl, which is unsubstituted or substituted with one or more substituents selected from:
  (a) phenyl, which is substituted with $R^{3a}$, $R^{3b}$, $R^{3c}$, $R^{3d}$ and $R^{3e}$,
  (b) halogen,
  (c) hydroxyl,
  (d) —O—$C_{1-6}$alkyl,
  (e) —$CO_2R^9$,
  (f) —$SO_2R^9$,
  (g) —$NR^{10}R^{11}$;
(3) $C_{3-10}$cycloalkyl or $C_{5-10}$cycloalkenyl, which is unsubstituted or substituted with one or more substituents selected from:
  (a) phenyl, which is substituted with $R^{3a}$, $R^{3b}$, $R^{3c}$, $R^{3d}$ and $R^{3e}$,
  (b) halogen,
  (c) hydroxyl,
  (d) —O—$C_{1-6}$alkyl,
  (e) —$CO_2R^9$,
  (f) —$NR^{10}R^{11}$;
(4) —$C_{1-10}$alkyl-($C_{3-10}$cycloalkyl) or —$C_{1-10}$alkyl-$C_{5-10}$cycloalkenyl;
(5) phenyl, which is substituted with $R^{3a}$, $R^{3b}$, $R^{3c}$, $R^{3d}$ and $R^{3e}$;
(6) heterocycle, which is substituted with $R^{3a}$, $R^{3b}$, $R^{3c}$, $R^{3d}$ and $R^{3e}$, or oxo,
(7) —CO—$C_{1-8}$alkyl, which is unsubstituted or substituted with one or more substituents selected from:
  (a) phenyl, which is substituted with $R^{3a}$, $R^{3b}$, $R^{3c}$, $R^{3d}$ and $R^{3e}$,
  (b) halogen,
  (c) hydroxyl,
  (d) —O—$C_{1-6}$alkyl,
  (e) —$CO_2R^9$,
  (f) —$NR^{10}R^{11}$;
(8) —$SO_2R^9$,
(9) —$CO_2R^9$, and
(10) —$CONR^{10}R^{11}$,
or $R^4$ and $R^5$ taken together form a $C_{3-6}$cycloalkyl ring, which is unsubstituted or substituted with $C_{1-6}$alkyl or halogen;
and N-oxides thereof, and pharmaceutically acceptable salts thereof and individual enantiomers and diastereomers thereof.

An embodiment of the present invention includes compounds of the
formula I, wherein:
$R^1$ and $R^2$ are independently selected from the group consisting of
(1) hydrogen, and
(2) $C_{1-6}$alkyl;
$R^3$ is selected from the group consisting of:
(1) phenyl, which is substituted with $R^{3a}$, $R^{3b}$ and $R^{3c}$,
(2) $C_{1-8}$alkyl, which is unsubstituted or substituted with phenyl, where the phenyl is substituted with $R^{3a}$, $R^{3b}$ and $R^{3c}$,
(3) $C_{3-10}$cycloalkyl, which is unsubstituted or substituted with phenyl, where the phenyl is substituted with $R^{3a}$, $R^{3b}$ and $R^{3c}$, and
(4) —$C_{1-6}$alkyl-($C_{3-10}$cycloalkyl), which is unsubstituted or substituted with phenyl, where the phenyl is substituted with $R^{3a}$, $R^{3b}$ and $R^{3c}$;
$R^{3a}$, $R^{3b}$ and $R^{3c}$ are independently selected from the group consisting of
(1) hydrogen,
(2) halogen,
(3) —$C_{1-6}$alkyl,
(4) —O—$C_{1-6}$alkyl,
(5) —$CF_3$,
(6) —$OCF_3$,
(7) —$OCHF_2$,
(8) —$OCH_2F$,
(9) —$OCF_2CHF_2$,
(10) —CN, and
(11) —$NR^{10}R^{11}$, wherein $R^{10}$ and $R^{11}$ are independently selected from hydrogen, —$C_{1-6}$alkyl, —$C_{1-6}$alkyl-$C_{3-6}$cycloalkyl and —$C_{1-6}$alkyl-O—$C_{1-6}$alkyl, or $R^{10}$ and $R^{11}$ together form a pyrrolidine, piperidine, oxazolidine or morpholine ring, which is unsubstituted or substituted with one or more halogen, $C_{1-6}$alkyl or halogen-substituted $C_{1-6}$alkyl;
$R^4$ and $R^5$ are independently selected from the group consisting of:
(1) hydrogen,
(2) $C_{1-8}$allyl, which is unsubstituted or substituted with hydroxy or phenyl, where the phenyl is substituted with $R^{3a}$, $R^{3b}$ and $R^{3c}$, (3) $C_{3-10}$ cycloalkyl or $C_{3-10}$cycloalkyl, which is unsubstituted or substituted with $C_{1-8}$alkyl or phenyl, where the phenyl is substituted with $R^{3a}$, $R^{3b}$ and $R^{3c}$,
(4) $C_{3-10}$cycloalkyloxy, which is unsubstituted or substituted with $C_{1-8}$alkyl or phenyl, where the phenyl is substituted with $R^{3a}$, $R^{3b}$ and $R^{3e}$, and
(5) —CO—$C_{1-8}$alkyl, and
(6) —CONR$^{10}$R$^{11}$;
and N-oxides thereof, and pharmaceutically acceptable salts thereof and individual enantiomers and diastereomers thereof.

An embodiment of the present invention includes compounds wherein $R^1$ is hydrogen and $R^2$ is hydrogen.

An embodiment of the present invention includes compounds wherein $R^1$ is methyl and $R^2$ is hydrogen.

An embodiment of the present invention includes compounds wherein $R^{3d}$ is hydrogen and $R^{3e}$ is hydrogen.

An embodiment of the present invention includes compounds wherein $R^3$ is phenyl which is substituted with $R^{3a}$, $R^{3b}$ and $R^{3c}$.

An embodiment of the present invention includes compounds wherein $R^{3a}$, $R^{3b}$ and $R^{3c}$ are independently selected from the group consisting of:
(1) hydrogen,
(2) fluoro,
(3) chloro,
(4) bromo,
(5) —CH$_3$,
(6) —C(CH$_3$)$_3$,
(7) —CF$_3$,
(8) —CN,
(9) —O—CH$_3$,
(10) —OCF$_3$,
(11) —OCHF$_2$,
(12) —OCH$_2$F,
(13) —OCF$_2$CHF$_2$, and
(14) —N(CH$_3$)$_2$.

An embodiment of the present invention includes compounds wherein $R^3$ is adamantyl.

An embodiment of the present invention includes compounds wherein $R^3$ is $C_{3-6}$cycloalkyl-phenyl, where the phenyl is substituted with $R^{3a}$, $R^{3b}$ and $R^{3c}$.

An embodiment of the present invention includes compounds wherein $R^3$ is cyclopropyl-phenyl, where the phenyl is substituted with $R^{3a}$, $R^{3b}$ and $R^{3c}$.

An embodiment of the present invention includes compounds wherein $R^3$ is cyclobutyl-phenyl, where the phenyl is substituted with $R^{3a}$, $R^{3b}$ and $R^{3c}$.

An embodiment of the present invention includes compounds wherein $R^3$ is cyclopentyl-phenyl, where the phenyl is substituted with $R^{3a}$, $R^{3b}$ and $R^{3c}$.

An embodiment of the present invention includes compounds wherein $R^3$ is cyclohexyl-phenyl, where the phenyl is substituted with $R^{3a}$, $R^{3b}$ and $R^{3c}$.

An embodiment of the present invention includes compounds wherein $R^4$ is hydrogen.

An embodiment of the present invention includes compounds wherein $R^4$ is hydrogen and $R^5$ is selected from the group consisting of:
(1) $C_{1-8}$alkyl, which is unsubstituted or substituted with hydroxy or phenyl, where the phenyl is substituted with $R^{3a}$, $R^{3b}$ and $R^{3c}$,
(2) $C_{1-10}$cycloalkyl, which is unsubstituted or substituted with $C_{1-8}$alkyl or phenyl, where the phenyl is substituted with $R^{3a}$, $R^{3b}$ and $R^{3c}$, and
(3) $C_{3-10}$cycloalkyloxy, which is unsubstituted or substituted with $C_{1-8}$alkyl or phenyl, where the phenyl is substituted with $R^{3a}$, $R^{3b}$ and $R^{3c}$, and
(4) —CO—$C_{1-8}$alkyl,
(5) —CONR$^{10}$R$^{11}$.

An embodiment of the present invention includes compounds wherein $R^4$ is hydrogen and $R^5$ is selected from the group consisting of
(1) $C_{1-8}$alkyl, which is unsubstituted or substituted with hydroxy,
(2) $C_{3-10}$cycloalkyl,
(3) —CO—$C_{1-8}$alkyl,
(4) —CO-pyrrolidine, —CO-piperidine, —CO-oxazolidine or —CO-morpholine, which is unsubstituted or substituted with one or more halogen, $C_{1-6}$alkyl or halogen-substituted $C_{1-6}$alkyl,
(5) —CONH—$C_{1-6}$alkyl, —CONH—$C_{1-6}$alkyl-$C_{3-6}$cycloalkyl or —CONH—$C_{1-6}$alkyl-O—$C_{1-6}$alkyl,
(6) tetrahydropyranyl, which is unsubstituted or substituted with one or more $C_{1-6}$alkyl, and
(7) tetrahydropyranyl, which is unsubstituted or substituted with one or more $C_{1-6}$alkyl.

An embodiment of the present invention includes compounds wherein $R^4$ is hydrogen and $R^5$ is selected from the group consisting of:
(1) —CH$_2$CH$_2$C(CH$_3$)$_3$,
(2) adamantyl,
(3) dimethyl-tetrahydropyranyl, and
(4) dimethyl-tetrahydropyranyl.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (termed "heteroaryl" herein) include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonizing T-type calcium channel activity in a patient such as a mammal in need of such inhibition comprising the administration of an effective amount of the compound. The present invention is directed to the use of the compounds disclosed herein as antagonists of T-type calcium channels activity. In addition to primates, especially humans, a variety of other mammals can be treated according to the method of the present invention.

The present invention is further directed to a method for the manufacture of a medicament for antagonizing T-type calcium channels activity or treating the disorders and diseases noted herein in humans and animals comprising combining a compound of the present invention with a pharmaceutical carrier or diluent.

The subject treated in the present methods is generally a mammal, preferably a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as T-type calcium channel antagonists may be readily determined without undue experimentation by methodology well known in the art, including the "FLIPR Ca$^{2+}$ Flux Assay" and the "T-type Calcium (Ca$^{2+}$) Antagonist Voltage-Clamp Assay" [described by Xia, et al., Assay and Drug Development Tech., 1(5), 637-645 (2003)]. In a typical experiment ion channel function from FMK 293 cells expressing the T-type channel alpha-1G, H, or I (CaV 3.1, 3.2, 3.3) is recorded to determine the activity of compounds in blocking the calcium current mediated by the T-type channel alpha-1G, H, or I (CaV 3.1, 3.2, 3.3). In this T-type calcium (Ca$^{2+}$) antagonist voltage-clamp assay calcium currents are elicited from the resting state of the human alpha-1G, H, or I (CaV 3.1, 3.2, 3.3) calcium channel as follows. Sequence information for T-type (Low-voltage activated) calcium channels are fully disclosed in e.g., U.S. Pat. No. 5,618,720, U.S. Pat. No. 5,686,241, U.S. Pat. No. 5,710,250,U.S. Pat. No. 5,726,035, U.S. Pat. No. 5,792,846, U.S. Pat. No. 5,846, 757, U.S. Pat. No. 5,851,824, U.S. Pat. No. 5,874,236, U.S. Pat. No. 5,876,958, U.S. Pat. No. 6,013,474, U.S. Pat. No. 6,057,114, U.S. Pat. No. 6,096,514, WO 99/28342, and J. Neuroscience, 19(6):1912-1921 (1999). Cells expressing the t-type channels were grown in H3D5 growth media which comprised DMEM, 6% bovine calf serum (HYCLONE), 30 micromolar Verapamil, 200 microgram/ml Hygromycin B, 1× Penicillin/Streptomycin. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05% Trypsin, 0.53 mM EDTA. The extracellular recording solution consists of (mM): 130 mM NaCl, 4 mM KCl, 1 mM MgCl2, 2 mM CaCl2, 10 mM HEPES, 30 Glucose, pH 7.4. The internal solution consists of (mM): 135 mM CsMeSO4, 1 MgCl2, 10 CsCl, 5 EGTA, 10 HEPES, pH 7.4, or 135 mM CsCl, 2 MgCl2, 3 MgATP, 2 Na2ATP, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell Ca2+ current response. Voltage protocols: (1) −80 mV holding potential every 20 seconds pulse to −20 mV for 40 msec duration; the effectiveness of the drug in inhibiting the current mediated by the channel is measured directly from measuring the reduction in peak current amplitude initiated by the voltage shift from −80 mV to −20 mV; (2). −100 mV holding potential every 15 seconds pulse to −20 mV for 40 msec duration; the effectiveness of the drug in inhibiting the current mediated by the channel is measured directly from measuring the reduction in peak current amplitude initiated by the shift in potential from −100 mV to −30 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control Ca2+ current during the depolarizing step to −20 mV is plotted as a function of compound concentration.

The intrinsic T-type calcium channel antagonist activity of a compound which may be used in the present invention may be determined by these assays.

In particular, the compounds of the following examples had activity in antagonizing the T-type calcium channel in the aforementioned assays, generally with an IC$_{50}$ of less than about 10 µM. Preferred compounds within the present invention had activity in antagonizing the T-type calcium channel in the aforementioned assays with an IC$_{50}$ of less than about 1 µM. Such a result is indicative of the intrinsic activity of the compounds in use as antagonists of T-type calcium channel activity.

With respect to other piperidinyl compounds disclosed in the art, the present compounds exhibit unexpected properties, such as with respect to increased selectivity with respect to other receptors and/or ion channels.

T-type calcium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium channels, including one or more of the following conditions or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute pain, chronic pain, severe pain, intractable pain, inflammatory pain, chronic inflammatory pain, neuropathic pain, chronic neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in preferred embodiments the present invention provides methods for: treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention.

The subject compounds are further useful in a method for the prevention, treatment, control, amelioration, or reducation of risk of the diseases, disorders and conditions noted herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of T-type calcium channel. The dosage range will generally be about 0.5 mg to 1.0 g. per patient per day which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Pharmaceutical compositions of the present invention may be provided in a solid dosage formulation preferably comprising about 0.5 mg to 500 mg active ingredient, more preferably comprising about 1 mg to 250 mg active ingredient. The pharmaceutical composition is preferably provided in a solid dosage formulation comprising about 1 mg, 5 mg, 10 mg, 25 mg, 50 mg, 100 mg, 200 mg or 250 mg active ingredient. For oral administration, the compositions are preferably provided in the form of tablets containing 1.0 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be employed in combination with an anti-seizure agent such as carbamazepine, clonazepam, divalproex, ethosuximide, felbamate, fosphenyloin, gabapentin, lamotrigine, levetiracetam, lorazepam, midazolam, oxcarbazepine, phenobarbital, phenyloin, primidone, tiagabine, topiramate, valproate, vigabatrin or zonisamide. In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the compounds of the present invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl) hydrochloride, COMT inhibitors such as entacapone, MOA-B inhibitors, antioxidants, A2a adenosine receptor antagonists, cholinergic agonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compounds of the present invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the compounds of the present invention may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. In another embodiment, the subject compound may be employed in combination with an L-type calcium channel antagonist, such as amlodipine.

In another embodiment, the compounds of the present invention may be administered in combination with compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, other T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the compounds of the present invention may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the present invention may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; $Et_3N$: triethylamine; DCM: dichloromethane; DCE: dichloroethane; BSA: bovine serum albumin; TFA: trifluoracetic acid; DMF: N,N-dimethylformamide; $SOCl_2$: thionyl chloride; CDI: carbonyl diimidazole; rt: room temperature; HPLC: high performance liquid chromatography. The compounds of the present invention can be prepared in a variety of fashions.

SCHEME 1

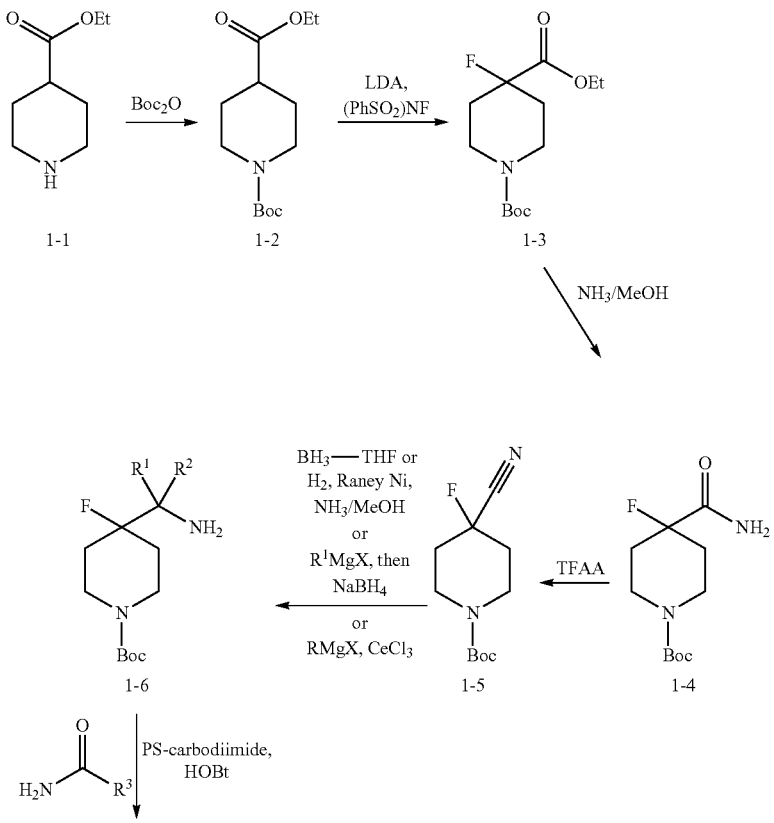

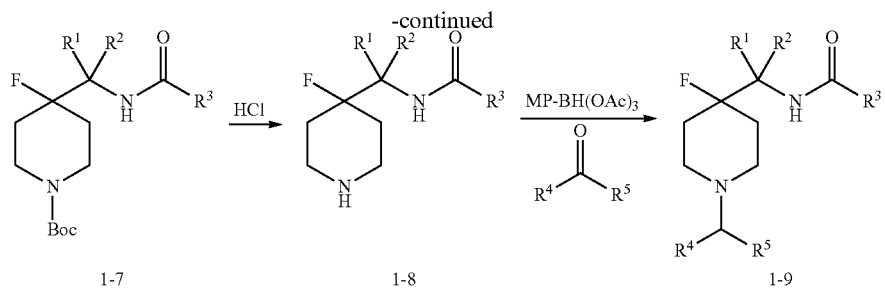

Treatment of commercially available ethyl isonipecotate (1-1) with di-tert-butyl dicarbonate gives tert-butyl carbamate 1-2. Fluorination is achieved by reaction with lithium diisopropylamide followed by N-fluorobenzenesulfonimide to give 1-3. Aminolysis of the ethyl ester with ammonia in methanol produces 1-4, which is dehydrated with trifluoroacetic acid anhydride, giving nitrile 1-5. Hydrogenation yields α-unsubstituted amine 1-6. Alternatively, addition of an organometallic reagent followed by reduction gives α-monosubstituted amine 1-6. Similarly, bis-addition of an organocerium to nitrile 1-5 yields α-disubstituted amine 1-6. Amide coupling furnishes 1-7, which is converted to the secondary amine 1-8 by treatment with HCl. Reductive amination with aldehydes or ketones produces compounds of the invention 1-9. Alternatively, compounds of the invention where $R_1=R_2=H$ may be prepared according to the general procedure outlined in Scheme 2.

Alcohol 2-1 is prepared in two steps from commercially available 1-BOC-4-piperidone by analogy to the route described by Vacher, et al. in *J. Med. Chem.* 1999, 42, 1648-1660.1 Conversion to sulfonate 2-2 is accomplished with p-TsCl, and displacement of the sulfonate by heating With potassium phthalimide yields 2-3. Primary amine 2-4 is unveiled by heating in ethanolamine. Amide coupling gives 2-5, which is converted to compounds of the invention 2-6 by treatment with HCl followed by reductive amination with aldehydes or ketones.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

SCHEME 2

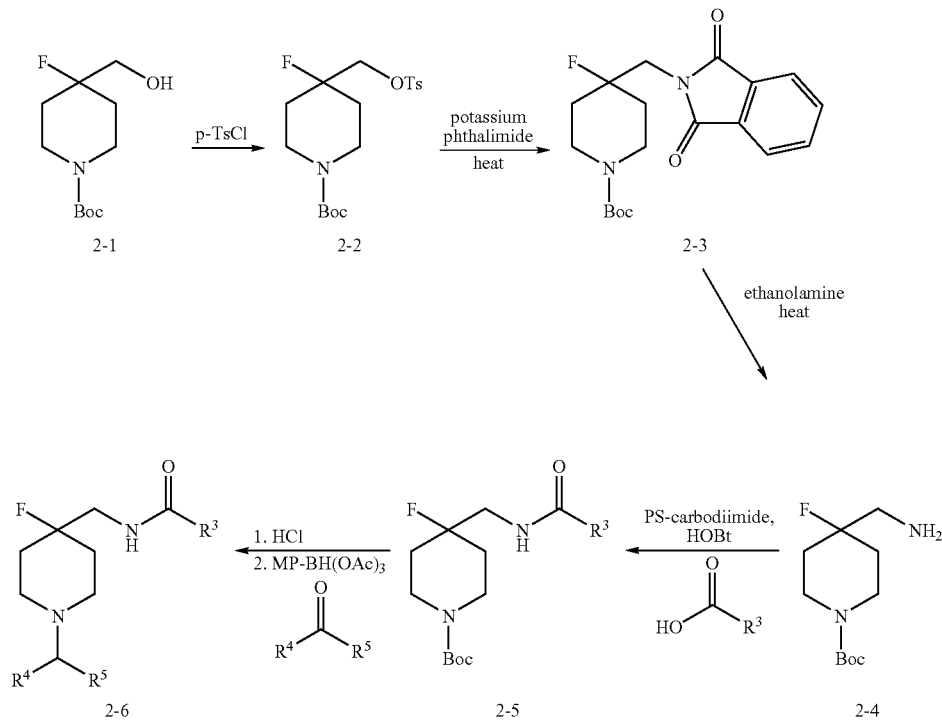

Example 1

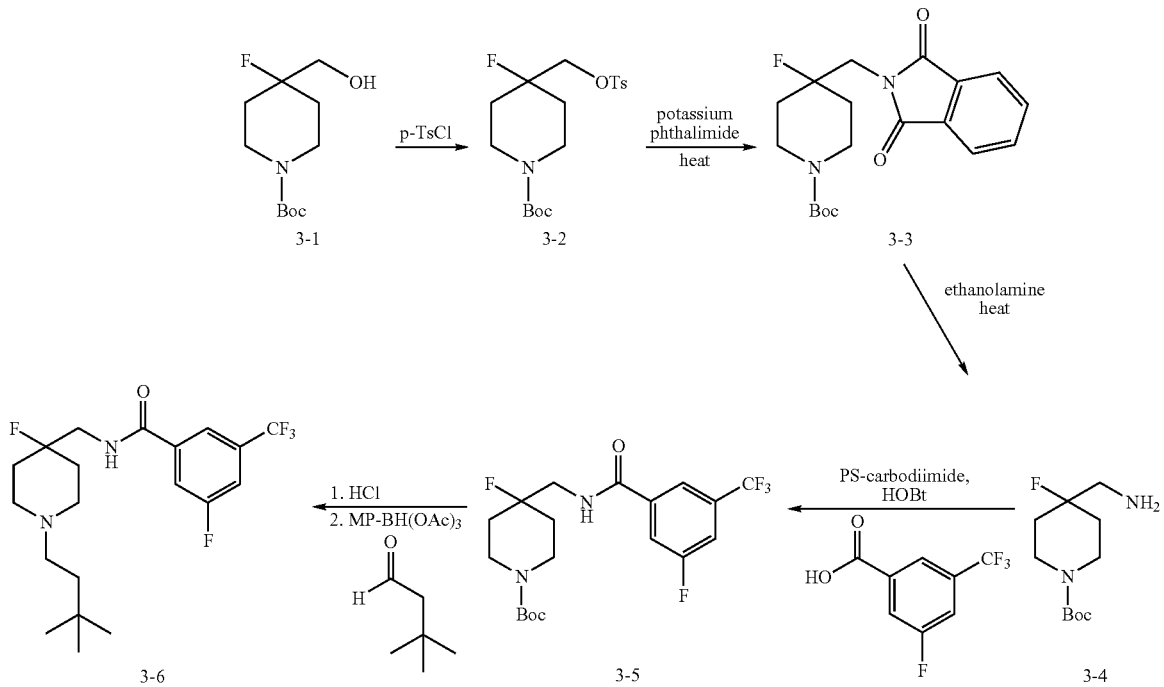

tert-butyl 4-fluoro-4-((tosyloxy)methyl)piperidine-1-carboxylate (3-2)

To a 0° C. mixture of 3-1 (4.55 g, 19.5 mmol) in 20 mL pyridine was added p-toluenesulfonyl chloride (4.09 g, 21.5 mmol). After the addition, the reaction was allowed to warm to ambient temperature and stir for 4 h. The reaction was then poured into $H_2O$ (100 mL) and extracted with $CH_2Cl_2$ (3×100 mL). The combined organic layers were washed with brine (150 mL), dried over $MgSO_4$, filtered, and concentrated in vacuo. Residual pyridine was azeotropically removed with heptane (4×), giving 6.78 g (90%) of a peach-orange oil. $^1$H NMR ($CDCl_3$, 300 MHz): 7.77 (d, J=8.4 Hz, 2H), 7.34 (d, J=8.4 Hz, 2H), 3.91 (br, 2H), 3.01 (m, 2H), 2.42 (s, 3H), 1.79 (m, 2H), 1.53 (m, 4H), 1.43 (s, 9H); MS (Electrospray): m/z 333.1 (M−t−Bu+H).

tert-butyl 4-((1,3-dioxoisoindolin-2-yl)methyl)-4-fluoropiperidine-1-carboxylate (3-3)

To a solution of 3-2 (6.78 g, 17.5 mmol) in 70 mL DMF was added potassium phthalimide (4.21 g, 22.7 mmol) and the mixture was heated at 150° C. for 2.5 h. The mixture was allowed to cool to ambient temperature, poured into $H_2O$ (150 mL), and extracted with EtOAc (3×150 mL). The combined organic layers were washed with brine (200 mL), dried over $MgSO_4$, filtered, and concentrated in vacuo, giving 11.0 g of crude 3-3 as a tan solid. $^1$H NMR ($CDCl_3$, 300 MHz): 7.85 (dd, J=5.4, 3.0 Hz, 2H), 7.76 (dd, J=5.4, 3.0 Hz, 2H), 3.96 (br, 2H), 3.04 (m, 2H), 1.70 (m, 6H), 1.43 (s, 9H); MS (Electrospray): m/z 385.2 (M+Na), 347.3 (M−Me+H).

tert-butyl 4-(aminomethyl)-4-fluoropiperidine-1-carboxylate (3-4)

A mixture of 3-3 (11.0 g) and 25 mL ethanolamine was stirred at 60° C. for 1 h. The reaction was then allowed to cool to room temperature, poured into ice-water (100 mL), and extracted with $CH_2Cl_2$ (3×100 mL). The combined organic layers were washed with brine (150 mL), dried over $MgSO_4$, filtered, and concentrated in vacuo, giving 5.82 g of crude 3-4 as a viscous amber oil. $^1$H NMR ($CDCl_3$, 300 MHz): 3.94 (br, 2H), 3.08 (m, 2H), 1.85 (m, 2H), 1.51 (m, 4H), 1.44 (s, 9H); MS (Electrospray): m/z 218.2 (M−Me+H), 177.2 (M−t−Bu+H).

tert-butyl 4-fluoro-4-((3-trifluoromethyl)benzamido)methyl)piperidine-1-carboxylate (3-5)

1-Hydrozybenzotriazole (0.973 g, 7.2 mmol) and 3-fluoro-5-(trifluoromethyl)benzoic acid (1.25 g, 6.0 mmol) were suspended in 30 mL dry $CH_2Cl_2$. Diisopropylethylamine (2.1 mL, 12.0 mmol) was added and all compounds went into solution. Amine 3-4 (1.39 g, 6.0 mmol) was added in 30 mL dry $CH_2Cl_2$. PS-carbodiimide resin (7.5 g, 12.0 mmol) was then added and the mixture was vigorously stirred overnight. MP-carbonate resin (4.0 g, 12.0 mmol) was added and stirring was resumed for 3 h. The reaction was then filtered to remove resin and concentrated in vacuo. A 40 g $SiO_2$ column was run in 0-50% EtOAc/hexanes, yielding 902 mg of 3-5 (36% over 3 steps) as a viscous yellow oil. $^1$H NMR ($CDCl_3$, 300 MHz): 7.84 (s, 1H), 7.73 (d, J=8.4 Hz, 1H), 7.45 (d, J=8.4 Hz, 1H), 3.92 (br, 2H), 3.65 (m, 2H), 3.10 (m, 2H), 1.68 (m, 4H), 1.43 (s, 9H); MS (Electrospray): m/z 445.2 (M+Na), 367.1 (M−t−Bu+H).

N-((1-(3,3-dimethylbutyl)-4-fluoropiperidin-4-yl)methyl)-3-fluoro-5-(trifluoromethyl)benzamide (3-6)

Carbamate 3-5 (0.835 g, 1.98 mmol) was dissolved in 7 mL dry $CH_2Cl_2$. 4 N HCl/dioxane (7.9 mL, 31.6 mmol) was added and the mixture was stirred overnight. All solvent was removed in vacuo, leaving a pale yellow solid. The solid was dissolved in 15 mL dry $CH_2Cl_2$ with minimal MeOH to aid solubility. 3,3-dimethylbutyraldehyde (0.273 mL, 2.18 mmol) was added, followed by MP-triacetoxyborohydride (1.83 g, 4.95 mmol) and the reaction was vigorously stirred overnight. The mixture was filtered to remove resin and concentrated in vacuo. A 12 g SiO$_2$ column was run in 0-20% MeOH/CH$_2$Cl$_2$, yielding 3-6 as a pale yellow oil. The tertiary amine 3-6 was converted to its HCl salt by treatment with 2 N HCl/Et$_2$O (2 mL), and removal of solvent under a stream of N$_2$, giving 356 mg (41% over two steps) of 3-6.HCl as a fine white powder. $^1$H NMR (CDCl$_3$, 300 MHz): 7.98 (s, 1H), 7.88 (d, J=8.7 Hz, 1H), 7.44 (d, J=8.7 Hz, 1H), 3.74 (m, 2H), 3.48 (m, 2H), 2.99 (m, 4H), 2.76 (m, 2H), 2.10 (m, 2H), 1.78 (m, 2H), 0.98 (s, 9H); MS (Electrospray): m/z 407.2 (M+H).

Example 2 hexanes, yielding 174 mg of nitrile 4-3 (76% over 2 steps) as a white solid. $^1$H NMR (CDCl$_3$, 300 MHz): 3.58 (m, 4H), 2.11 (m, 4H), 1.44 (s, 9H); MS (Electrospray): m/z 214.1 (M−Me+H), 173.1 (M−t−Bu+H).

tert-butyl 4-(aminomethyl)-4-fluoropiperidine-1-carboxylate (4-4)

To a 0° C. solution of 4-3 (8.83 g, 38.7 mmol) in 75 mL dry THF was added a solution of 1 M borane in THF (155 mL, 155 mmol) over 30 min. After 30 min more, the cold reaction was slowly quenched with EtOH (200 mL) and all solvent was removed in vacuo. The residue was taken up in saturated aq. NH$_4$Cl/EtOAc (150 mL) and extracted with EtOAc (3×150

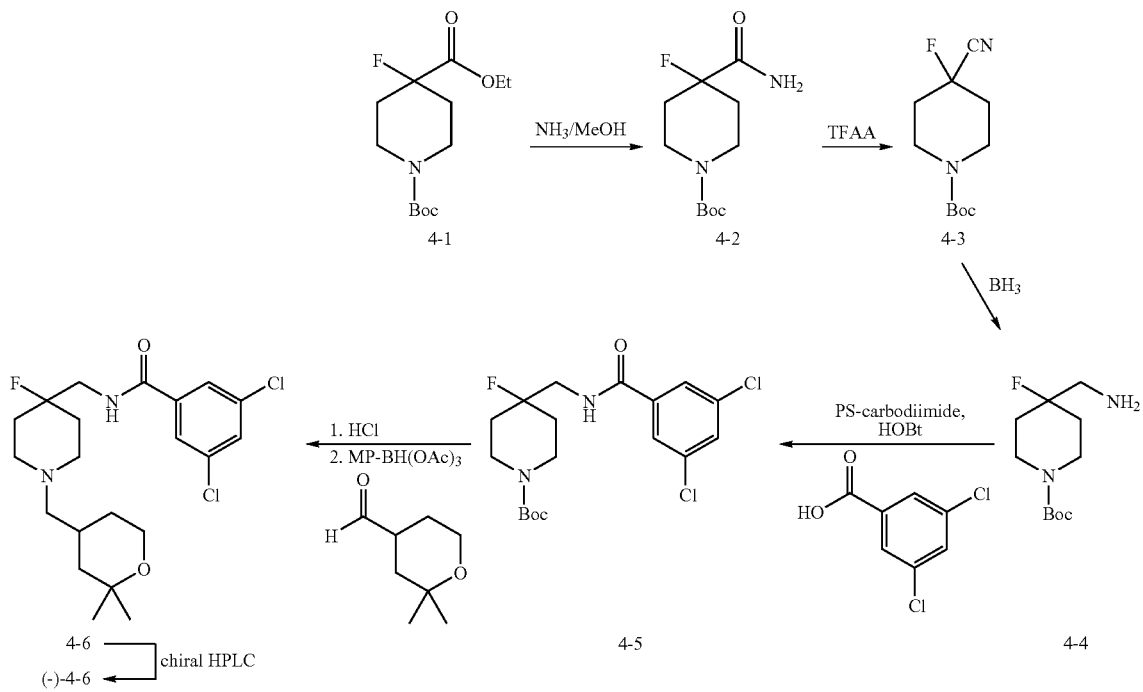

tert-butyl 4-carbamoyl-4-fluoropiperidine-1-carboxylate (4-2)

Commercially available ester 4-1 (0.275 g, 1.0 mmol) was treated with a 2 M solution of NH$_3$ in MeOH. The mixture was allowed to stir for 24 h at room temperature. All solvent was removed in vacuo. The crude amide 4-2 was carried forward. $^1$H NMR (CDCl$_3$, 300 MHz): 6.44 (br, 2H), 4.01 (br, 2H), 2.98 (br, 2H), 2.05 (m, 2H), 1.77 (m, 2H), 1.41 (s, 9H); MS (Electrospray): m/z 232.1 (M−Me+H), 191.1 (M−t−Bu+H).

tert-butyl-4-cyano-4-fluoropiperidine-1-carboxylate (4-3)

To a solution of 4-2 (0.246 g crude, 1.0 mmol) in 1 mL pyridine and 1 mL dry CH$_2$Cl$_2$ was added trifluoroacetic anhydride (0.525 g, 0.35 mL, 2.5 mmol). After 20 min, all solvent was removed in vacuo employing an n-heptane azeotrope (3×) to remove all traces of pyridine. The residue was partitioned between Et$_2$O and H$_2$O, washed with saturated aq. NaHCO$_3$, dried over MgSO$_4$, filtered, and concentrated in vacuo, giving 0.280 g of crude material as a yellow-orange oil that solidified. A 12 g SiO$_2$ column was run in 0-50% EtOAc/ mL). The organic layers were washed with 1 N aq. NaOH, brine, dried over MgSO$_4$, filtered, and concentrated in vacuo, giving crude 4-4 as a pale yellow oil. The crude amine 4-4 was carried forward. $^1$H NMR (CDCl$_3$, 300 MHz): 3.94 (br, 2H), 3.08 (m, 2H), 1.85 (m, 2H), 1.51 (m, 4H), 1.44 (s, 9H); MS (Electrospray): m/z 218.2 (M−Me+H), 177.2 (M−t−Bu+H).

tert-butyl 4-((3,5-dichlorobenzamido)methyl)-4-fluoropiperidine-1-carboxylate (4-5)

1-Hydroxybenzotriazole (6.27 g, 46.4 mmol) and 3,5-dichlorobenzoic acid (8.13 g, 42.6 mmol) were suspended in 210 mL dry CH$_2$Cl$_2$. Diisopropylethylamine (13.5 mL, 77.4 mmol) was added and all compounds went into solution. Amine 4-4 (10.4 g crude, 38.7 mmol) was added in 210 mL dry CH$_2$Cl$_2$. PS-carbodiimide resin (59.5 g, 77.4 mmol) was then added and the mixture was stirred for 14 h. MP-carbonate resin (41.8 g, 120 mmol) was added and stirring was resumed for 3 h. The reaction was then filtered to remove resin and concentrated in vacuo, yielding 22.2 g of crude 4-5 as a viscous yellow oil. The crude amide 4-5 was carried forward. $^1$H NMR (CDCl$_3$, 300 MHz): 7.94 (d, J=1.8 Hz, 1H), 7.66 (d, J=1.8 Hz, 2H), 6.44 (br t, 1H), 3.93 (br, 2H), 3.65 (br, 2H), 3.12 (br t, 2H), 1.83 (br t, 2H), 1.67 (m, 2H), 1.46 (s, 9H); MS (Electrospray): m/z 427.1 (M+Na), 349.1 (M−t−Bu+H).

3,5-dichloro-N-((1-((2,2-dimethyl-tetrahydro-2H-pyran-4-yl)methyl)-4-fluoropiperidin-4-yl)methyl) benzamide (4-6)

Carbamate 4-5 (22.2 g crude, 38.7 mmol) was dissolved in 155 mL dry $CH_2Cl_2$. 4 N HCl/dioxane (155 mL, 620 mmol) was added and the mixture was stirred for 2 h. All solvent was removed in vacuo, leaving 23.5 g of a yellow foam, which was dissolved in 300 mL dry $CH_2Cl_2$. 2,2-dimethyl-tetrahydro-2H-pyran-4-carbaldehyde (6.05 g, 42.6 mmol) {Purchased from Shanghai Chempartner Co., LTD. Prepared from 2,2-dimethyl-tetrahydropyran-4-one (see Liljebris et al. *Bioorg. Med. Chem.* 2002, 10, 3197-3212) by Wittig homologation and hydrolysis of the resulting methyl enol ether with formic acid.} was added in 100 mL $CH_2Cl_2$. Minimal MeOH was added to the reaction to aid solubility. MP-triacetoxyborohydride (50 g, 116 mmol) was then added and the reaction was stirred for 14 h. The mixture was filtered to remove resin and concentrated in vacuo, yielding 31.0 g of crude 4-6 as a yellow oil. Enantiomers were separated by gradient elution from 5-25% EtOH/hexane with 0.1% TFA on a ChiralPak AD column. The tertiary amines (+)-4-6 and (−)-4-6 were separately treated with saturated aq. $NaHCO_3$ (100 mL) and extracted with $CH_2Cl_2$ (3×75 mL). The free base was then converted to the HCl salt by treatment with 2 N HCl/Et$_2$O (5 mL), and removal of all solvent in vacuo. This process yielded 5.15 g of the faster-eluting enantiomer, (+)-4-6, and 4.37 g of the slower-eluting one, (−)-4-6, as fine tan powders. The four-step yield of the HCl salt of (−)-4-6 from 4-3 was 48%. $^1$H NMR (CDCl$_3$, 300 MHz): 7.83 (s, 2H), 7.45 (s, 1H), 3.70 (m, 3H), 3.51 (m, 2H), 3.04 (m, 2H), 2.83 (m, 3H), 2.32 (br, 3H), 2.10 (m, 2H), 1.95 (br, 1H), 1.76 (br, 1H), 1.52 (d, J=6.0 Hz, 1H), 1.43 (d, J=6.0 Hz, 1H), 1.22 (app s, 6H); MS (HR Electrospray): m/z 431.1161 (M+H).

Example 3

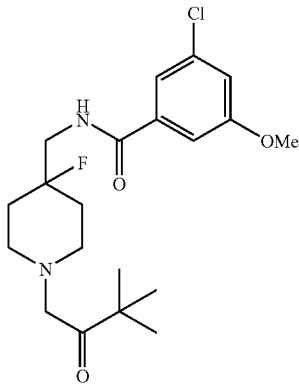 [SMILES: COc1cc(Cl)cc(C(=O)NCC2(F)CCN(CC(=O)C(C)(C)C)CC2)c1]

3-chloro-N-{[1-(3,3-dimethyl-2-oxobutyl)-4-fluoropiperidin-4-yl]methyl}-5-methoxybenzamide To a solution of benzyl 4-(aminomethyl)-4-fluoro-piperidine-1-carboxylate (Claiborne, C. F.; Butcher, J. W. Claremon, D. A.; Libby, B. E.; Claremon, D. A.; Liverton, N.J.; Munson, P. M.; Nguyen, K. T.; Phillips, B.; Thompson, W.; McCauley, J. A., PCT Int. Appl WO2002068409 (2002)) (2.2 g, 8.1 mmol) in $CH_2Cl_2$ (20 mL) at room temperature was added 3-chloro-5-methoxylbenzoyl acid (1.7 g, 9.0 mmol), HOAt (1.3 g, 9.8 mmol) and EDC (1.9 g, 9.8 mmol). The resulting mixture was allowed to stir at room temperature for 2 h. LC-MS indicated that the reaction was completed. The reaction mixture was diluted with water (20 mL) and the two layers were separated. The aqueous layer was extracted with $CH_2Cl_2$ twice (20 mL each). The combined organic layers were dried (Na$_2$SO$_4$), filtered and the filtrated was concentrated. The crude residue was dissolved in $CH_2Cl_2$ (10 mL), and to this mixture was then added HBr in AcOH (30 wt %, 10 mL). The reaction was vented through a needle to a concentrated aqueous solution of NaOH. After stirring at room temperature for 15 minutes, LC-MS showed complete consumption of the starting material. Diethyl ether (100 mL) was then added to the reaction mixture. The precipitates were collected, washed with more diethyl ether and dissolved in H$_2$O with the residue left in the reaction flask. The water solution was then transferred to a separatory funnel, and solid NaHCO$_3$ (until the solution was basic) and $CH_2Cl_2$ (100 mL) were added. After vigorously shaking, the two layers were separated. The water layers were extracted with $CH_2Cl_2$ (>3x) until LC-MS indicated that no product left. The combined organic layer was washed with brine, dried (NaSO$_4$), filtered and conc. A portion of the crude product obtained (4-F piperidine intermediate, 0.19 g, 0.63 mmol) was then mixed with K$_2$CO$_3$ (0.26 g, 1.9 mmol), 1-bromopinacolone (0.13 mL, 0.95 mmol) in MeCN (2 mL) in a sealed a tube. The resulting mixture was heated at 80° C. for 12 hours. The reaction mixture was filtered and purified by preparative HPLC (5->95% CH$_3$CN/H$_2$O over 30 min, 0.05% added TFA, C18 SunFire 19×150 mm) to give title compound as a white solid upon freeze-drying. $^1$H NMR (400 MHz, CDCl$_3$): δ 8.12 (t, J=6.3 Hz, 1H), 7.41 (t, J=1.7 Hz, 1H), 7.31 (dd, J=2.3, 1.5 Hz, 1H), 7.04 (t, J=2.0 Hz, 1H), 3.85 (s, 3H), 3.72 (d, J=5.1 Hz, 1H), 3.67 (d, J=5.0 Hz, 1H), 3.55-3.52 (m, 2H), 3.50-3.32 (m, 2H), 3.24 (t, J=11.0 Hz, 1H), 2.35-2.28 (m, 1H), 2.27-2.18 (m, 1H), 2.13-2.07 (m, 2H), 1.20 (s, 9H). HRMS (ES) calcd for $C_{20}H_{28}ClFN_2O_3$ [M+1]$^+$: 399.1845, found 399.1844.

Example 4

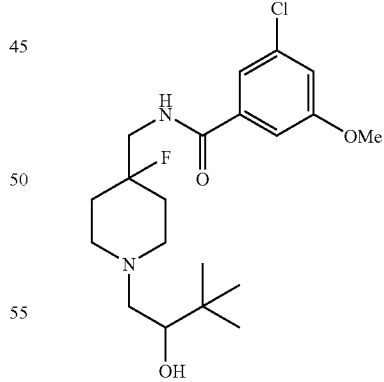

3-chloro-N-({4-fluoro-1-[(2S)-2-hydroxy-3,3-dimethylbutyl]piperidin-4-yl}methyl)-5-methoxybenzamide and 3-chloro-N-({4-fluoro-1-[(2R)-2-hydroxy-3,3-dimethylbutyl]piperidin-4-yl}methyl)-5-methoxybenzamide To a solution of 3-chloro-N-{[1-(3,3-dimethyl-2-oxobutyl)-4-fluoropiperidin-4-yl]methyl}-5-methoxybenzamide (0.091 g, 0.23 mmol) in MeOH (1 mL) was added NaBH$_4$ (0.017 g, 0.46 mmol). The mixture was stirred at room temperature for 15 minutes. Additional NaBH$_4$ (10 mg) was added and the reaction was stirred for 10 minutes. The solvent was removed and the residue was purified by preparative HPLC (5->95% CH$_3$CN/H$_2$O over 30 min, 0.05% added TFA, C18 SunFire 19×150 mm) to give title compound as a white solid upon freeze-drying. The two enantiomers were separated on a chiral column (92% CO$_2$, 8% MeOH, Chiral-Pak AS, 2×25 cm, 10μ,). $^1$H NMR (400 MHz, CDCl$_3$): δ 7.29 (s, 1H), 7.24 (s, 1H), 7.04 (s, 1H), 6.37 (bs, 1H), 3.85 (s, 3H), 3.75-3.58 (m, 2H), 3.34 (dd, J=10.6, 3.3 Hz, 1H), 2.86 (dd, J=7.9, 4.0 Hz, 1H), 2.67 (t, J=11.0, 1H), 2.61 (t, J=11.5 Hz, 1H), 2.40-2.27 (m, 3H), 1.92-1.83 (m, 2H), 1.80-1.64 (m, 2H), 0.91 (s, 9H). HRMS (ES) calcd for C$_{20}$H$_{30}$ClFN$_2$O$_3$ [M+1]$^+$: 401.2002, found 401.2018.

Example 5

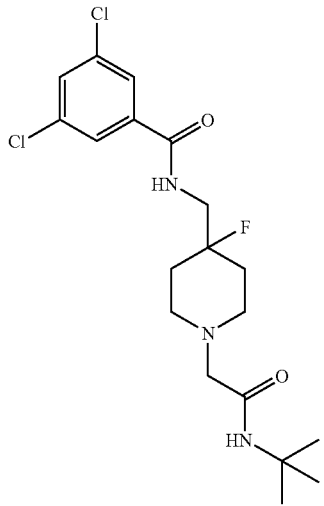 [SMILES: CC(C)(C)NC(=O)CN1CCC(F)(CNC(=O)c2cc(Cl)cc(Cl)c2)CC1]

N-(1-[2-(tert-butylamino)-2-oxoethyl]-4-fluoropiperidin-4-yl}methyl)-3,5-dichlorobenzamide To a solution of tert-butylamine (1.0 ml, 9.5 mmol) and Et$_3$N (1.3 ml, 9.5 mmol) in CH$_2$Cl$_2$ at 0° C. was added chloroacetyl chloride (0.76 ml, 9.5 mmol) dropwise. The reaction mixture was stirred at 0° C. for 15 min, and washed with 1.0 N HCl, water and brine. The organic layer was dried over Na$_2$SO$_4$ and filtered. The filtrate was concentrated to give 1.1 g of tan-colored solid as the crude intermediate 1. It was used without further purification. To a solution of benzyl 4-(aminomethyl)-4-fluoro-piperidine-1-carboxylate (Claiborne, C. F.; Butcher, J. W. Claremon, D. A.; Libby, B. E.; Claremon, D. A.; Liverton, N.J.; Munson, P. M.; Nguyen, K. T.; Phillips, B.; Thompson, W.; McCauley, J. A., PCT Int. Appl WO2002068409 (2002)) (4.0 g, 15 mmol) and triethylamine (2.1 ml, 15 mmol) in 75 ml of CH$_2$Cl$_2$ at 0° C. was added 3,5-dichloro benzoyl chloride (3.1 g, 15 mmol) in 25 ml of CH$_2$Cl$_2$. The resulting mixture was stirred for 1 h, and LC-MS showed a good conversion. HBr in AcOH (33% wt) (7.2 ml, 120 mmol) was added slowly with a NaOH (40% aqueous solution) trap for the HBr gas released. After stirred at RT for 1 h, the reaction was complete as judged by LC-MS. The reaction mixture was poured into 200 ml of Et$_2$O. A tan-colored solid precipitated and collected by filtration. The solid was washed with Et$_2$O and dried give a tan-colored solid as the crude product. Purification by silica gel column (0-10% MeOH in CH$_2$Cl$_2$, 20 min. gradient) gave 3.125 g (68% yield) of white solid as the desired intermediate 2. A mixture of the intermediate 1 (18 mg, 0.117 mmol), intermediate 2 (40 mg, 0.117 mmol), and triethylamine (0.017 ml, 0.117 mmol) in 0.5 ml of dry DMF was stirred at RT overnight. LC-MS showed the reaction was complete. The reaction mixture was washed with saturated NaHCO3 solution and brine. The organic layer was dried over Na$_2$SO$_4$, filtered and concentrated. The residue was purified using preparative HPLC (5->95% CH$_3$CN/H$_2$O over 30 min, 0.05% added TFA, C18 SunFire 19×150 mm) to afford 40.86 mg (83%) of the title compound. $^1$H NMR (CDCl$_3$, 400 MHz) δ 7.68 (d, J=1.8 Hz, 2H); 7.52 (t, J=1.8 Hz, 1H); 7.44 (s, 1H); 6.49 (br s, 1H); 3.95 (dd, J1=19.2 Hz, J 2=6.2 Hz, 2H); 3.61 (s, 2H); 3.51 (d, J=12.3 Hz, 2H); 3.24 (t, J=12.1 Hz, 2H); 2.35 (m, 2H); 2.10 (m, 2H); 1.34 (s, 9H); HRMS (ES) calcd for C$_{19}$H$_{27}$Cl$_2$FN$_3$O$_3$ [M+1]$^+$: 418.1459, found 418.1459.

TABLE 1

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| 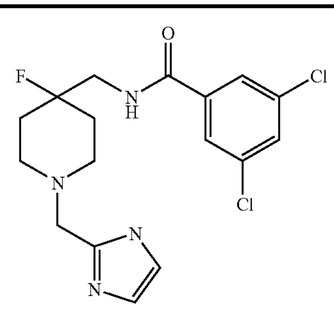 | 385.1 | 3,5-dichloro-N-{[4-fluoro-1-(1H-imidazol-2-ylmethyl)piperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 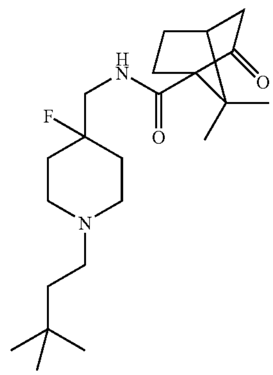 [SMILES: CC(C)(C)CCN1CCC(F)(CNC(=O)C23CCC(CC2=O)C3(C)C)CC1] | 381.3 | N-{[1-(3,3-dimethylbutyl)-4-fluoropiperidin-4-yl]methyl}-7,7-dimethyl-2-oxobicyclo[2.2.1]heptane-1-carboxamide |
| 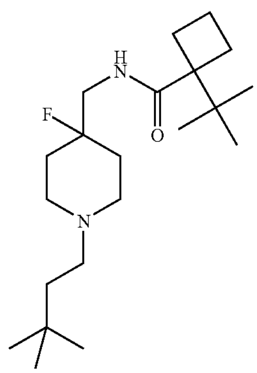 [SMILES: CC(C)(C)CCN1CCC(F)(CNC(=O)C2(C(C)(C)C)CCC2)CC1] | 367.2 | N-{[1-(3,3-dimethylbutyl)-4-fluoropiperidin-4-yl]methyl}-1-(trifluoromethyl)cyclobutanecarboxamide |
| 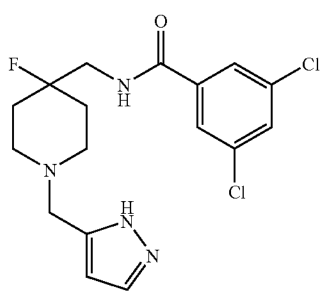 [SMILES: O=C(NCC1(F)CCN(Cc2ccn[nH]2)CC1)c1cc(Cl)cc(Cl)c1] | 385.1 | 3,5-dichloro-N-{[4-fluoro-1-(1H-pyrazol-5-ylmethyl)piperidin-4-yl]methyl}benzamide |
| 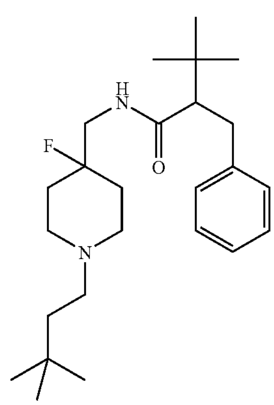 [SMILES: CC(C)(C)CCN1CCC(F)(CNC(=O)C(Cc2ccccc2)C(C)(C)C)CC1] | 405.3 | 2-benzyl-N-{[1-(3,3-dimethylbutyl)-4-fluoropiperidin-4-ylmethyl}-3,3-dimethylbutanamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 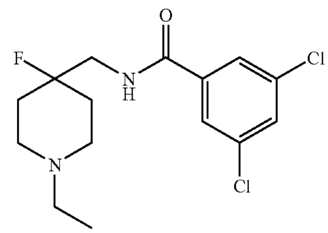 [SMILES: CCN1CCC(F)(CNC(=O)c2cc(Cl)cc(Cl)c2)CC1] | 333.1 | 3,5-dichloro-N-[(1-ethyl-4-fluoropiperidin-4-yl)methyl]benzamide |
| 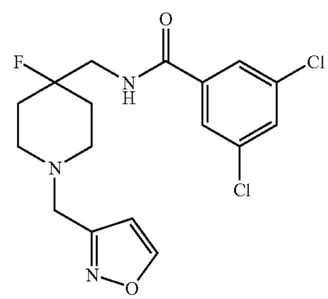 [SMILES: O=C(NCC1(F)CCN(Cc2ccon2)CC1)c1cc(Cl)cc(Cl)c1] | 386.1 | 3,5-dichloro-N-{[4-fluoro-1-(isoxazol-3-ylmethyl)piperidin-4-yl]methyl}benzamide |
| 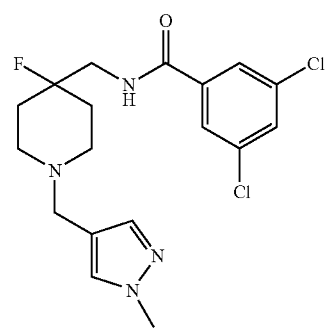 [SMILES: Cn1cc(CN2CCC(F)(CNC(=O)c3cc(Cl)cc(Cl)c3)CC2)cn1] | 399.1 | 3,5-dichloro-N-({4-fluoro-1-[(1-methyl-1H-pyrazol-4-yl)methyl]piperidin-4-yl}methyl)benzamide |
| 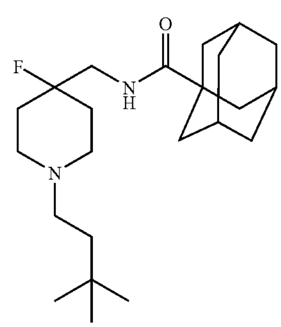 [SMILES: CC(C)(C)CCN1CCC(F)(CNC(=O)C23CC4CC(CC(C4)C2)C3)CC1] | 379.4 | N-{[1-(3,3-dimethylbutyl)-4-fluoropiperidin-4-yl]methyl}adamantane-1-carboxamide |
| 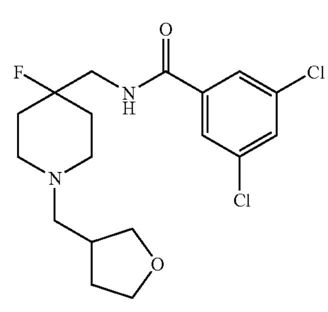 [SMILES: O=C(NCC1(F)CCN(CC2CCOC2)CC1)c1cc(Cl)cc(Cl)c1] | 389.1 | 3,5-dichloro-N-{[4-fluoro-1-(tetrahydrofuran-3-ylmethyl)piperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
| --- | --- | --- |
| 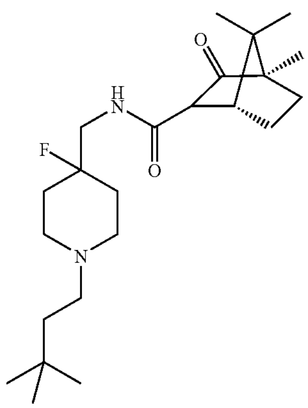 [SMILES: CC(C)(C)CCN1CCC(F)(CNC(=O)C2C(=O)[C@]3(C)CC[C@H]2C3(C)C)CC1] | 395.3 | (1R,4R)-N-{[1-(3,3-dimethylbutyl)-4-fluoropiperidin-4-yl]methyl}-4,7,7-trimethyl-3-oxobicyclo[2.2.1]heptane-2-carboxamide |
| 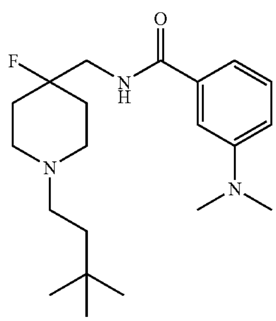 [SMILES: CN(C)c1cccc(C(=O)NCC2(F)CCN(CCC(C)(C)C)CC2)c1] | 364.3 | 3-(dimethylamino)-N-{[1-(3,3-dimethylbutyl)-4-fluoropiperidin-4-yl]methyl}benzamide |
| 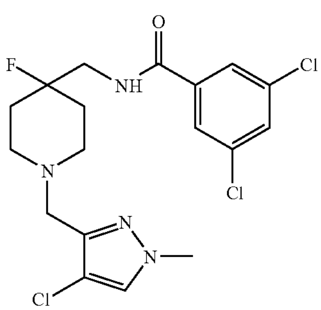 [SMILES: Cn1cc(Cl)c(CN2CCC(F)(CNC(=O)c3cc(Cl)cc(Cl)c3)CC2)n1] | 433.1 | 3,5-dichloro-N-({1-[(4-chloro-1-methyl-1H-pyrazol-3-yl)methyl]-4-fluoropiperdin-4-yl}methyl)benzamide |
| 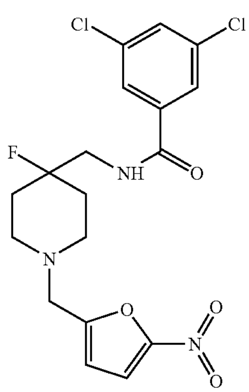 [SMILES: O=C(NCC1(F)CCN(Cc2ccc([N+](=O)[O-])o2)CC1)c1cc(Cl)cc(Cl)c1] | 430.1 | 3,5-dichloro-N-({4-fluoro-1-[(5-nitro-2-furyl)methyl]piperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| 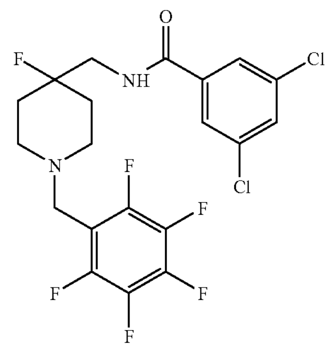 [SMILES: O=C(NCC1(F)CCN(Cc2c(F)c(F)c(F)c(F)c2F)CC1)c1cc(Cl)cc(Cl)c1] | 485.1 | 3,5-dichloro-N-{[4-fluoro-1-(pentafluorobenzyl)piperidin-4-yl]methyl}benzamide |
| 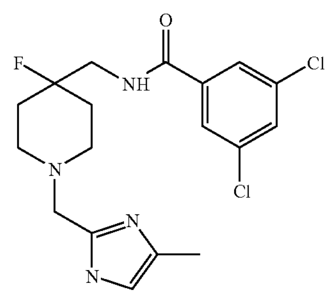 [SMILES: Cc1c[nH]c(CN2CCC(F)(CNC(=O)c3cc(Cl)cc(Cl)c3)CC2)n1] | 399.1 | 3,5-dichloro-N-({4-fluoro-1-[(4-methyl-1H-imidazol-2-yl)methyl]piperidin-4-yl}methyl)benzamide |
| 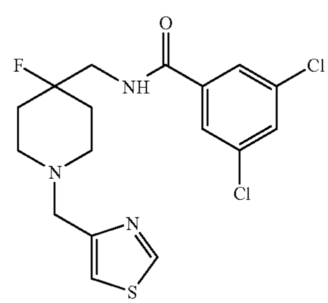 [SMILES: O=C(NCC1(F)CCN(Cc2cscn2)CC1)c1cc(Cl)cc(Cl)c1] | 402.1 | 3,5-dichloro-N-{[4-fluoro-1-(1,3-thiazol-4-ylmethyl)piperidin-4-yl]methyl}benzamide |
| 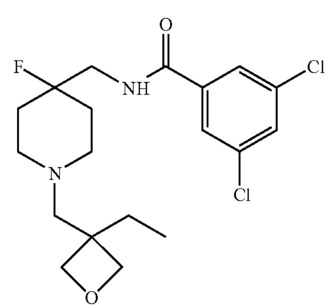 [SMILES: CCC1(CN2CCC(F)(CNC(=O)c3cc(Cl)cc(Cl)c3)CC2)COC1] | 403.1 | 3,5-dichloro-N-({1-[(3-ethyloxetan-3-yl)methyl]-4-fluoropiperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 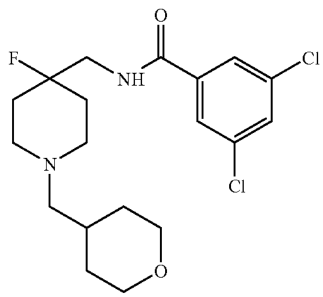 | 403.2 | 3,5-dichloro-N-{[4-fluoro-1-(tetrahydro-2H-pyran-4-ylmethyl)piperidin-4-yl]methyl}benzamide |
| 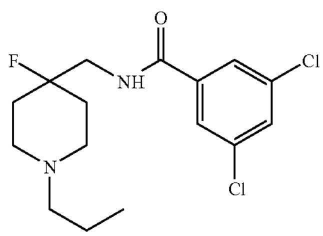 [SMILES: CCCN1CCC(F)(CNC(=O)c2cc(Cl)cc(Cl)c2)CC1] | 347.1 | 3,5-dichloro-N-[(4-fluoro-1-propylpiperidin-4-yl)methyl]benzamide |
| 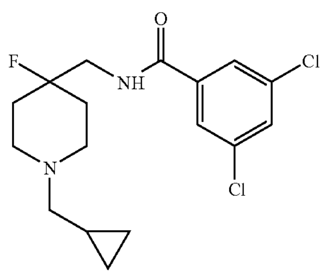 [SMILES: O=C(NCC1(F)CCN(CC2CC2)CC1)c1cc(Cl)cc(Cl)c1] | 359.1 | 3,5-dichloro-N-{[1-(cyclopropylmethyl)-4-fluoropiperidin-4-yl]methyl}benzamide |
| 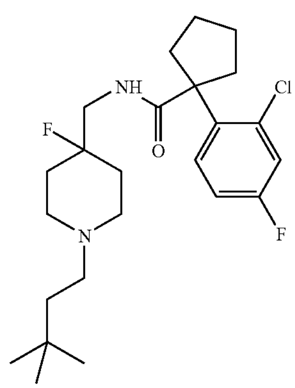 [SMILES: CC(C)(C)CCN1CCC(F)(CNC(=O)C2(c3ccc(F)cc3Cl)CCCC2)CC1] | 441.2 | 1-(2-chloro-4-fluorophenyl)-N-{[1-(3,3-dimethylbutyl)-4-fluoropiperidin-4-yl]methyl}cyclopentanecarboxamide |
| 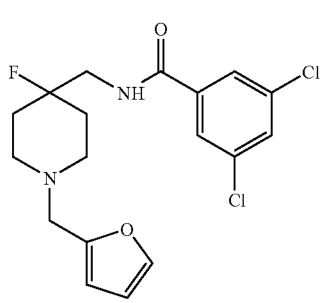 | 385.1 | 3,5-dichloro-N-{[4-fluoro-1-(2-furylmethyl)piperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH⁺) m/z | NAME |
|---|---|---|
| 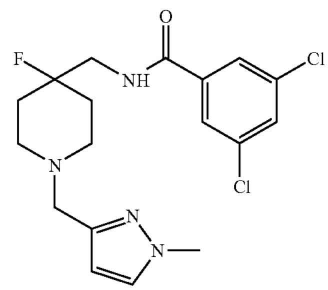 [SMILES: Cn1ccc(CN2CCC(F)(CNC(=O)c3cc(Cl)cc(Cl)c3)CC2)n1] | 399.1 | 3,5-dichloro-N-({4-fluoro-1-[(1-methyl-1H-pyrazol-3-yl)methyl]piperidin-4-yl}methyl)benzamide |
| 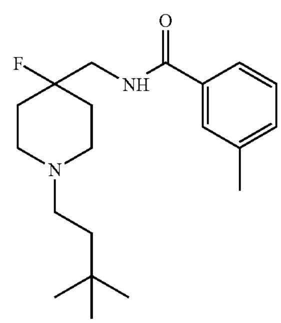 [SMILES: Cc1cccc(C(=O)NCC2(F)CCN(CCC(C)(C)C)CC2)c1] | 335.2 | N-{[1-(3,3-dimethylbutyl)-4-fluoropiperidin-4-yl]methyl}-3-methylbenzamide |
| 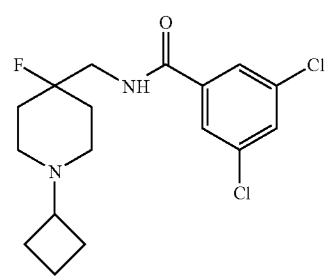 [SMILES: O=C(NCC1(F)CCN(C2CCC2)CC1)c1cc(Cl)cc(Cl)c1] | 359.1 | 3,5-dichloro-N-[(1-cyclobutyl-4-fluoropiperidin-4-yl)methyl]benzamide |
| 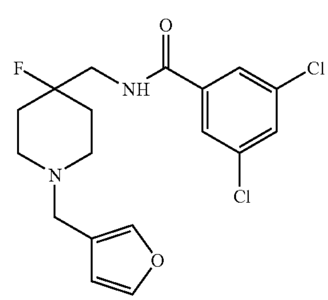 | 385.1 | 3,5-dichloro-N-{[4-fluoro-1-(3-furylmethyl)piperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 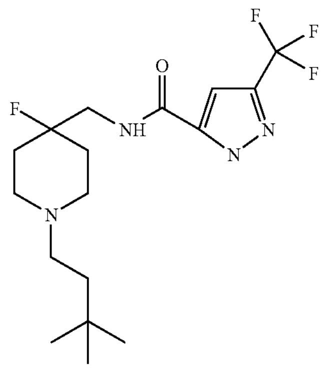 [SMILES: CC(C)(C)CCN1CCC(F)(CNC(=O)c2cc(C(F)(F)F)n[nH]2)CC1] | 379.2 | N-{[1-(3,3-dimethylbutyl)-4-fluoropiperidin-4-yl]methyl}-3-(trifluoromethyl)-1H-pyrazole-5-carboxamide |
| 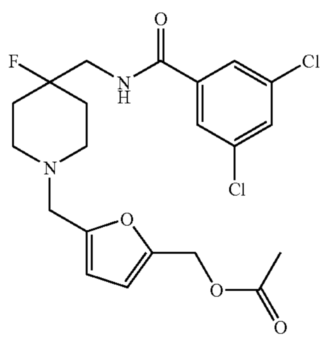 [SMILES: CC(=O)OCc1ccc(CN2CCC(F)(CNC(=O)c3cc(Cl)cc(Cl)c3)CC2)o1] | 457.1 | {5-[(4-{[(3,5-dichlorobenzoyl)amino]-methyl}-4-fluoropiperidin-1-yl)methyl]-2-furyl}methyl acetate |
| 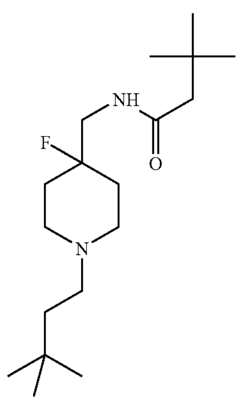 [SMILES: CC(C)(C)CCN1CCC(F)(CNC(=O)CC(C)(C)C)CC1] | 315.3 | N-{[1-(3,3-dimethylbutyl)-4-fluoropiperidin-4-yl]methyl}-3,3-dimethylbutanamide |
| 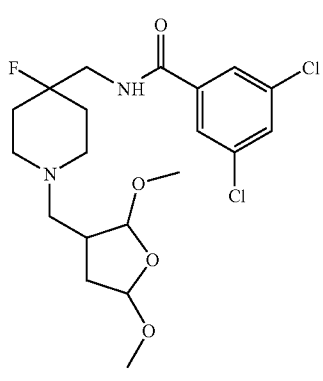 [SMILES: COC1CC(CN2CCC(F)(CNC(=O)c3cc(Cl)cc(Cl)c3)CC2)C(OC)O1] | 449.1 | 3,5-dichloro-N-({1-[(2,5-dimethoxy-tetrahydrofuran-3-yl)methyl]-4-fluoropiperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
| --- | --- | --- |
|  | 361.1 | N-[(1-butyl-4-fluoropiperidin-4-yl)methyl]-3,5-dichlorobenzamide |
| 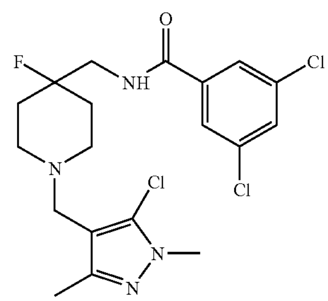 [SMILES: Cc1nn(C)c(Cl)c1CN1CCC(F)(CNC(=O)c2cc(Cl)cc(Cl)c2)CC1] | 447.1 | 3,5-dichloro-N-({1-[(5-chloro-1,3-dimethyl-1H-pyrazol-4-yl)methyl]-4-fluoropiperidin-4-yl}methyl)benzamide |
| 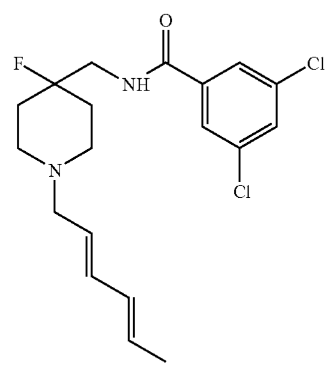 [SMILES: C/C=C/C=C/CN1CCC(F)(CNC(=O)c2cc(Cl)cc(Cl)c2)CC1] | 385.1 | 3,5-dichloro-N-({4-fluoro-1-[(2E,4E)-hexa-2,4-dien-1-yl]piperidin-4-yl}methyl)benzamide |
|  | 361.1 | 3,5-dichloro-N-[(4-fluoro-1-isobutyl-piperidin-4-yl)methyl]benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 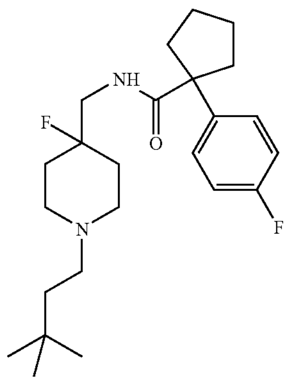 [SMILES: CC(C)(C)CCN1CCC(F)(CNC(=O)C2(c3ccc(F)cc3)CCCC2)CC1] | 407.3 | N-{[1-(3,3-dimethylbutyl)-4-fluoropiperidin-4-yl]methyl)-1-(4-fluorophenyl)cyclo-pentanecarboxamide |
| 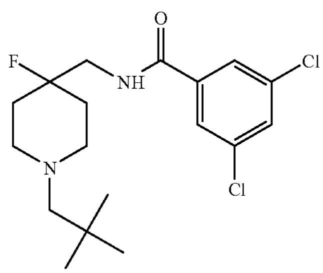 [SMILES: CC(C)(C)CN1CCC(F)(CNC(=O)c2cc(Cl)cc(Cl)c2)CC1] | 375.1 | 3,5-dichloro-N-{[1-(2,2-dimethylpropyl)-4-fluoropiperidin-4-yl]methyl}benzamide |
| 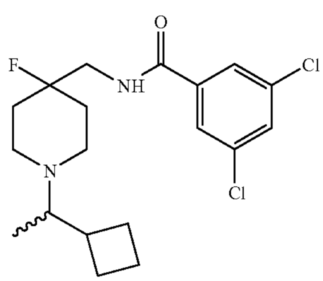 [SMILES: CC(C1CCC1)N1CCC(F)(CNC(=O)c2cc(Cl)cc(Cl)c2)CC1] | 387.1 | 3,5-dichloro-N-{[1-(1-cyclobutylethyl)-4-fluoropiperidin-4-yl]methyl}benzamide |
| 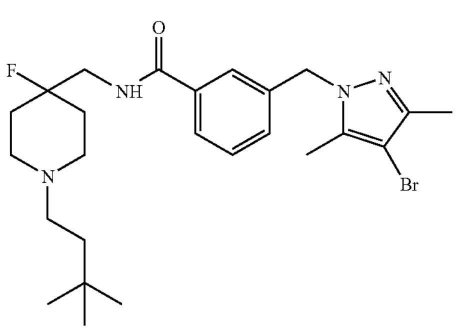 [SMILES: Cc1nn(Cc2cccc(C(=O)NCC3(F)CCN(CCC(C)(C)C)CC3)c2)c(C)c1Br] | 507.2 | 3-[(4-bromo-3,5-dimethyl-1H-pyrazol-1-yl)methyl]-N-{[1-(3,3-dimethylbutyl)-4-fluoropiperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 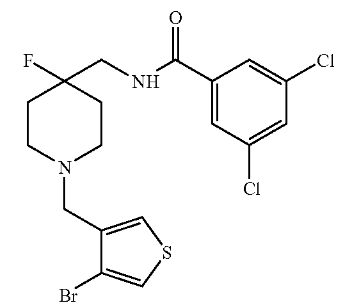 [SMILES: O=C(NCC1(F)CCN(Cc2cscc2Br)CC1)c1cc(Cl)cc(Cl)c1] | 479.0 | N-({1-[(4-bromo-3-thienyl)methyl]-4-fluoropiperidin-4-yl}methyl)-3,5-dichlorobenzamide |
| 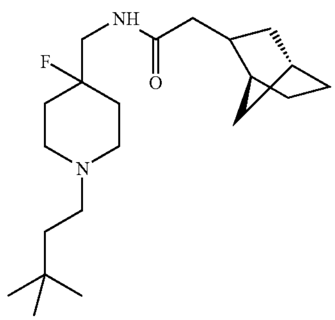 [SMILES: CC(C)(C)CCN1CCC(F)(CNC(=O)CC2C[C@@H]3CC[C@H]2C3)CC1] | 353.3 | 2-[(1S,4R)-bicyclo[2.2.1]hept-2-yl]-N-{[1-(3,3-dimethylbutyl)-4-fluoropiperidin-4-yl]methyl}acetamide |
| 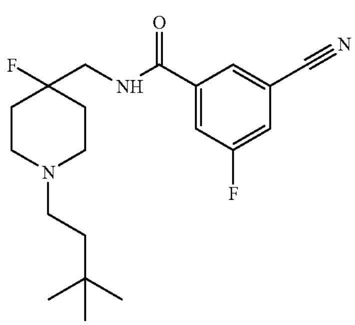 [SMILES: CC(C)(C)CCN1CCC(F)(CNC(=O)c2cc(F)cc(C#N)c2)CC1] | 364.2 | 3-cyano-N-{[1-(3,3-dimethylbutyl)-4-fluoropiperidin-4-yl]methyl}-5-fluorobenzamide |
| 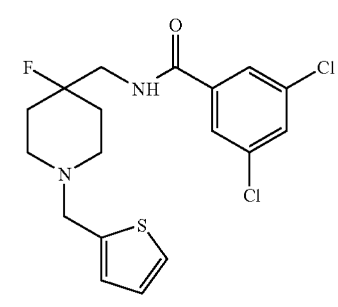 [SMILES: O=C(NCC1(F)CCN(Cc2cccs2)CC1)c1cc(Cl)cc(Cl)c1] | 401.1 | 3,5-dichloro-N-{[4-fluoro-1-(2-thienylmethyl)piperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 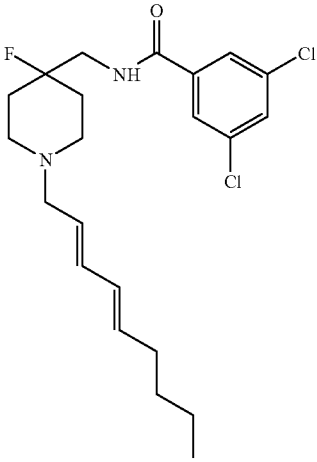 [SMILES: CCCC/C=C/C=C/CN1CCC(F)(CNC(=O)c2cc(Cl)cc(Cl)c2)CC1] | 427.2 | 3,5-dichloro-N-({4-fluoro-1-[(2E,4E)-nona-2,4-dien-1-yl]piperidin-4-yl}methyl)benzamide |
| 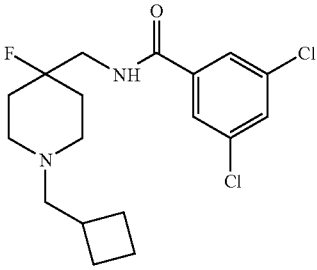 [SMILES: O=C(NCC1(F)CCN(CC2CCC2)CC1)c1cc(Cl)cc(Cl)c1] | 373.1 | 3,5-dichloro-N-{[1-(cyclobutylmethyl)-4-fluoropiperidin-4-yl]methyl}benzamide |
| 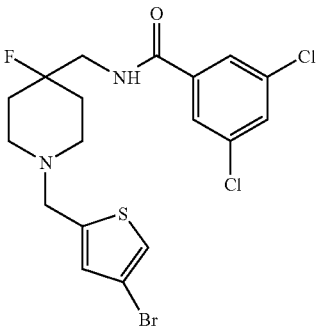 [SMILES: O=C(NCC1(F)CCN(Cc2cc(Br)cs2)CC1)c1cc(Cl)cc(Cl)c1] | 479.0 | N-({1-[(4-bromo-2-thienyl)methyl]-4-fluoropiperidin-4-yl}methyl)-3,5-dichlorobenzamide |
| 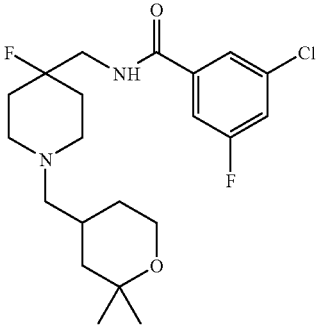 [SMILES: CC1(C)CC(CN2CCC(F)(CNC(=O)c3cc(F)cc(Cl)c3)CC2)CCO1] | 415.2 | 3-chloro-N-({1-[(2,2-dimethyltetrahydro-2H-pyran-4-yl)methyl]-4-fluoropiperidin-4-yl}methyl)-5-fluorobenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 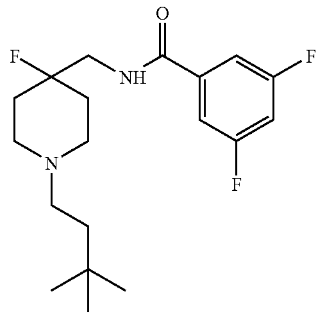 [SMILES: CC(C)(C)CCN1CCC(F)(CNC(=O)c2cc(F)cc(F)c2)CC1] | 357.2 | N-{[1-(3,3-dimethylbutyl)-4-fluoropiperidin-4-yl]methyl}-3,5-difluorobenzamide |
| 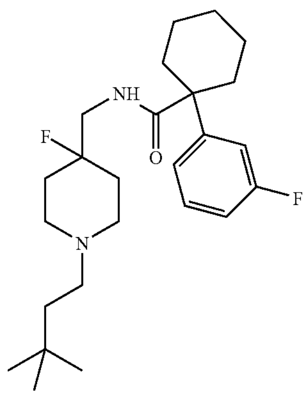 [SMILES: CC(C)(C)CCN1CCC(F)(CNC(=O)C2(c3cccc(F)c3)CCCCC2)CC1] | 421.3 | N-{[1-(3,3-dimethylbutyl)-4-fluoropiperidin-4-yl]methyl}-1-(3-fluorophenyl)cyclohexane-carboxamide |
| 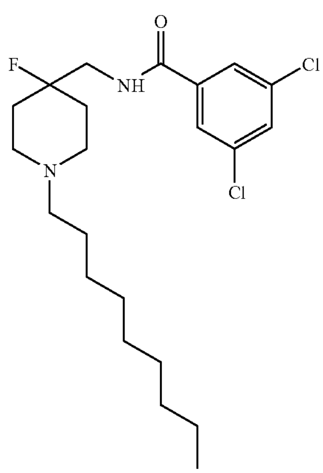 [SMILES: CCCCCCCCCN1CCC(F)(CNC(=O)c2cc(Cl)cc(Cl)c2)CC1] | 431.2 | 3,5-dichloro-N-[(4-fluoro-1-nonylpiperidin-4-yl)methyl]benzamide |
| 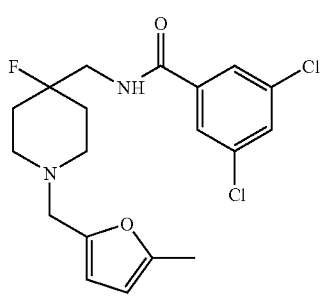 [SMILES: Cc1ccc(CN2CCC(F)(CNC(=O)c3cc(Cl)cc(Cl)c3)CC2)o1] | 399.1 | 3,5-dichloro-N-({4-fluoro-1-[(5-methyl-2-furyl)methyl]piperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 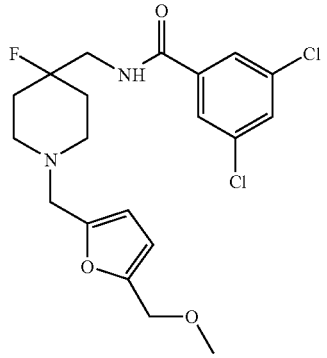 [SMILES: COCc1ccc(CN2CCC(F)(CNC(=O)c3cc(Cl)cc(Cl)c3)CC2)o1] | 429.1 | 3,5-dichloro-N-[(4-fluoro-1-{[5-(methoxymethyl)-2-furyl]methyl}piperidin-4-yl)methyl]benzamide |
| 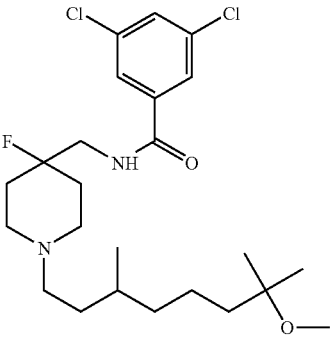 [SMILES: COC(C)(C)CCCC(C)CCN1CCC(F)(CNC(=O)c2cc(Cl)cc(Cl)c2)CC1] | 475.2 | 3,5-dichloro-N-{[4-fluoro-1-(7-methoxy-3,7-dimethyloctyl)piperidin-4-yl]methyl}benzamide |
| 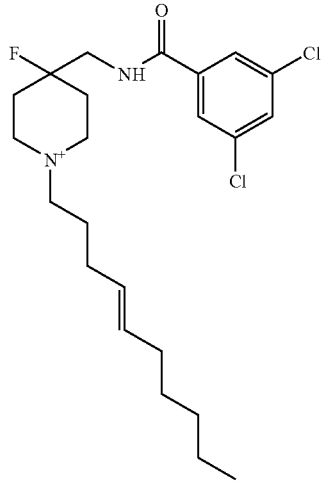 [SMILES: CCCCC/C=C/CCC[NH+]1CCC(F)(CNC(=O)c2cc(Cl)cc(Cl)c2)CC1] | 443.2 | 3,5-dichloro-N-({1-[(4E)-dec-4-en-1-yl]-4-fluoropiperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 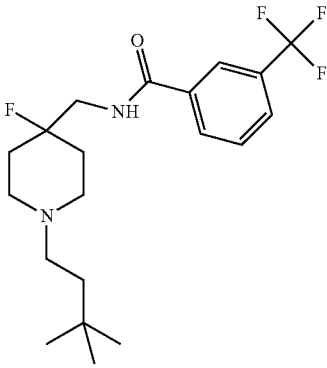 [SMILES: CC(C)(C)CCN1CCC(F)(CNC(=O)c2cccc(C(F)(F)F)c2)CC1] | 389.2 | N-{[1-(3,3-dimethylbutyl)-4-fluoropiperidin-4-yl]methyl}-3-(trifluoromethyl)benzamide |
| 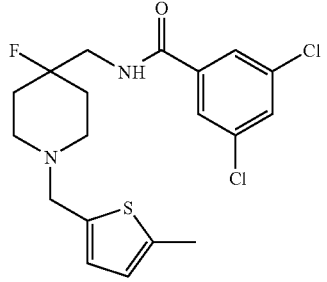 | 415.1 | 3,5-dichloro-N-({4-fluoro-1-[(5-methyl-2-thienyl)methyl]piperidin-4-yl}methyl)-benzamide |
| 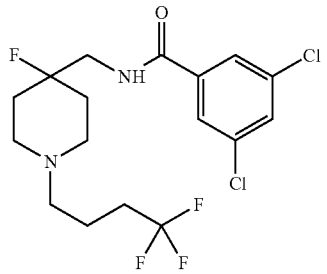 [SMILES: O=C(NCC1(F)CCN(CCCC(F)(F)F)CC1)c1cc(Cl)cc(Cl)c1] | 415.1 | 3,5-dichloro-N-{[4-fluoro-1-(4,4,4-trifluorobutyl)piperidin-4-yl]methyl}benzamide |
| 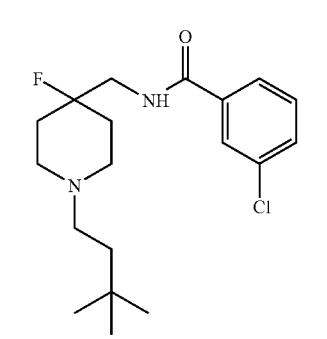 [SMILES: CC(C)(C)CCN1CCC(F)(CNC(=O)c2cccc(Cl)c2)CC1] | 355.2 | 3-chloro-N-{[1-(3,3-dimethylbutyl)-4-fluoropiperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 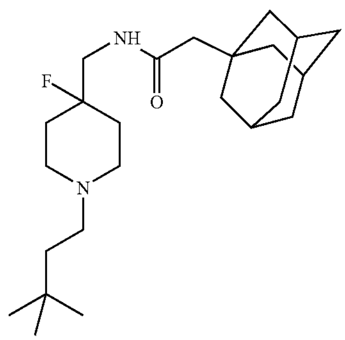 [SMILES: CC(C)(C)CCN1CCC(F)(CNC(=O)CC23CC4CC(CC(C4)C2)C3)CC1] | 393.3 | 2-(1-adamantyl)-N-{[1-(3,3-dimethylbutyl)-4-fluoropiperidin-4-yl]methyl}acetamide |
| 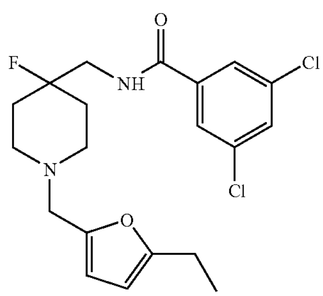 [SMILES: CCc1ccc(CN2CCC(F)(CNC(=O)c3cc(Cl)cc(Cl)c3)CC2)o1] | 413.1 | 3,5-dichloro-N-({1-[(5-ethyl-2-furyl)methyl]-4-fluoropiperidin-4-yl}methyl)benzamide |
| 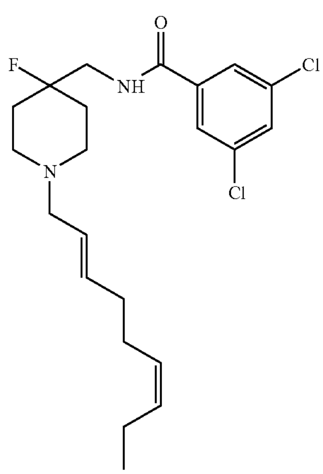 [SMILES: CC/C=C\CC/C=C/CN1CCC(F)(CNC(=O)c2cc(Cl)cc(Cl)c2)CC1] | 427.2 | 3,5-dichloro-N-({4-fluoro-1-(2E,6Z)-nona-2,6-dien-1-yl]piperidin-4-yl}methyl)benzamide |
| 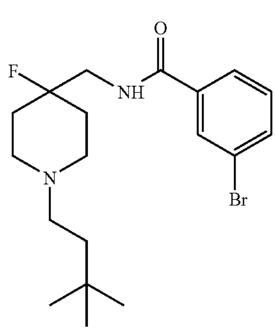 [SMILES: CC(C)(C)CCN1CCC(F)(CNC(=O)c2cccc(Br)c2)CC1] | 399.1 | 3-bromo-N-{[1-(3,3-dimethylbutyl)-4-fluoropiperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| 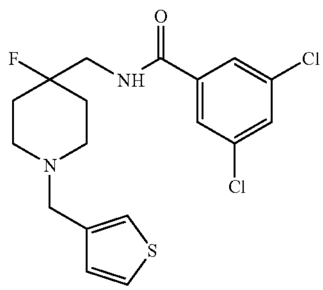 [SMILES: O=C(NCC1(F)CCN(Cc2ccsc2)CC1)c1cc(Cl)cc(Cl)c1] | 401.1 | 3,5-dichloro-N-{[4-fluoro-1-(3-thienylmethyl)piperidin-4-yl]methyl}benzamide |
| | 375.1 | 3,5-dichloro-N-[(4-fluoro-1-pentylpiperidin-4-yl)methyl]benzamide |
| | 375.1 | 3,5-dichloro-N-{[4-fluoro-1-(3-methylbutyl)piperidin-4-yl]methyl}benzamide |
| 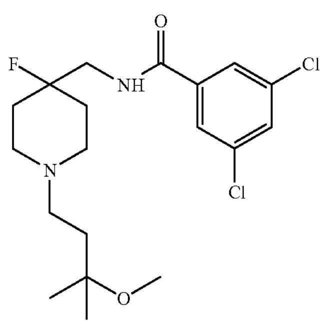 [SMILES: COC(C)(C)CCN1CCC(F)(CNC(=O)c2cc(Cl)cc(Cl)c2)CC1] | 405.2 | 3,5-dichloro-N-{[4-fluoro-1-(3-methoxy-3-methylbutyl)piperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 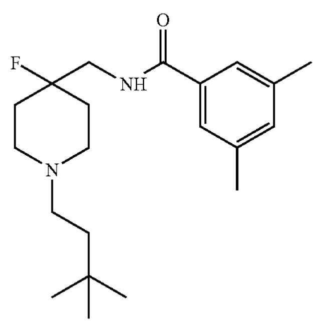 [SMILES: Cc1cc(C)cc(C(=O)NCC2(F)CCN(CCC(C)(C)C)CC2)c1] | 349.3 | N-{[1-(3,3-dimethylbutyl)-4-fluoropiperidin-4-yl]methyl}-3,5-dimethylbenzamide |
| | 387.1 | 3,5-dichloro-N-({1-[(2E)-2-ethylbut-2-en-1-yl]-4-fluoropiperidin-4-yl}methyl)benzamide |
| | 387.1 | 3,5-dichloro-N-({4-fluoro-1-[(2E)-2-methylpent-2-en-1-yl]piperidin-4-yl}methyl)benzamide |
| 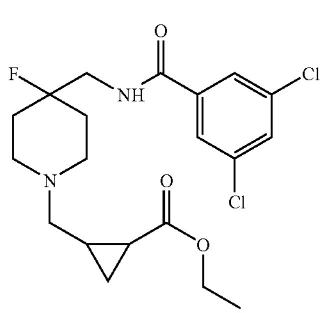 [SMILES: CCOC(=O)C1CC1CN1CCC(F)(CNC(=O)c2cc(Cl)cc(Cl)c2)CC1] | 431.1 | ethyl 2-[(4-{[(3,5-dichlorobenzoyl)-amino]methyl}-4-fluoropiperidin-1-yl)methyl]cyclopropanecarboxylate |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| 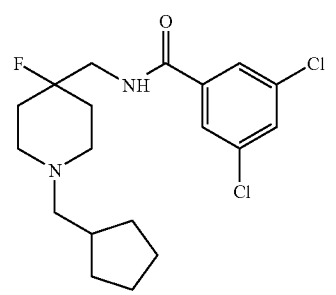 [SMILES: O=C(NCC1(F)CCN(CC2CCCC2)CC1)c1cc(Cl)cc(Cl)c1] | 387.1 | 3,5-dichloro-N-{[1-(cyclopentylmethyl)-4-fluoropiperidin-4-yl]methyl}benzamide |
| 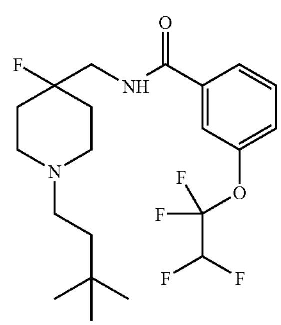 [SMILES: CC(C)(C)CCN1CCC(F)(CNC(=O)c2cccc(OC(F)(F)C(F)F)c2)CC1] | 437.2 | N-{[1-(3,3-dimethylbutyl)-4-fluoropiperidin-4-yl]methyl}-3-(1,1,2,2-tetrafluoro-ethoxy)benzamide |
| 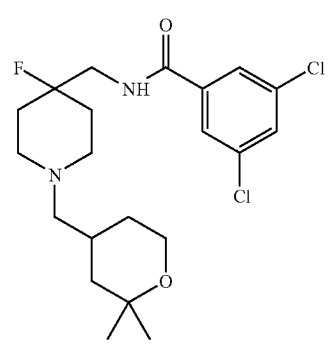 [SMILES: CC1(C)CC(CN2CCC(F)(CNC(=O)c3cc(Cl)cc(Cl)c3)CC2)CCO1] | 431.2 | 3,5-dichloro-N-({1-[(2,2-dimethyltetrahydro-2H-pyran-4-yl)methyl]-4-fluoropiperidin-4-yl}methyl)benzamide |
| 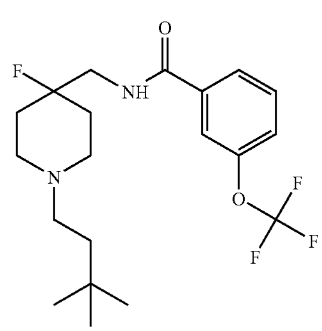 [SMILES: CC(C)(C)CCN1CCC(F)(CNC(=O)c2cccc(OC(F)(F)F)c2)CC1] | 405.2 | N-{[1-(3,3-dimethylbutyl)-4-fluoropiperidin-4-yl]methyl}-3-(trifluoromethoxy)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 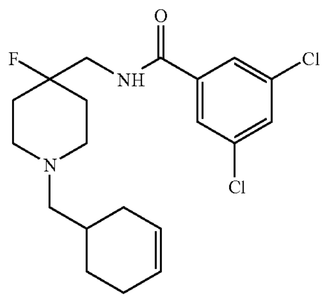 [SMILES: O=C(NCC1(F)CCN(CC2CC=CCC2)CC1)c1cc(Cl)cc(Cl)c1] | 399.1 | 3,5-dichloro-N-{[1-(cyclohex-3-en-1-ylmethyl)-4-fluoropiperidin-4-yl]methyl}benzamide |
| 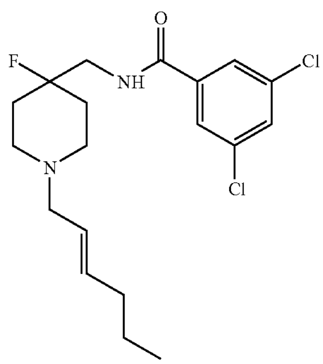 [SMILES: CCC/C=C/CN1CCC(F)(CNC(=O)c2cc(Cl)cc(Cl)c2)CC1] | 387.1 | 3,5-dichloro-N-({4-fluoro-1-[(2E)-hex-2-en-1-yl]piperidin-4-yl}methyl)benzamide |
| 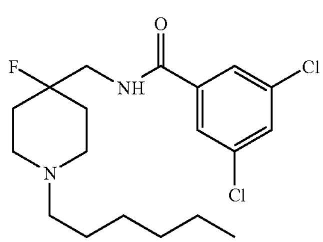 [SMILES: CCCCCCN1CCC(F)(CNC(=O)c2cc(Cl)cc(Cl)c2)CC1] | 389.2 | 3,5-dichloro-N-[(4-fluoro-1-hexylpiperidin-4-yl)methyl]benzamide |
| lp;2p | 369.2 | 3-chloro-N-{[1-(3,3-dimethylbutyl)-4-fluoropiperidin-4-yl]methyl}-5-methylbenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 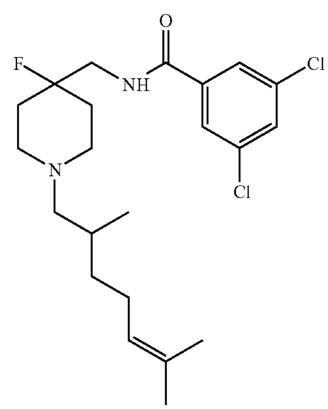 [SMILES: CC(C)=CCCC(C)CN1CCC(F)(CNC(=O)c2cc(Cl)cc(Cl)c2)CC1] | 429.2 | 3,5-dichloro-N-{[1-(2,6-dimethylhept-5-en-1-yl)-4-fluoropiperidin-4-yl]methyl}benzamide |
| 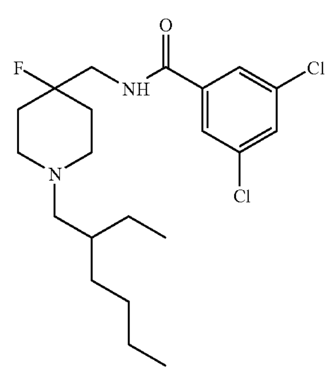 [SMILES: CCCCC(CC)CN1CCC(F)(CNC(=O)c2cc(Cl)cc(Cl)c2)CC1] | 417.2 | 3,5-dichloro-N-{[1-(2-ethylhexyl)-4-fluoropiperidin-4-yl]methyl}benzamide |
| 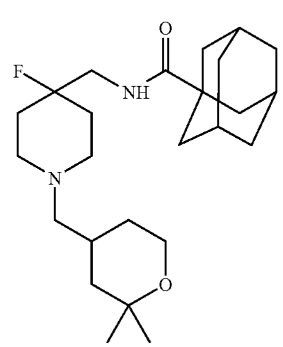 [SMILES: CC1(C)CC(CN2CCC(F)(CNC(=O)C34CC5CC(CC(C5)C3)C4)CC2)CCO1] | 421.4 | N-({1-[(2,2-dimethyltetrahydro-2H-pyran-4-yl)methyl]-4-fluoropiperidin-4-yl}methyl)adamantane-1-carboxamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 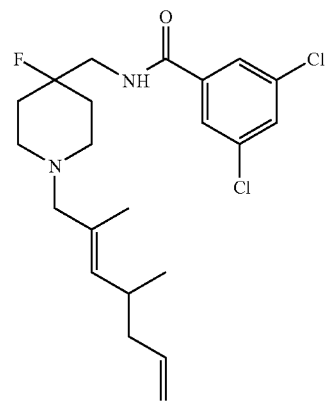 [SMILES: C=CCC(C)/C=C(\C)CN1CCC(F)(CNC(=O)c2cc(Cl)cc(Cl)c2)CC1] | 427.2 | 3,5-dichloro-N-({1-[(2E)-2,4-dimethylhepta-2,6-dien-1-yl]-4-fluoropiperidin-4-yl}methyl)benzamide |
| 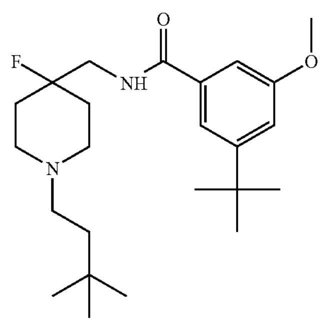 [SMILES: COc1cc(C(=O)NCC2(F)CCN(CCC(C)(C)C)CC2)cc(C(C)(C)C)c1] | 407.3 | 3-tert-butyl-N-{[1-(3,3-dimethylbutyl)-4-fluoropiperidin-4-yl]methyl}-5-methoxybenzamide |
| 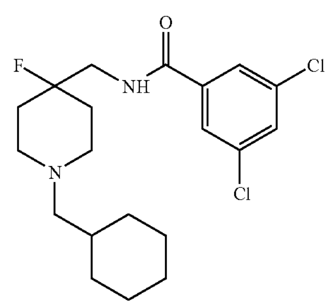 [SMILES: O=C(NCC1(F)CCN(CC2CCCCC2)CC1)c1cc(Cl)cc(Cl)c1] | 401.2 | 3,5-dichloro-N-{[1-(cyclohexylmethyl)-4-fluoropiperidin-4-yl]methyl}benzamide |
| 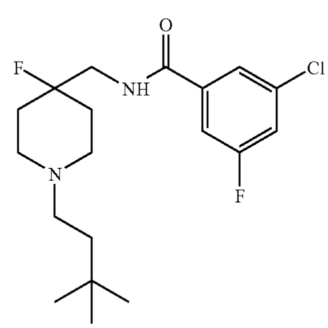 [SMILES: CC(C)(C)CCN1CCC(F)(CNC(=O)c2cc(F)cc(Cl)c2)CC1] | 373.2 | 3-chloro-N-{[1-(3,3-dimethylbutyl)-4-fluoropiperidin-4-yl]methyl}-5-fluorobenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 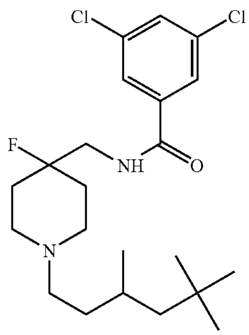 [SMILES: CC(CCN1CCC(F)(CNC(=O)c2cc(Cl)cc(Cl)c2)CC1)CC(C)(C)C] | 431.2 | 3,5-dichloro-N-{[4-fluoro-1-(3,5,5-trimethylhexyl)piperidin-4-yl]methyl}benzamide |
| 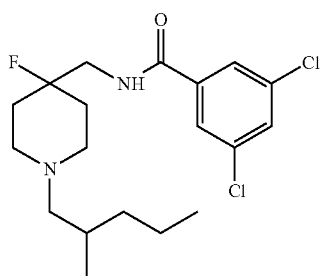 [SMILES: CCCC(C)CN1CCC(F)(CNC(=O)c2cc(Cl)cc(Cl)c2)CC1] | 389.2 | 3,5-dichloro-N-{[4-fluoro-1-(2-methylpentyl)piperidin-4-yl]methyl}benzamide |
| 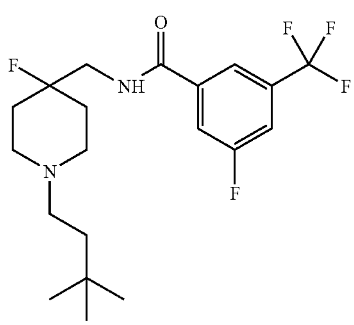 [SMILES: CC(C)(C)CCN1CCC(F)(CNC(=O)c2cc(F)cc(C(F)(F)F)c2)CC1] | 407.2 | N-{[1-(3,3-dimethylbutyl)-4-fluoropiperidin-4-yl]methyl}-3-fluoro-5-(trifluoromethyl)benzamide |
| 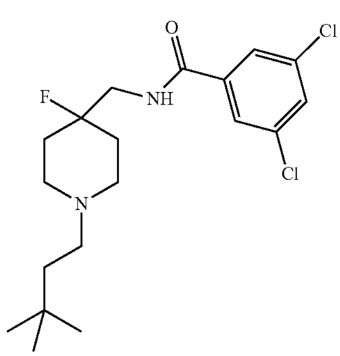 [SMILES: CC(C)(C)CCN1CCC(F)(CNC(=O)c2cc(Cl)cc(Cl)c2)CC1] | 389.1 | 3,5-dichloro-N-{[1-(3,3-dimethylbutyl)-4-fluoropiperidin-4-yl]methyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 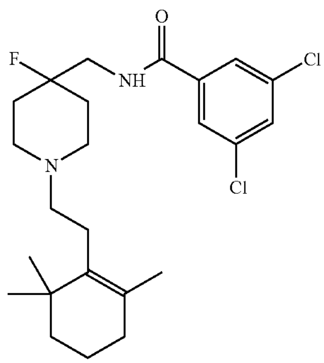 [SMILES: CC1=C(CCN2CCC(F)(CNC(=O)c3cc(Cl)cc(Cl)c3)CC2)C(C)(C)CCC1] | 455.3 | 3,5-dichloro-N-({4-fluoro-1-[2-(2,6,6-trimethylcyclohex-1-en-1-yl)ethyl]piperidin-4-yl}methyl)benzamide |
| 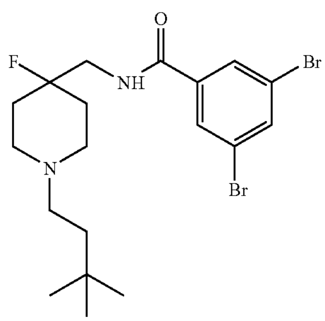 [SMILES: CC(C)(C)CCN1CCC(F)(CNC(=O)c2cc(Br)cc(Br)c2)CC1] | 477.0 | 3,5-dibromo-N-{[1-(3,3-dimethylbutyl)-4-fluoropiperidin-4-yl]methyl}benzamide |
| 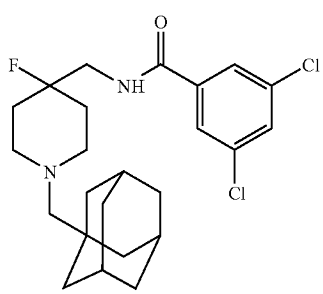 [SMILES: O=C(NCC1(F)CCN(CC23CC4CC(CC(C4)C2)C3)CC1)c1cc(Cl)cc(Cl)c1] | 453.1 | N-{[1-(1-adamantylmethyl)-4-fluoropiperidin-4-yl]methyl}-3,5-dichlorobenzamide |
| 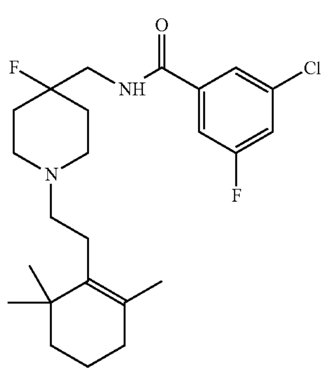 [SMILES: CC1=C(CCN2CCC(F)(CNC(=O)c3cc(F)cc(Cl)c3)CC2)C(C)(C)CCC1] | 439.3 | 3-chloro-5-fluoro-N-({4-fluoro-1-[2-(2,6,6-trimethylcyolohex-1-en-1-yl)ethyl]piperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 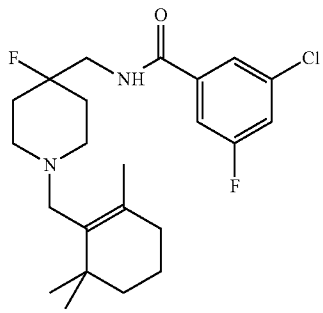 [SMILES: CC1=C(CN2CCC(F)(CNC(=O)c3cc(F)cc(Cl)c3)CC2)C(C)(C)CCC1] | 425.2 | 3-chloro-5-fluoro-N-({4-fluoro-1-[2-(2,6,6-trimethylcyolohex-1-en-1-yl)methyl]-piperidin-4-yl}methyl)benzamide |
| 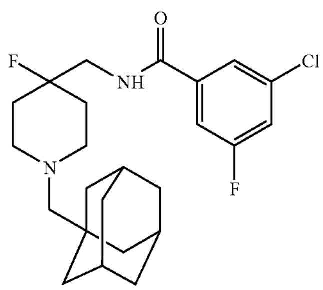 [SMILES: O=C(NCC1(F)CCN(CC23CC4CC(CC(C4)C2)C3)CC1)c1cc(F)cc(Cl)c1] | 437.2 | N-{[1-(1-adamantylmethyl)-4-fluoropiperidin-4-yl]methyl}-3-chloro-5-fluorobenzamide |
| 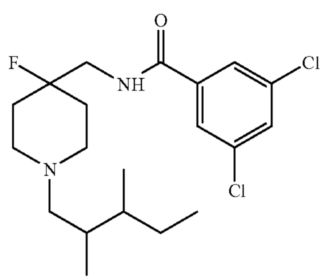 [SMILES: CCC(C)C(C)CN1CCC(F)(CNC(=O)c2cc(Cl)cc(Cl)c2)CC1] | 403.2 | 3,5-dichloro-N-{[1-(2,3-dimethylpentyl)-4-fluoropiperidin-4-yl]methyl}benzamide |
| 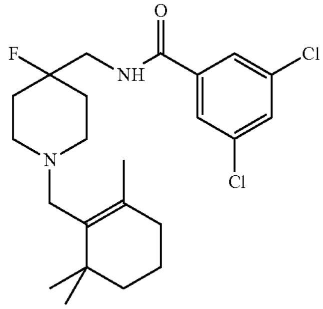 [SMILES: CC1=C(CN2CCC(F)(CNC(=O)c3cc(Cl)cc(Cl)c3)CC2)C(C)(C)CCC1] | 441.2 | 3,5-dichloro-N-({4-fluoro-1-[(2,6,6-trimethylcyclohex-1-en-1-yl)methyl]piperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH⁺) m/z | NAME |
|---|---|---|
| 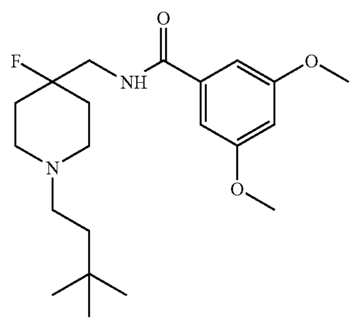 [SMILES: COc1cc(OC)cc(C(=O)NCC2(F)CCN(CCC(C)(C)C)CC2)c1] | 381.3 | N-{[1-(3,3-dimethylbutyl)-4-fluoropiperidin-4-yl]methyl}-3,5-dimethoxybenzamide |
| 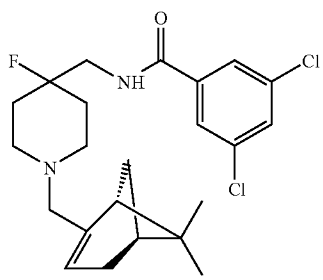 [SMILES: CC1(C)[C@H]2CC=C(CN3CCC(F)(CNC(=O)c4cc(Cl)cc(Cl)c4)CC3)[C@@H]1C2] | 439.2 | 3,5-dichloro-N-(1-{[(1R,5S)-6,6-dimethylbicyclo[3.1.1]hept-2-en-2-yl]methyl}-4-fluoropiperidin-4-yl)methyl]benzamide |
| 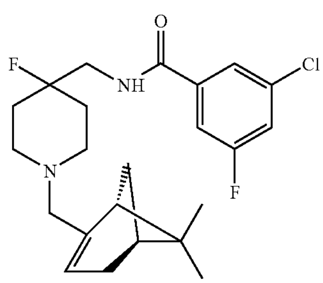 [SMILES: CC1(C)[C@H]2CC=C(CN3CCC(F)(CNC(=O)c4cc(F)cc(Cl)c4)CC3)[C@@H]1C2] | 423.2 | 3-chloro-N-[(1-{[(1R,5S)-6,6-dimethylbicyclo[3.1.1]hept-2-en-2-yl]methyl}-4-fluoropiperidin-4-yl)methyl]-5-fluorobenzamide |
| 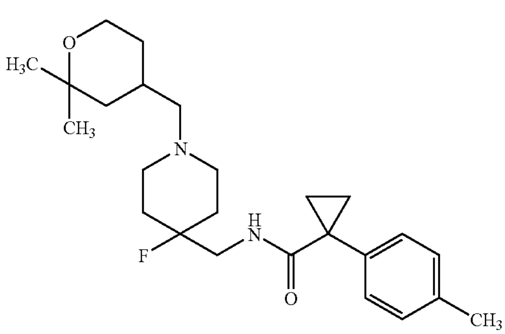 | 417.2 | N-({1-[(2,2-dimethyltetrahydro-2H-pyran-4-yl)methyl]-4-fluoropiperidin-4-yl}methyl)-1-(4-methylphenyl)cyclopropanecarboxamide |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| STRUCTURE | parent ion (MH+) m/z | NAME |
|---|---|---|
| 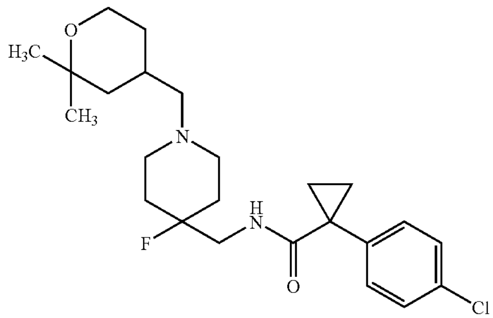 [SMILES: CC1(C)CC(CN2CCC(F)(CNC(=O)C3(c4ccc(Cl)cc4)CC3)CC2)CCO1] | 419.2 | 1-(4-chlorophenyl)-N-({1-[(2,2-dimethyltetrahydro-2H-pyran-4-yl)methyl]-4-fluoropiperidin-4-yl}methyl)cyclopropanecarboxamide |
| 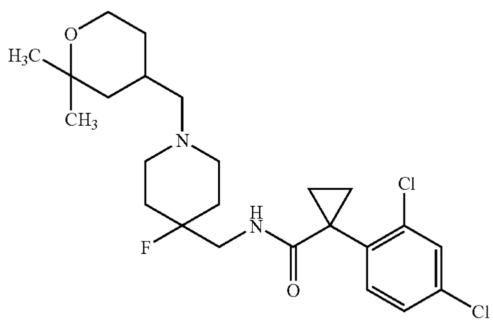 [SMILES: CC1(C)CC(CN2CCC(F)(CNC(=O)C3(c4ccc(Cl)cc4Cl)CC3)CC2)CCO1] | 471.1 | 1-(2,4-dichlorophenyl-N-({1-[(2,2-dimethyltetrahydro-2H-pyran-4-yl)methyl]-4-fluoropiperidin-4-yl}methyl)cyclopropanecarboxamide |
| 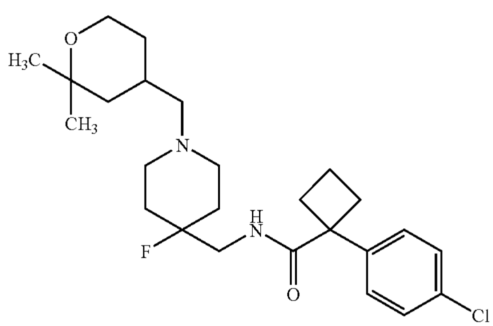 [SMILES: CC1(C)CC(CN2CCC(F)(CNC(=O)C3(c4ccc(Cl)cc4)CCC3)CC2)CCO1] | 451.2 | 1-(4-chlorophenyl)-N-({1-[(2,2-dimethyltetrahydro-2H-pyran-4-yl)methyl]-4-fluoropiperidin-4-yl}methyl)cyclobutanecarboxamide |
| 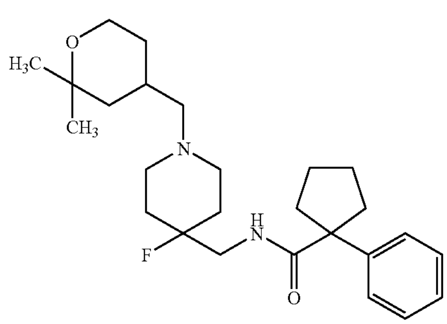 [SMILES: CC1(C)CC(CN2CCC(F)(CNC(=O)C3(c4ccccc4)CCCC3)CC2)CCO1] | 431.3 | N-({1-[(2,2-dimethyltetrahydro-2H-pyran-4-yl)methyl]-4-fluoropiperidin-4-yl}methyl)-1-phenylcyclopentanecarboxamide |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| STRUCTURE | parent ion (MH+) m/z | NAME |
|---|---|---|
| 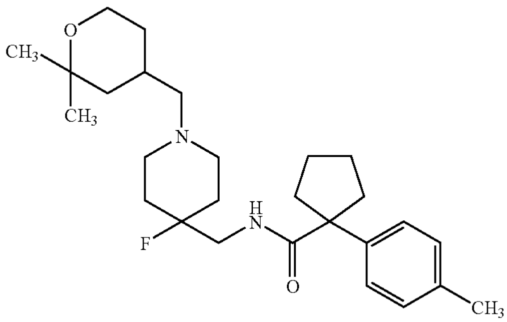 | 445.3 | N-({1-[(2,2-dimethyltetrahydro-2H-pyran-4-yl)methyl]-4-fluoropiperidin-4-yl}methyl)-1-(4-methylphenyl)cyclopentanecarboxamide |
| 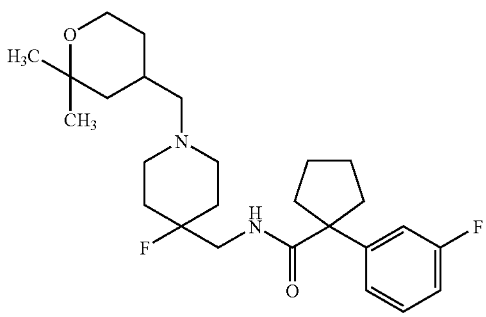 [SMILES: CC1(C)CC(CN2CCC(F)(CNC(=O)C3(c4cccc(F)c4)CCCC3)CC2)CCO1] | 449.2 | N-({1-[(2,2-dimethyltetrahydro-2H-pyran-4-yl)methyl]-4-fluoropiperidin-4-yl}methyl)-1-(3-fluorophenyl)cyclopentanecarboxamide |
| 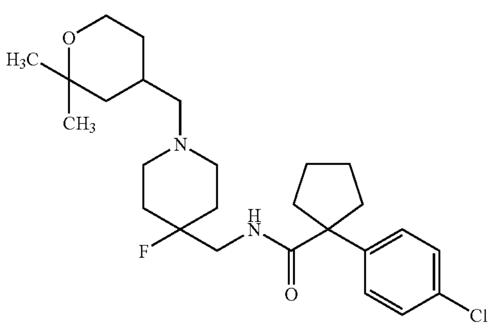 [SMILES: CC1(C)CC(CN2CCC(F)(CNC(=O)C3(c4ccc(Cl)cc4)CCCC3)CC2)CCO1] | 465.2 | 1-(4-chlorophenyl)-N-({1-[(2,2-dimethyltetrahydro-2H-pyran-4-yl)methyl]-4-fluoropiperidin-4-yl}methyl)cyclopentanecarboxamide |
| 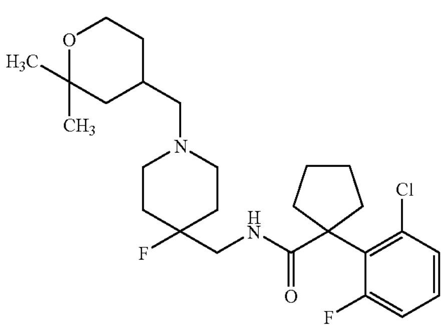 [SMILES: CC1(C)CC(CN2CCC(F)(CNC(=O)C3(c4c(F)cccc4Cl)CCCC3)CC2)CCO1] | 483.2 | 1-(2-chloro-6-fluorophenyl)-N-({1-[(2,2-dimethyltetrahydro-2H-pyran-4-yl)methyl]-4-fluoropiperidin-4-yl}methyl)cyclopentanecarboxamide |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| STRUCTURE | parent ion (MH+) m/z | NAME |
|---|---|---|
| 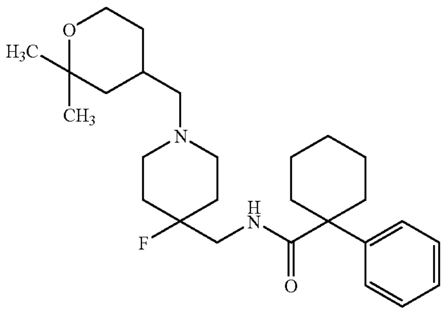 [SMILES: CC1(C)CC(CN2CCC(F)(CNC(=O)C3(c4ccccc4)CCCCC3)CC2)CCO1] | 445.3 | N-({1-[(2,2-dimethyltetrahydro-2H-pyran-4-yl)methyl]-4-fluoropiperidin-4-yl}methyl)-1-phenylcyclohexanecarboxamide |
| 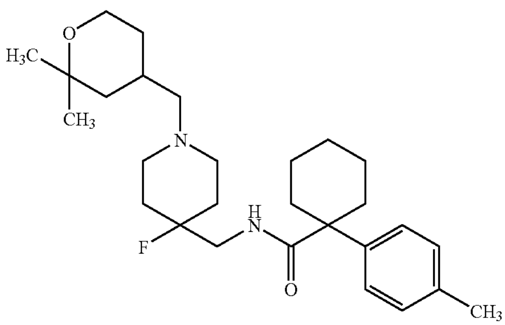 | 459.3 | N-({1-[(2,2-dimethyltetrahydro-2H-pyran-4-yl)methyl]-4-fluoropiperidin-4-yl}methyl)-1-(4-methylphenyl)cyclohexanecarboxamide |
| 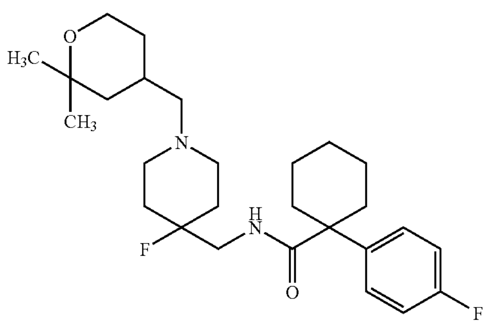 [SMILES: CC1(C)CC(CN2CCC(F)(CNC(=O)C3(c4ccc(F)cc4)CCCCC3)CC2)CCO1] | 463.3 | N-({1-[(2,2-dimethyltetrahydro-2H-pyran-4-yl)methyl]-4-fluoropiperidin-4-yl}methyl)-1-(4-fluorophenyl)cyclohexanecarboxamide |
| 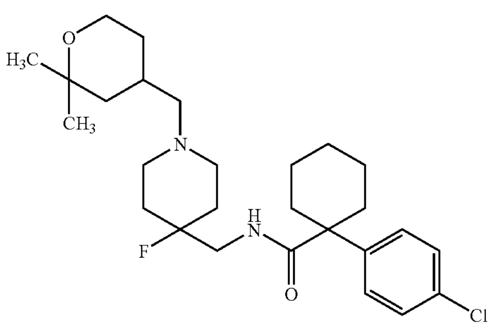 [SMILES: CC1(C)CC(CN2CCC(F)(CNC(=O)C3(c4ccc(Cl)cc4)CCCCC3)CC2)CCO1] | 479.2 | 1-(4-chlorophenyl)-N-({1-[(2,2-dimethyltetrahydro-2H-pyran-4-yl)methyl]-4-fluoropiperidin-4-yl}methyl)cyclohexanecarboxamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| | 497.2 | 1-(2-chloro-4-fluorophenyl)-N-({1-[(2,2-dimethyltetrahydro-2H-pyran-4-yl)methyl]-4-fluoropiperidin-4-yl}methyl)cyclohexanecarboxamide |
| | 497.2 | 1-(2-chloro-6-fluorophenyl)-N-({1-[(2,2-dimethyltetrahydro-2H-pyran-4-yl)methyl]-4-fluoropiperidin-4-yl}methyl)cyclohexanecarboxamide |
| 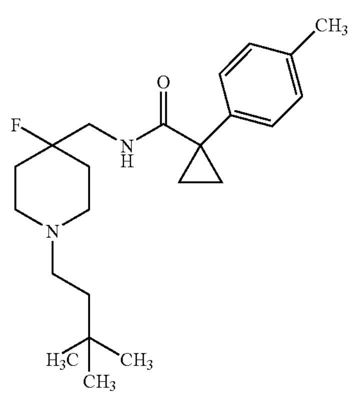 [SMILES: Cc1ccc(C2(C(=O)NCC3(F)CCN(CCC(C)(C)C)CC3)CC2)cc1] | 375.2 | N-{[1-(3,3-dimethylbutyl)-4-fluoropiperidin-4-yl]methyl}-1-(4-methylphenyl)cyclopropanecarboxamide |
| 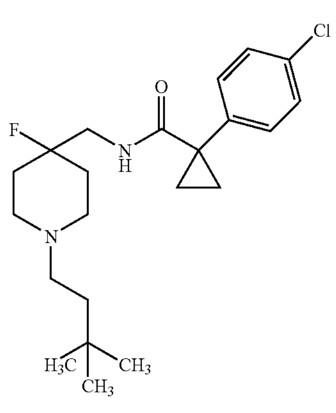 [SMILES: CC(C)(C)CCN1CCC(F)(CNC(=O)C2(c3ccc(Cl)cc3)CC2)CC1] | 395.2 | 1-(4-chlorophenyl)-N-{[1-(3,3-dimethylbutyl)-4-fluoropiperidin-4-yl]methyl}cyclopropanecarboxamide |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| STRUCTURE | parent ion (MH$^+$) m/z | NAME |
|---|---|---|
| 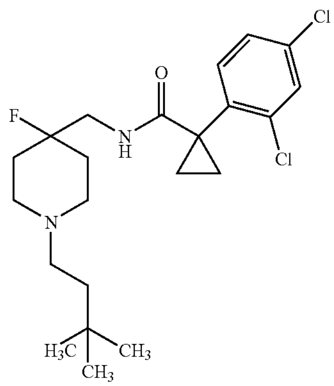 [SMILES: CC(C)(C)CCN1CCC(F)(CNC(=O)C2(c3ccc(Cl)cc3Cl)CC2)CC1] | 429.1 | 1-(2,4-dichlorophenyl)-N-{[1-(3,3-dimethylbutyl)-4-fluoropiperidin-4-yl]methyl}cyclopropanecarboxamide |
| 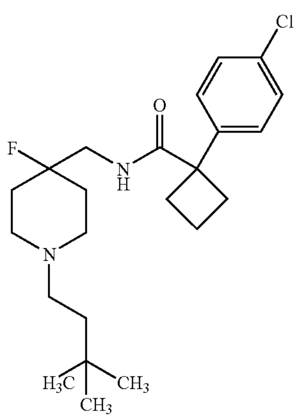 [SMILES: CC(C)(C)CCN1CCC(F)(CNC(=O)C2(c3ccc(Cl)cc3)CCC2)CC1] | 409.2 | 1-(4-chlorophenyl)-N-{[1-(3,3-dimethylbutyl)-4-fluoropiperidin-4-yl]methyl}cyclobutanecarboxamide |
| 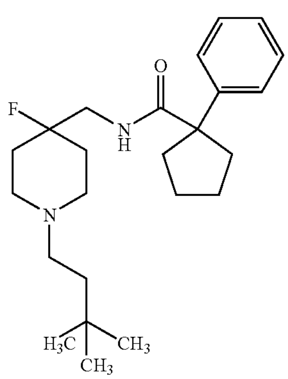 [SMILES: CC(C)(C)CCN1CCC(F)(CNC(=O)C2(c3ccccc3)CCCC2)CC1] | 389.2 | N-{[1-(3,3-dimethylbutyl)-4-fluoropiperidin-4-yl]methyl}-1-phenylcyclopentanecarboxamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 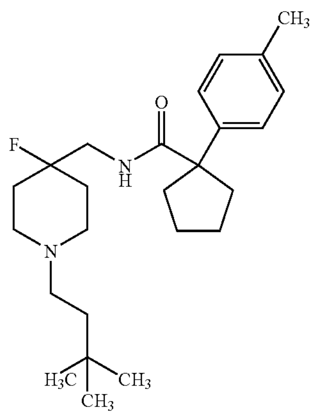 [SMILES: Cc1ccc(C2(C(=O)NCC3(F)CCN(CCC(C)(C)C)CC3)CCCC2)cc1] | 403.3 | N-{[1-(3,3-dimethylbutyl)-4-fluoropiperidin-4-yl]methyl}-1-(4-methylphenyl)cyclopentanecarboxamide |
| 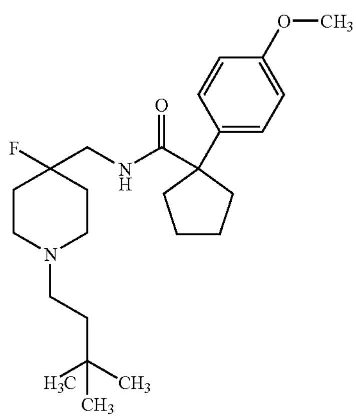 [SMILES: COc1ccc(C2(C(=O)NCC3(F)CCN(CCC(C)(C)C)CC3)CCCC2)cc1] | 419.3 | N-{[1-(3,3-dimethylbutyl)-4-fluoropiperidin-4-yl]methyl}-1-(4-methoxyphenyl)cyclopentanecarboxamide |
| 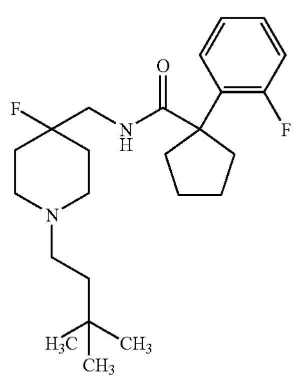 [SMILES: CC(C)(C)CCN1CCC(F)(CNC(=O)C2(c3ccccc3F)CCCC2)CC1] | 407.2 | N-{[1-(3,3-dimethylbutyl)-4-fluoropiperidin-4-yl]methyl}-1-(2-fluorophenyl)cyclopentanecarboxamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 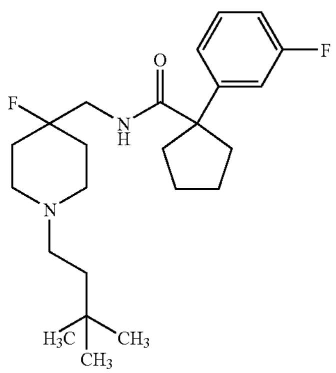 [SMILES: CC(C)(C)CCN1CCC(F)(CNC(=O)C2(c3cccc(F)c3)CCCC2)CC1] | 407.2 | N-{[1-(3,3-dimethylbutyl)-4-fluoropiperidin-4-yl]methyl}-1-(3-fluorophenyl)cyclopentanecarboxamide |
| 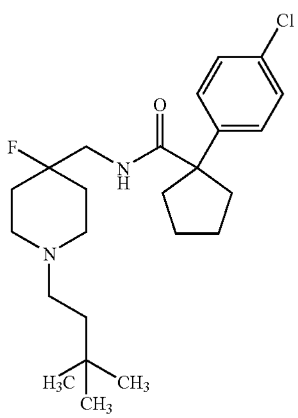 [SMILES: CC(C)(C)CCN1CCC(F)(CNC(=O)C2(c3ccc(Cl)cc3)CCCC2)CC1] | 423.2 | 1-(4-chlorophenyl)-N-{[1-(3,3-dimethylbutyl)-4-fluoropiperidin-4-yl]methyl}cyclopentanecarboxamide |
| 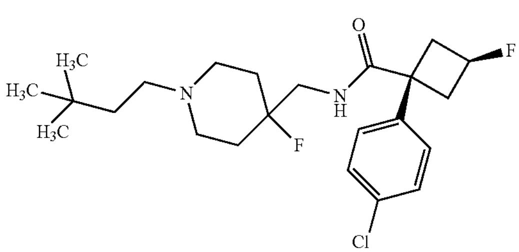 [SMILES: CC(C)(C)CCN1CCC(F)(CNC(=O)[C@]2(c3ccc(Cl)cc3)C[C@@H](F)C2)CC1] | 427.2 | trans-1-(4-chlorophenyl)-N-{[1-(3,3-dimethylbutyl)-4-fluoropiperidin-4-yl]methyl}-3-fluorocyclobutanecarboxamide |
| 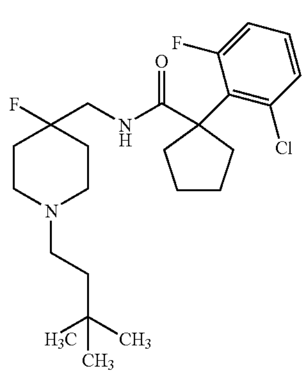 [SMILES: CC(C)(C)CCN1CCC(F)(CNC(=O)C2(c3c(F)cccc3Cl)CCCC2)CC1] | 441.2 | 1-(2-chloro-6-fluorophenyl)-N-{[1-(3,3-dimethylbutyl)-4-fluoropiperidin-4-yl]methyl}cyclopentanecarboxamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 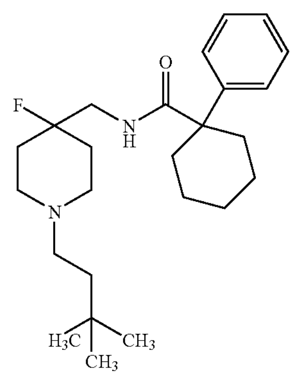 [SMILES: CC(C)(C)CCN1CCC(F)(CNC(=O)C2(c3ccccc3)CCCCC2)CC1] | 403.3 | N-{[1-(3,3-dimethylbutyl)-4-fluoropiperidin-4-yl]methyl}-1-phenylcyclohexanecarboxamide |
| 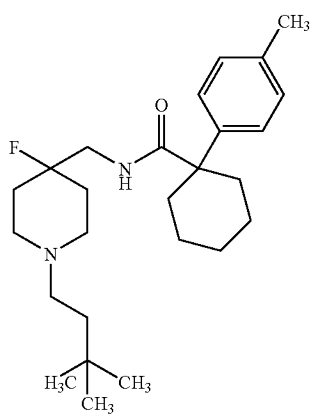 [SMILES: Cc1ccc(C2(C(=O)NCC3(F)CCN(CCC(C)(C)C)CC3)CCCCC2)cc1] | 417.3 | N-{[1-(3,3-dimethylbutyl)-4-fluoropiperidin-4-yl]methyl}-1-(4-methylphenyl)cyclohexanecarboxamide |
| 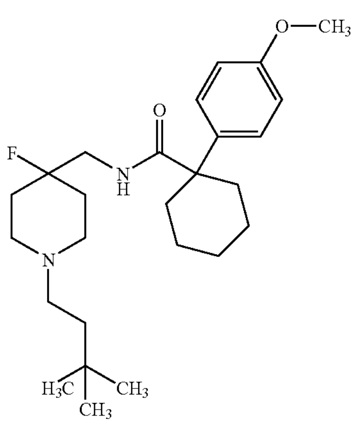 [SMILES: COc1ccc(C2(C(=O)NCC3(F)CCN(CCC(C)(C)C)CC3)CCCCC2)cc1] | 433.3 | N-{[1-(3,3-dimethylbutyl)-4-fluoropiperidin-4-yl]methyl}-1-(4-methoxyphenyl)cyclohexanecarboxamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
|  | 421.3 | N-{[1-(3,3-dimethylbutyl)-4-fluoropiperidin-4-yl]methyl}-1-(2-fluorophenyl)cyclohexanecarboxamide |
|  | 421.3 | N-{[1-(3,3-dimethylbutyl)-4-fluoropiperidin-4-yl]methyl}-1-(4-fluorophenyl)cyclohexanecarboxamide |
| 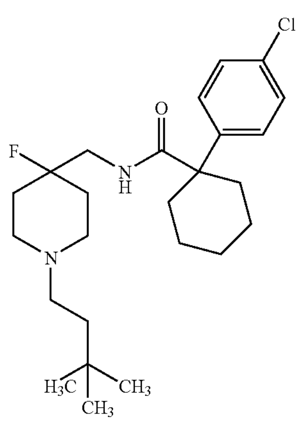 [SMILES: CC(C)(C)CCN1CCC(F)(CNC(=O)C2(c3ccc(Cl)cc3)CCCCC2)CC1] | 437.2 | 1-(4-chlorophenyl)-N-{[1-(3,3-dimethylbutyl)-4-fluoropiperidin-4-yl]methyl}cyclohexanecarboxamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
|  | 455.2 | 1-(2-chloro-4-fluorophenyl)-N-{[1-(3,3-dimethylbutyl)-4-fluoropiperidin-4-yl]methyl}cyclohexanecarboxamide |
|  | 455.2 | 1-(2-chloro-6-fluorophenyl)-N-{[1-(3,3-dimethylbutyl)-4-fluoropiperidin-4-yl]methyl}cyclohexanecarboxamide |
| 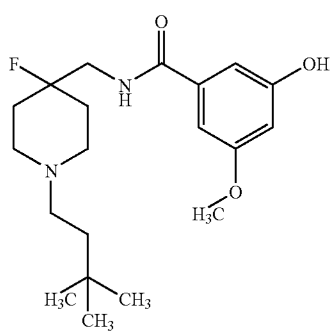 [SMILES: COc1cc(O)cc(C(=O)NCC2(F)CCN(CCC(C)(C)C)CC2)c1] | 367.3 | N-{[1-(3,3-dimethylbutyl)-4-fluoropiperidin-4-yl]methyl}-3-hydroxy-5-methoxybenzamide |
| 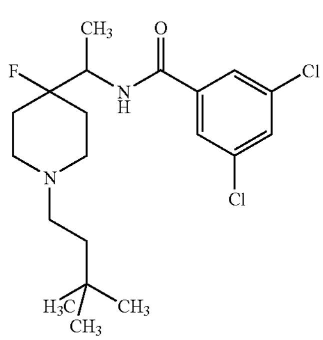 [SMILES: CC(NC(=O)c1cc(Cl)cc(Cl)c1)C1(F)CCN(CCC(C)(C)C)CC1] | 403.1 | 3,5-dichloro-N-{1-[1-(3,3-dimethylbutyl)-4-fluoropiperidin-4-yl]ethyl}benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 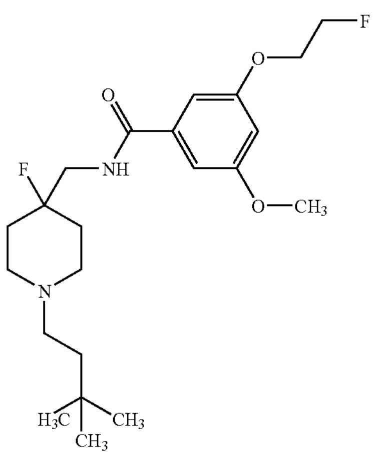 [SMILES: COc1cc(OCCF)cc(C(=O)NCC2(F)CCN(CCC(C)(C)C)CC2)c1] | 413.3 | N-{[1-(3,3-dimethylbutyl)-4-fluoropiperidin-4-yl]methyl}-3-(2-fluoroethoxy)-5-methoxybenzamide |
| 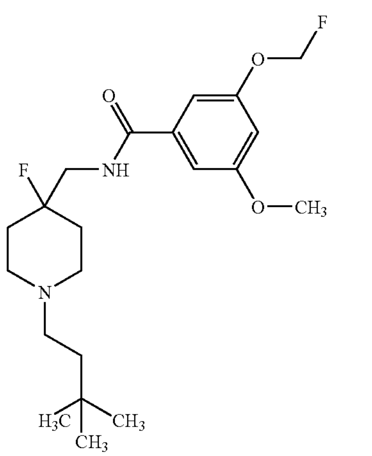 [SMILES: COc1cc(OCF)cc(C(=O)NCC2(F)CCN(CCC(C)(C)C)CC2)c1] | 399.2 | N-{[1-(3,3-dimethylbutyl)-4-fluoropiperidin-4-yl]methyl}-3-(fluoromethoxy)-5-methoxybenzamide |
| 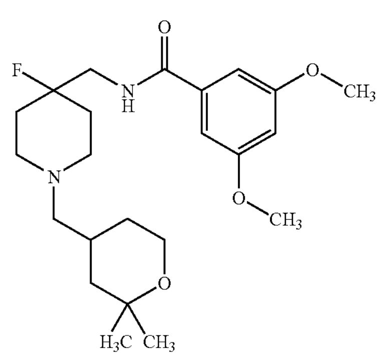 [SMILES: COc1cc(OC)cc(C(=O)NCC2(F)CCN(CC3CCOC(C)(C)C3)CC2)c1] | 423.2 | N-({1-[(2,2-dimethyltetrahydro-2H-pyran-4-yl)methyl]-4-fluoropiperidin-4-yl}methyl)-3,5-dimethoxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 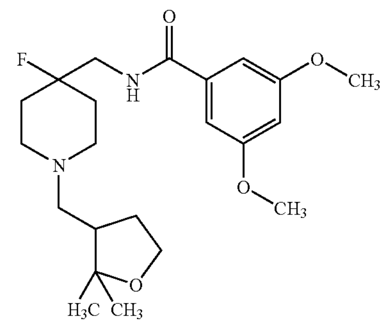 [SMILES: COc1cc(OC)cc(C(=O)NCC2(F)CCN(CC3CCOC3(C)C)CC2)c1] | 409.2 | N-({1-[(2,2-dimethyltetrahydrofuran-3-yl)methyl]-4-fluoropiperidin-4-yl}methyl)-3,5-dimethoxybenzamide |
| | 385.2 | 3-chloro-N-{[1-(3,3-dimethylbutyl)-4-fluoropiperidin-4-yl]methyl}-4-methoxybenzamide |
| | 385.2 | 4-chloro-N-{[1-(3,3-dimethylbutyl)-4-fluoropiperidin-4-yl]methyl}-2-methoxybenzamide |
| 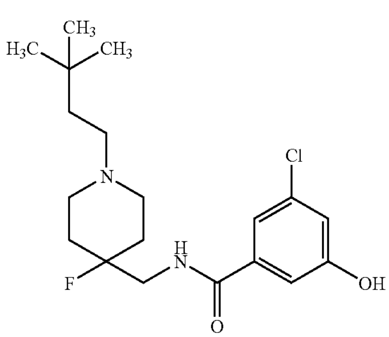 [SMILES: CC(C)(C)CCN1CCC(F)(CNC(=O)c2cc(O)cc(Cl)c2)CC1] | 371.1 | 3-chloro-N-{[1-(3,3-dimethylbutyl)-4-fluoropiperidin-4-yl]methyl}-5-hydroxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 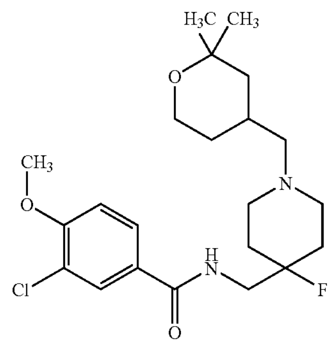 [SMILES: COc1ccc(C(=O)NCC2(F)CCN(CC3CCOC(C)(C)C3)CC2)cc1Cl] | 427.2 | 3-chloro-N-({1-[(2,2-dimethyltetrahydro-2H-pyran-4-yl)methyl]-4-fluoropiperidin-4-yl}methyl)-4-methoxybenzamide |
| 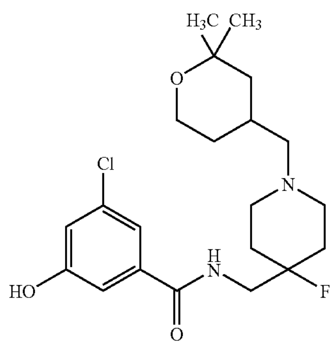 [SMILES: CC1(C)CC(CN2CCC(F)(CNC(=O)c3cc(O)cc(Cl)c3)CC2)CCO1] | 413.1 | 3-chloro-N-({1-[(2,2-dimethyltetrahydro-2H-pyran-4-yl)methyl]-4-fluoropiperidin-4-yl}methyl)-5-hydroxybenzamide |
| 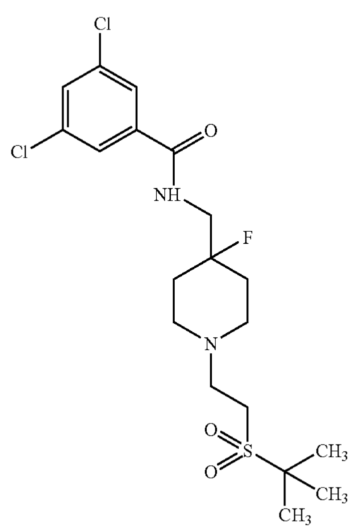 [SMILES: CC(C)(C)S(=O)(=O)CCN1CCC(F)(CNC(=O)c2cc(Cl)cc(Cl)c2)CC1] | 453.1 | N-({1-[2-tert-butylsulfonyl)ethyl]-4-fluoropiperidin-4-yl}methyl)-3,5-dichlorobenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| | | 3,5-dichloro-N-[(4-fluoro-1-{2-oxo-2-[2-(trifluoromethyl)pyrrolidin-1-yl]ethyl}piperidin-4-yl)methyl]benzamide |
| | | 3,5-dichloro-N-({1-[2-(4,4-dimethyl-1,3-oxazolidin-3-yl)-2-oxoethyl]-4-fluoropiperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| | | N-[(1-{2-[tert-butyl(2-methoxyethyl)amino]-2-oxoethyl}-4-fluoropiperidin-4-yl)methyl]-3,5-dichlorobenzamide |
| 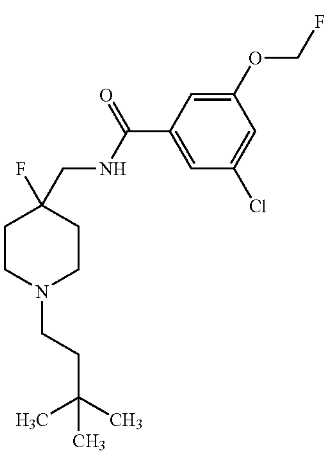 [SMILES: CC(C)(C)CCN1CCC(F)(CNC(=O)c2cc(Cl)cc(OCF)c2)CC1] | 403.1 | 3-chloro-N-{[1-(3,3-dimethylbutyl)-4-fluoropiperidin-4-yl]methyl}-5-(fluoromethoxy)benzamide |
| 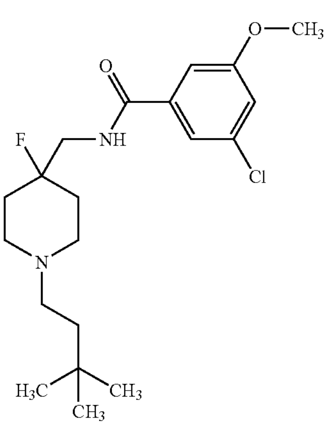 [SMILES: COc1cc(Cl)cc(C(=O)NCC2(F)CCN(CCC(C)(C)C)CC2)c1] | 385.2 | 3-chloro-N-{[1-(3,3-dimethylbutyl)-4-fluoropiperidin-4-yl]methyl}-5-methoxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| 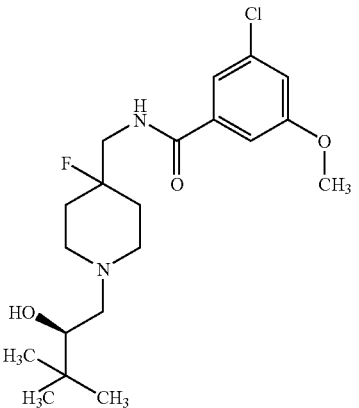 [SMILES: COc1cc(Cl)cc(C(=O)NCC2(F)CCN(C[C@H](O)C(C)(C)C)CC2)c1] | 401.1 | 3-chloro-N-({4-fluoro-1-[(2R)-2-hydroxy-3,3-dimethylbutyl]piperidin-4-yl}methyl)-5-methoxybenzamide |
| 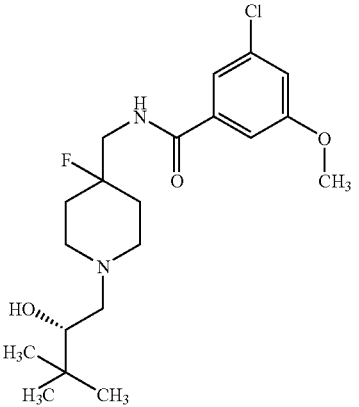 [SMILES: COc1cc(Cl)cc(C(=O)NCC2(F)CCN(C[C@@H](O)C(C)(C)C)CC2)c1] | 401.2 | 3-chloro-N-({4-fluoro-1-[(2S)-2-hydroxy-3,3-dimethylbutyl]piperidin-4-yl}methyl)-5-methoxybenzamide |
| 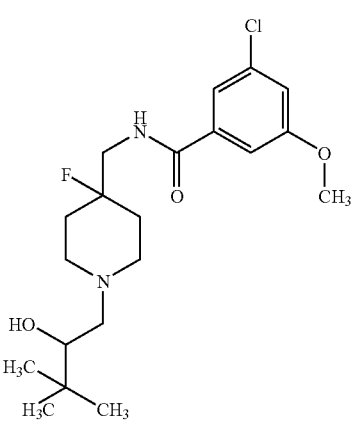 [SMILES: COc1cc(Cl)cc(C(=O)NCC2(F)CCN(CC(O)C(C)(C)C)CC2)c1] | 401.1 | 3-chloro-N-{[4-fluoro-1-(2-hydroxy-3,3-dimethylbutyl)piperidin-4-yl]methyl}-5-methoxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| 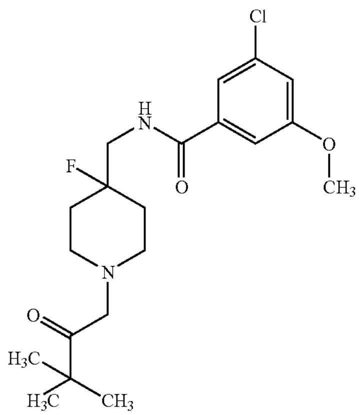 [SMILES: COc1cc(Cl)cc(C(=O)NCC2(F)CCN(CC(=O)C(C)(C)C)CC2)c1] | 399.1 | 3-chloro-N-{[1-(3,3-dimethyl-2-oxobutyl)-4-fluoropiperidin-4-yl]methyl}-5-methoxybenzamide |
|  | 405.1 | 3,5-dichloro-N-({4-fluoro-1-[(2R)-2-hydroxy-3,3-dimethylbutyl]piperidin-4-yl}methyl)benzamide |
|  | 405.1 | 3,5-dichloro-N-({4-fluoro-1-[(2S)-2-hydroxy-3,3-dimethylbutyl]piperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
| --- | --- | --- |
| 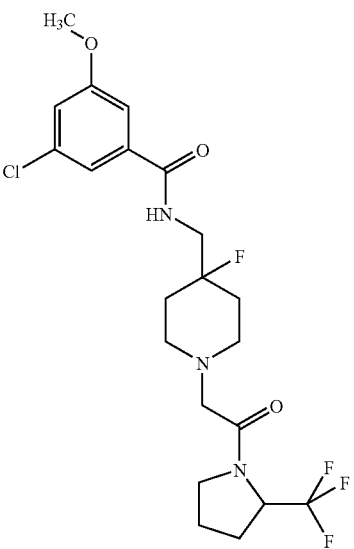 [SMILES: COc1cc(Cl)cc(C(=O)NCC2(F)CCN(CC(=O)N3CCCC3C(F)(F)F)CC2)c1] | 480.1 | 3-chloro-N-[(4-fluoro-1-{2-oxo-2-[2-(trifluoromethyl)pyrrolidin-1-yl]ethyl}piperidin-4-yl)methyl]-5-methoxybenzamide |
| 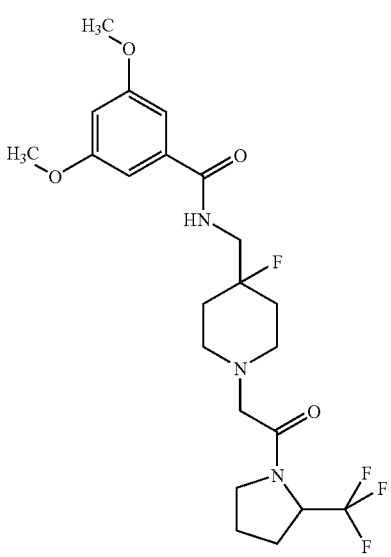 [SMILES: COc1cc(OC)cc(C(=O)NCC2(F)CCN(CC(=O)N3CCCC3C(F)(F)F)CC2)c1] | 476.2 | N-[(4-fluoro-1-{2-oxo-2-[2-(trifluoromethyl)pyrrolidin-1-yl]ethyl}piperidin-4-yl)methyl]-3,5-dimethoxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| 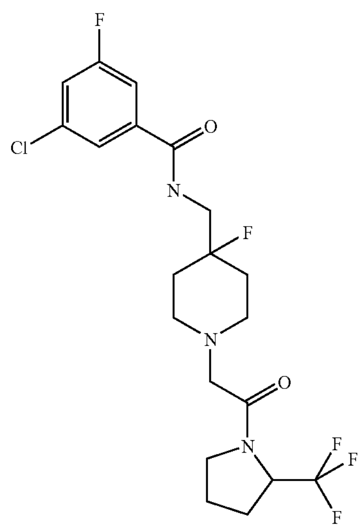 [SMILES: O=C(NCC1(F)CCN(CC(=O)N2CCCC2C(F)(F)F)CC1)c1cc(F)cc(Cl)c1] | 468.1 | 3-chloro-5-fluoro-N-[(4-fluoro-1-{2-oxo-2-[2-(trifluoromethyl)pyrrolidin-1-yl]ethyl}piperidin-4-yl)methyl]benzamide |
| 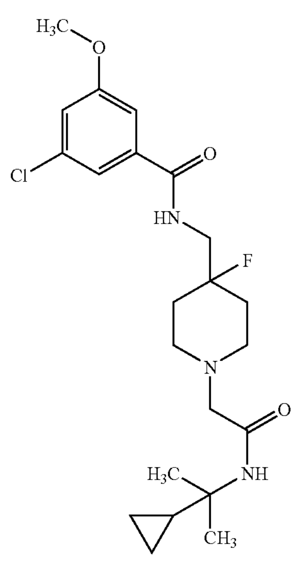 [SMILES: COc1cc(Cl)cc(C(=O)NCC2(F)CCN(CC(=O)NC(C)(C)C3CC3)CC2)c1] | 440.1 | 3-chloro-N-[(1-{2-[(1-cyclopropyl-1-methylethyl)amino]-2-oxoethyl}-4-fluoropiperidin-4-yl)methyl]-5-methoxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 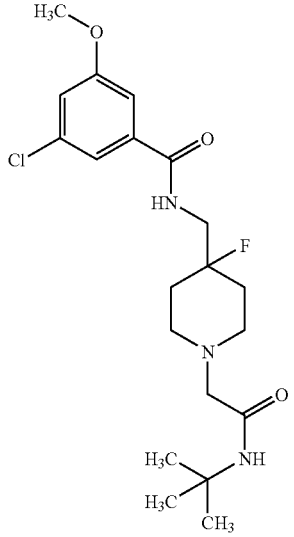 [SMILES: COc1cc(Cl)cc(C(=O)NCC2(F)CCN(CC(=O)NC(C)(C)C)CC2)c1] | 414.1 | N-({1-[2-(tert-butylamino)-2-oxoethyl]-4-fluoropiperidin-4-yl}methyl)-3-chloro-5-methoxybenzamide |
| 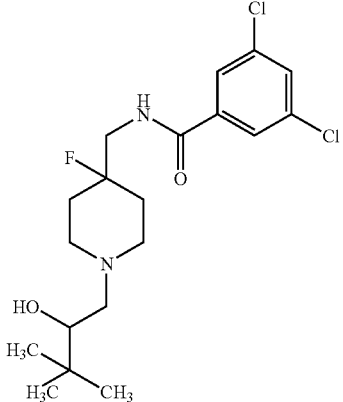 [SMILES: CC(C)(C)C(O)CN1CCC(F)(CNC(=O)c2cc(Cl)cc(Cl)c2)CC1] | 405.1 | 3,5-dichloro-N-{[4-fluoro-1-(2-hydroxy-3,3-dimethylbutyl)piperidin-4-yl]methyl}benzamide |
| 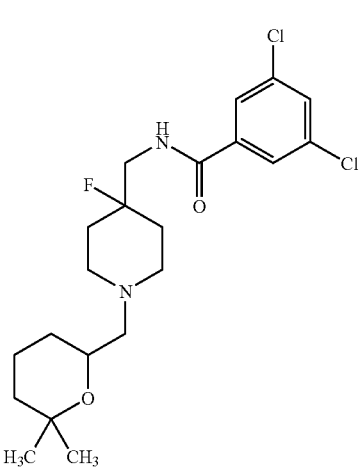 [SMILES: CC1(C)CCCC(CN2CCC(F)(CNC(=O)c3cc(Cl)cc(Cl)c3)CC2)O1] | 431.1 | 3,5-dichloro-N-({1-[(6,6-dimethyltetrahydro-2H-pyran-2-yl)methyl]-4-fluoropiperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
|---|---|---|
| 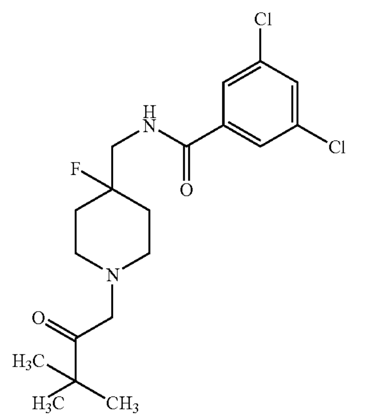 [SMILES: CC(C)(C)C(=O)CN1CCC(F)(CNC(=O)c2cc(Cl)cc(Cl)c2)CC1] | 403.1 | 3,5-dichloro-N-{(1-(3,3-dimethyl-2-oxobutyl)-4-fluoropiperidin-4-yl]methyl}benzamide |
| 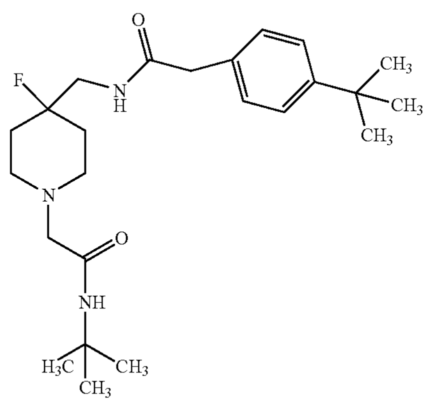 [SMILES: CC(C)(C)NC(=O)CN1CCC(F)(CNC(=O)Cc2ccc(C(C)(C)C)cc2)CC1] | 420.2 | N-({1-[2-(tert-butylamino)-2-oxoethyl]-4-fluoropiperidin-4-yl}methyl)-2-(4-tert-butylphenyl)acetamide |
| 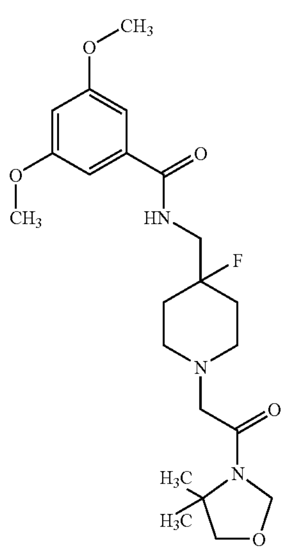 [SMILES: COc1cc(OC)cc(C(=O)NCC2(F)CCN(CC(=O)N3COCC3(C)C)CC2)c1] | 438.3 | N-({1-[2-(4,4-dimethyl-1,3-oxazolidin-3-yl)-2-oxoethyl]-4-fluoropiperidin-4-yl}methyl)-3,5-dimethoxybenzamide |

TABLE 1-continued

*The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.*

| STRUCTURE | parent ion (MH+) m/z | NAME |
|---|---|---|
| 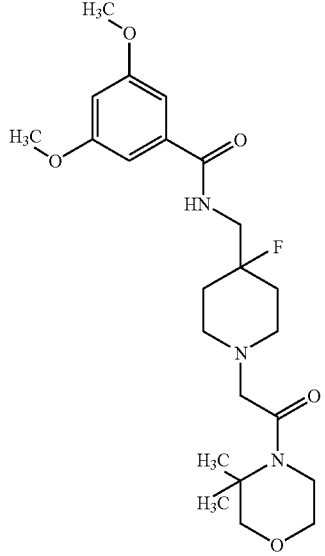 [SMILES: COc1cc(OC)cc(C(=O)NCC2(F)CCN(CC(=O)N3CCOCC3(C)C)CC2)c1] | 452.2 | N-({1-[2-(3,3-dimethylmorpholin-4-yl)-2-oxoethyl]-4-fluoropiperidin-4-yl}methyl)-3,5-dimethoxybenzamide |
| 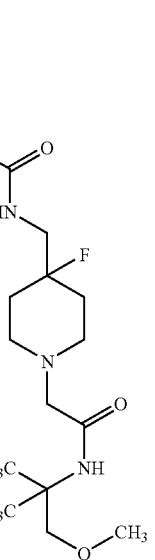 | 440.2 | N-[(4-fluoro-1-{2-[(2-methoxy-1,1-dimethylethyl)amino]-2-oxoethyl}piperidin-4-yl)methyl]-3,5-dimethoxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 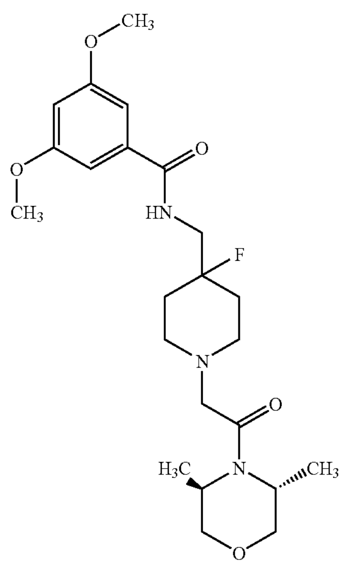 [SMILES: COc1cc(OC)cc(C(=O)NCC2(F)CCN(CC(=O)N3[C@H](C)COC[C@H]3C)CC2)c1] | 452.2 | N-[(1-{2-[(3R,5R)-3,5-dimethylmorpholin-4-yl]-2-oxoethyl}-4-fluoropiperidin-4-yl)methyl]-3,5-dimethoxybenzamide |
| 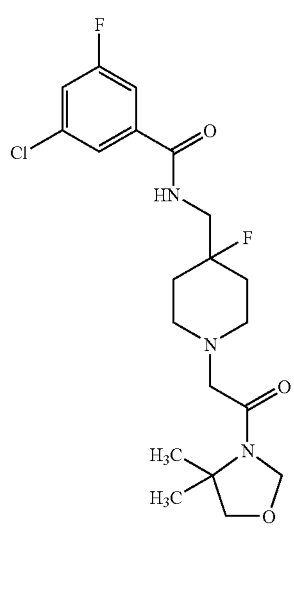 [SMILES: CC1(C)COCN1C(=O)CN1CCC(F)(CNC(=O)c2cc(F)cc(Cl)c2)CC1] | 430.1 | 3-chloro-N-({1-[2-(4,4-dimethyl-1,3-oxazolidin-3-yl)-2-oxoethyl]-4-fluoropiperidin-4-yl}methyl)-5-fluorobenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 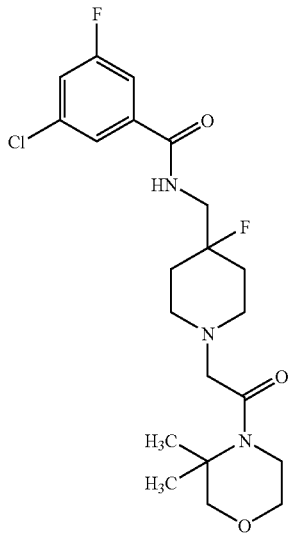 [SMILES: CC1(C)COCCN1C(=O)CN1CCC(F)(CNC(=O)c2cc(F)cc(Cl)c2)CC1] | 444.1 | 3-chloro-N-({1-[2-(3,3-dimethylmorpholin-4-yl)-2-oxoethyl]-4-fluoropiperidin-4-yl}methyl)-5-fluorobenzamide |
| 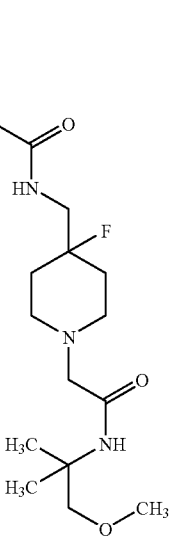 | 432.1 | 3-chloro-5-fluoro-N-[(4-fluoro-1-{2-[(2-methoxy-1,1-dimethylethyl)amino]-2-oxoethyl}piperidin-4-yl)methyl]benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 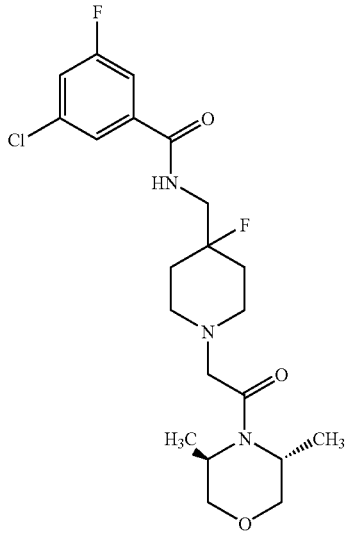 [SMILES: C[C@@H]1COC[C@@H](C)N1C(=O)CN1CCC(F)(CNC(=O)c2cc(F)cc(Cl)c2)CC1] | 444.1 | 3-chloro-N-[(1-{2-[(3R,5R)-3,5-dimethylmorpholin-4-yl]-2-oxoethyl}-4-fluoropiperidin-4-yl)methyl]-5-fluorobenzamide |
| 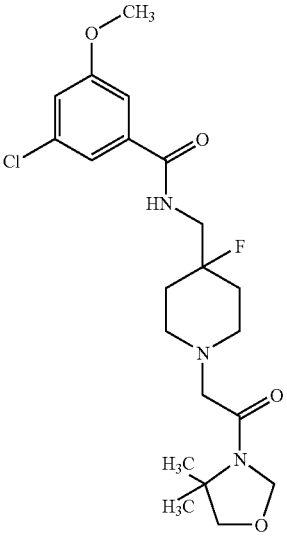 [SMILES: COc1cc(Cl)cc(C(=O)NCC2(F)CCN(CC(=O)N3COCC3(C)C)CC2)c1] | 442.1 | 3-chloro-N-({1-[2-(4,4-dimethyl-1,3-oxazolidin-3-yl)-2-oxoethyl]-4-fluoropiperidin-4-yl}methyl)-5-methoxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH⁺) m/z | NAME |
| --- | --- | --- |
| 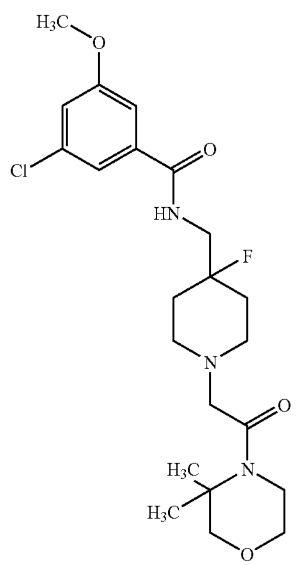 [SMILES: COc1cc(Cl)cc(C(=O)NCC2(F)CCN(CC(=O)N3CCOCC3(C)C)CC2)c1] | 456.2 | 3-chloro-N-({1-[2-(3,3-dimethylmorpholin-4-yl)-2-oxoethyl]-4-fluoropiperidin-4-yl}methyl)-5-methoxybenzamide |
| 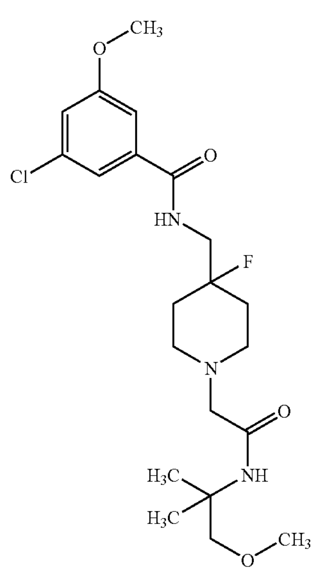 [SMILES: COCC(C)(C)NC(=O)CN1CCC(F)(CNC(=O)c2cc(Cl)cc(OC)c2)CC1] | 444.1 | 3-chloro-N-[(4-fluoro-1-{2-[(2-methoxy-1,1-dimethylethyl)amino]-2-oxoethyl}piperidin-4-yl)methyl]-5-methoxybenzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH$^+$) m/z | NAME |
| --- | --- | --- |
| 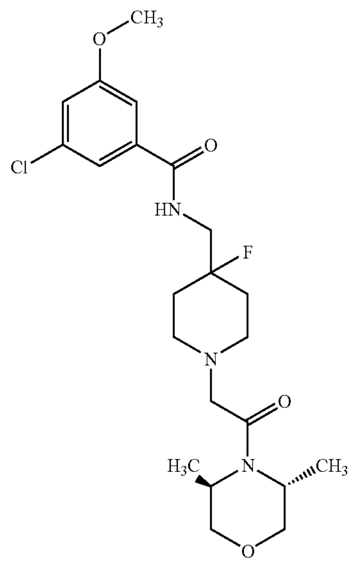 [SMILES: COc1cc(Cl)cc(C(=O)NCC2(F)CCN(CC(=O)N3[C@H](C)COC[C@H]3C)CC2)c1] | 456.1 | 3-chloro-N-[(1-{2-[(3R,5R)-3,5-dimethylmorpholin-4-yl]-2-oxoethyl}-4-fluoropiperidin-4-yl)methyl]-5-methoxybenzamide |
| 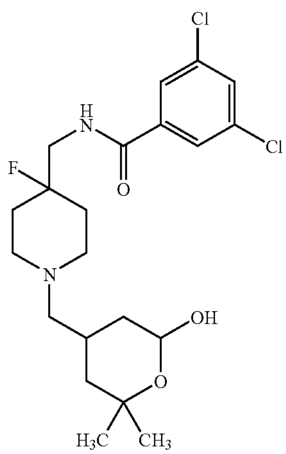 [SMILES: CC1(C)CC(CN2CCC(F)(CNC(=O)c3cc(Cl)cc(Cl)c3)CC2)CC(O)O1] | 447.1 | 3,5-dichloro-N-({4-fluoro-1-[(6-hydroxy-2,2-dimethyltetrahydro-2H-pyran-4-yl)methyl]piperidin-4-yl}methyl)benzamide |
| 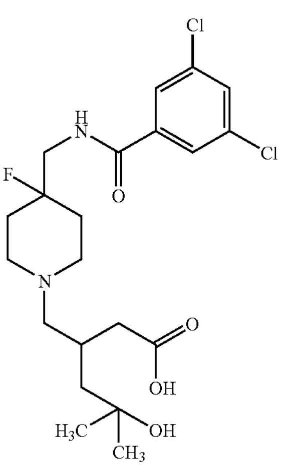 [SMILES: CC(C)(O)CC(CC(=O)O)CN1CCC(F)(CNC(=O)c2cc(Cl)cc(Cl)c2)CC1] | 463.1 | 3-[(4-{[(3,5-dichlorobenzoyl)amino]methyl}-4-fluoropiperidin-1-yl)methyl]-5-hydroxy-5-methylhexanoic acid |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 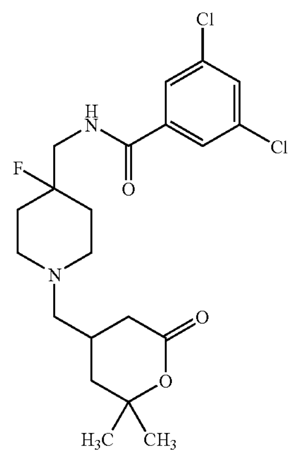 [SMILES: CC1(C)CC(CN2CCC(F)(CNC(=O)c3cc(Cl)cc(Cl)c3)CC2)CC(=O)O1] | 445.0 | 3,5-dichloro-N-({1-[(2,2-dimethyl-6-oxotetrahydro-2H-pyran-4-yl)methyl]-4-fluoropiperidin-4-yl}methyl)benzamide |
| 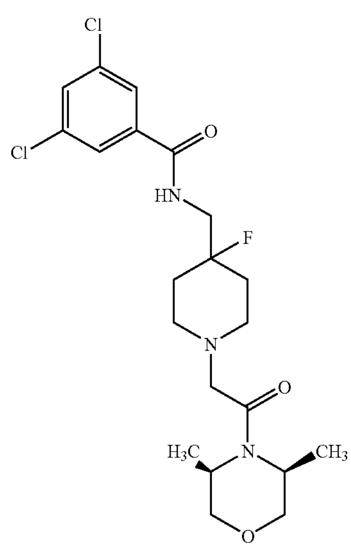 [SMILES: C[C@@H]1COC[C@H](C)N1C(=O)CN1CCC(F)(CNC(=O)c2cc(Cl)cc(Cl)c2)CC1] | 460.1 | 3,5-dichloro-N-[(1-{2-[(3R,5S)-3,5-dimethylmorpholin-4-yl]-2-oxoethyl}-4-fluoropiperidin-4-yl)methyl]benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 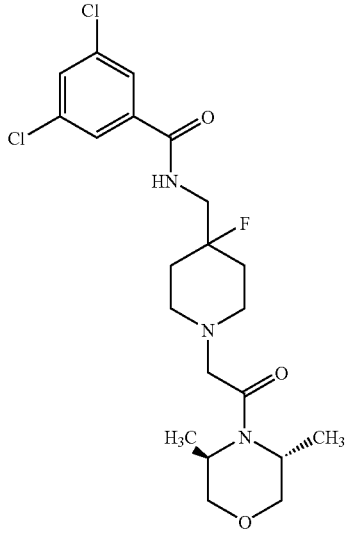 [SMILES: C[C@@H]1COC[C@@H](C)N1C(=O)CN1CCC(F)(CNC(=O)c2cc(Cl)cc(Cl)c2)CC1] | 460.1 | 3,5-dichloro-N-[(1-{2-[(3R,5R)-3,5-dimethylmorpholin-4-yl]-2-oxoethyl}-4-fluoropiperidin-4-yl)methyl]benzamide |
| 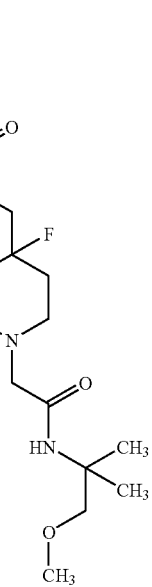 | 448.1 | 3,5-dichloro-N-[(4-fluoro-1-{2-[(2-methoxy-1,1-dimethylethyl)amino]-2-oxoethyl}piperidin-4-yl)methyl]benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 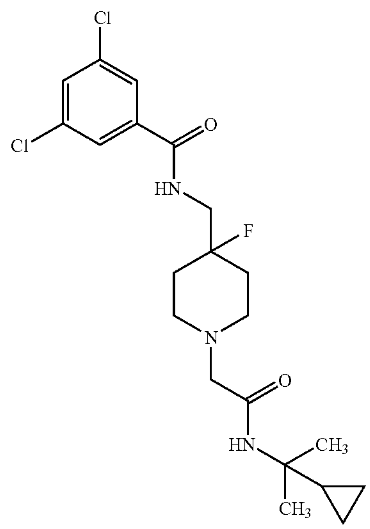 [SMILES: CC(C)(NC(=O)CN1CCC(F)(CNC(=O)c2cc(Cl)cc(Cl)c2)CC1)C1CC1] | 444.1 | 3,5-dichloro-N-[(1-{2-[(1-cyclopropyl-1-methylethyl)amino]-2-oxoethyl}-4-fluoropiperidin-4-yl)methyl]benzamide |
| 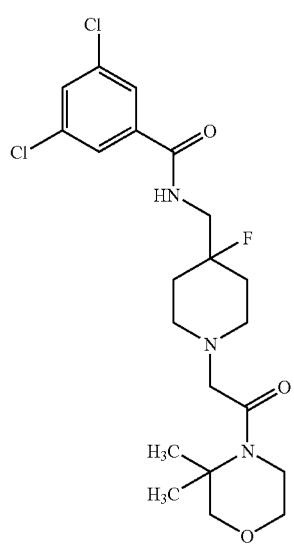 | 460.1 | 3,5-dichloro-N-({1-[2-(3,3-dimethylmorpholin-4-yl)-2-oxoethyl]-4-fluoropiperidin-4-yl}methyl)benzamide |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| STRUCTURE | parent ion (MH+) m/z | NAME |
|---|---|---|
| 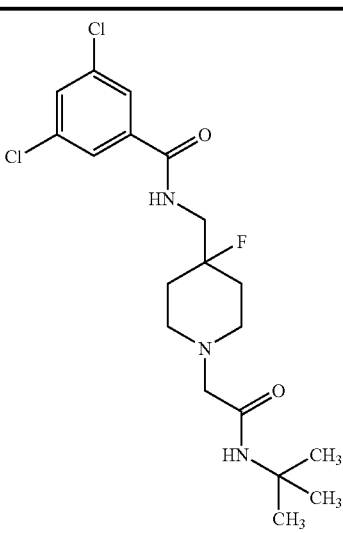 | 418.1 | N-({1-[2-(tert-butylamino)-2-oxoethyl]-4-fluoropiperidin-4-yl}methyl)-3,5-dichlorobenzamide |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound which is selected from the group consisting of:

N-((1-(3,3-dimethylbutyl)-4-fluoropiperidin-4-yl)methyl)-3-fluoro-5-(trifluoromethyl)benzamide;
3,5-dichloro-N-((1-((2,2-dimethyl-tetrahydro-2H-pyran-4-yl)methyl)-4-fluoropiperidin-4-yl)methyl)benzamide;
3-chloro-N-{[1-(3,3-dimethyl-2-oxobutyl)-4-fluoropiperidin-4-yl]methyl}-5-methoxybenzamide;
3-chloro-N-({4-fluoro-1-[(2S)-2-hydroxy-3,3-dimethylbutyl]piperidin-4-yl}methyl)-5-methoxybenzamide;
3-chloro-N-({4-fluoro-1-[(2R)-2-hydroxy-3,3-dimethylbutyl]piperidin-4-yl}methyl)-5-methoxybenzamide;
N-(1-[2-(tert-butylamino)-2-oxoethyl]-4-fluoropiperidin-4-yl}methyl)-3,5-dichlorobenzamide;
3,5-dichloro-N-{[4-fluoro-1-(1H-imidazol-2-ylmethyl)piperidin-4-yl]methyl}benzamide;
N-{[1-3,3-dimethylbutyl)-4-fluoropiperidin-4-yl]methyl}-7,7-dimethyl-2-oxobicyclo[2.2.1]heptane-1-carboxamide;
N-{[1-3,3-dimethylbutyl)-4-fluoropiperidin-4-yl]methyl}-1-(trifluoromethyl)cyclobutanecarboxamide;
3,5-dichloro-N-{[4-fluoro-1-(1H-pyrazol-5-ylmethyl)piperidin-4-yl]methyl}benzamide;
2-benzyl-N-{[1(3,3-dimethylbutyl)-4-fluoropiperidin-4-yl]methyl}-3,3-dimethylbutanamide;
3,5-dichloro-N-[(1-ethyl-4-fluoropiperidin-4-yl)methyl]benzamide;
3,5-dichloro-N-{[4-fluoro-1-(isoxazol-3-ylmethyl)piperidin-4-yl]methyl}benzamide;

3,5-dichloro-N-({4-fluoro-1-[(1-methyl-1H-pyrazol-4-yl)methyl]piperidin-4-yl}methyl)benzamide;
N-{[1-3,3-dimethylbutyl)-4-fluoropiperidin-4-yl]methyl}adamantane-1-carboxamide;
3,5-dichloro-N-{[4-fluoro-1-(tetrahydrofuran-3-ylmethyl)piperidin-4-yl]methyl}benzamide;
(1R,4R)-N-{[1(3,3-dimethylbutyl)-4-fluoropiperidin-4-yl]methyl}-4,7,7-trimethyl-3-oxobicyclo[2.2.1]heptane-2-carboxamide;
3-(dimethylamino)-N-{[1(3,3-dimethylbutyl)-4-fluoropiperidin-4-yl]methyl}benzamide;
3,5-dichloro-N-({1-[(4-chloro-1-methyl-1H-pyrazol-3-yl)methyl]-4-fluoropiperidin-4-yl}methyl)benzamide;
3,5-dichloro-N-({4-fluoro-1-[(5-nitro-2-furyl)methyl]piperidin-4-yl}methyl)benzamide;
3,5-dichloro-N-{[4-fluoro-1-(pentafluorobenzyl)piperidin-4-yl]methyl}benzamide;
3,5-dichloro-N-({4-fluoro-1-[(4-methyl-1H-imidazol-2-yl)methyl]piperidin-4-yl}methyl)benzamide;
3,5-dichloro-N-{[4-fluoro-1-(1,3-thiazol-4-ylmethyl)piperidin-4-yl]methyl}benzamide;
3,5-dichloro-N-({1-[(3-ethyloxetan-3-yl)methyl]-4-fluoropiperidin-4-yl}methyl)benzamide;
3,5-dichloro-N-{[4-fluoro-1-(tetrahydro-2H-pyran-4-ylmethyl)piperidin-4-yl]methyl}benzamide;
3,5-dichloro-N-[(4-fluoro-1-propylpiperidin-4-yl)methyl]benzamide;
3,5-dichloro-N-{[1-(cyclopropylmethyl)-4-fluoropiperidin-4-yl]methyl}benzamide;
1-(2-chloro-4-fluorophenyl)-N-{[1-(3,3-dimethylbutyl)-4-fluoropiperidin-4-yl]methyl}cyclopentane-carboxamide;
3,5-dichloro-N-{[4-fluoro-1-(2-furylmethyl)piperidin-4-yl]methyl}benzamide;
3,5-dichloro-N-({4-fluoro-1-[(1-methyl-1H-pyrazol-3-yl)methyl]piperidin-4-yl}methyl)benzamide;

N-{[1-(3,3-dimethylbutyl)-4-fluoropiperidin-4-yl]methyl}-3-methylbenzamide;
3,5-dichloro-N-[(1-cyclobutyl-4-fluoropiperidin-4-yl)methyl]benzamide;
3,5-dichloro-N-{[4-fluoro-1-(3-furylmethyl)piperidin-4-yl]methyl}benzamide;
N-{[1-(3,3-dimethylbutyl)-4-fluoropiperidin-4-yl]methyl}-3-(trifluoromethyl)-1H-pyrazole-5-carboxamide;
{5-[(4-{[(3,5-dichlorobenzoyl)amino]methyl}-4-fluoropiperidin-1-yl)methyl]-2-furyl}methyl acetate;
N-{[1-(3,3-dimethylbutyl)-4-fluoropiperidin-4-yl]methyl}-3,3-dimethylbutanamide;
3,5-dichloro-N-({1-[(2,5-dimethoxytetrahydrofuran-3-yl)methyl]-4-fluoropiperidin-4-yl}methyl)benzamide;
N-[(1-butyl-4-fluoropiperidin-4-yl)methyl]-3,5-dichlorobenzamide;
3,5-dichloro-N-({1-[(5-chloro-1,3-dimethyl-1H-pyrazol-4-yl)methyl]-4-fluoropiperidin-4-yl}methyl)benzamide;
3,5-dichloro-N-({4-fluoro-1-[(2E,4E)-hexa-2,4-dien-1-yl]piperidin-4-yl}methyl)benzamide;
3,5-dichloro-N-[(4-fluoro-1-isobutylpiperidin-4-yl)methyl]benzamide;
N-{[1-(3,3-dimethylbutyl)-4-fluoropiperidin-4-yl]methyl}-1-(4-fluorophenyl)cyclopentane-carboxamide;
3,5-dichloro-N-{[1-(2,2-dimethylpropyl)-4-fluoropiperidin-4-yl]methyl}benzamide;
3,5-dichloro-N-{[1-(1-cyclobutylethyl)-4-fluoropiperidin-4-yl]methyl}benzamide;
3-[(4-bromo-3,5-dimethyl-1H-pyrazol-1-yl)methyl]-N-{[1-(3,3-dimethylbutyl)-4-fluoropiperidin-4-yl]methyl}benzamide;
N-({1-[(4-bromo-3-thienyl)methyl]-4-fluoropiperidin-4-yl}methyl)-3,5-dichlorobenzamide;
2-[(1S,4R)-bicyclo[2.2.1]hept-2-yl]-N-{[1-(3,3-dimethylbutyl)-4-fluoropiperidin-4-yl]methyl}acetamide;
3-cyano-N-{[1-(3,3-dimethylbutyl)-4-fluoropiperidin-4-yl]methyl}-5-fluorobenzamide;
3,5-dichloro-N-{[4-fluoro-1-(2-thienylmethyl)piperidin-4-yl]methyl}benzamide;
3,5-dichloro-N-({4-fluoro-1-[(2E,4E)-nona-2,4-dien-1-yl]piperidin-4-yl}methyl)benzamide;
3,5-dichloro-N-{[1-(cyclobutylmethyl)-4-fluoropiperidin-4-yl]methyl}benzamide;
N-({1-[(4-bromo-2-thienyl)methyl]-4-fluoropiperidin-4-yl}methyl)-3,5-dichlorobenzamide;
3-chloro-N-({1-[(2,2-dimethyltetrahydro-2H-pyran-4-yl)methyl]-4-fluoropiperidin-4-yl}methyl)-5-fluorobenzamide;
N-{[1-(3,3-dimethylbutyl)-4-fluoropiperidin-4-yl]methyl}-3,5-difluorobenzamide;
N-{[1-(3,3-dimethylbutyl)-4-fluoropiperidin-4-yl]methyl}-1-(3-fluorophenyl)cyclohexane-carboxamide;
3,5-dichloro-N-[(4-fluoro-1-nonylpiperidin-4-yl)methyl]benzamide;
3,5-dichloro-N-({4-fluoro-1-[(5-methyl-2-furyl)methyl]piperidin-4-yl}methyl)benzamide;
3,5-dichloro-N-[(4-fluoro-1-{[5-(methoxymethyl)-2-furyl]methyl}piperidin-4-yl)methyl]benzamide;
3,5-dichloro-N-{[4-fluoro-1-(7-methoxy-3,7-dimethyloctyl)piperidin-4-yl]methyl}benzamide;
3,5-dichloro-N-({1-[(4E)-dec-4-en-1-yl]-4-fluoropiperidin-4-yl}methyl)benzamide;
N-{[1-(3,3-dimethylbutyl)-4-fluoropiperidin-4-yl]methyl}-3-(trifluoromethyl)benzamide;
3,5-dichloro-N-({4-fluoro-1-[(5-methyl-2-thienyl)methyl]piperidin-4-yl}methyl)benzamide;
3,5-dichloro-N-{[4-fluoro-1-(4,4,4-trifluorobutyl)piperidin-4-yl]methyl}benzamide;
3-chloro-N-{[1-(3,3-dimethylbutyl)-4-fluoropiperidin-4-yl]methyl}benzamide;
2-(1-adamantyl)-N-{[1-(3,3-dimethylbutyl)-4-fluoropiperidin-4-yl]methyl}acetamide;
3,5-dichloro-N-({1-[(5-ethyl-2-furyl)methyl]-4-fluoropiperidin-4-yl}methyl)benzamide;
3,5-dichloro-N-({4-fluoro-1-[(2E,6Z)-nona-2,6-dien-1-yl]piperidin-4-yl}methyl)benzamide;
3-bromo-N-{[1-(3,3-dimethylbutyl)-4-fluoropiperidin-4-yl]methyl}benzamide;
3,5-dichloro-N-{[4-fluoro-1-(3-thienylmethyl)piperidin-4-yl]methyl}benzamide;
3,5-dichloro-N-[(4-fluoro-1-pentylpiperidin-4-yl)methyl]benzamide;
3,5-dichloro-N-{[4-fluoro-1-(3-methylbutyl)piperidin-4-yl]methyl}benzamide;
3,5-dichloro-N-{[4-fluoro-1-(3-methoxy-3-methylbutyl)piperidin-4-yl]methyl}benzamide;
N-{[1-(3,3-dimethylbutyl)-4-fluoropiperidin-4-yl]methyl}-3,5-dimethylbenzamide;
3,5-dichloro-N-({1-[(2E)-2-ethylbut-2-en-1-yl]-4-fluoropiperidin-4-yl}methyl)benzamide;
3,5-dichloro-N-({4-fluoro-1-[(2E)-2-methylpent-2-en-1-yl]piperidin-4-yl}methyl)benzamide;
ethyl 2-[(4-{[(3,5-dichlorobenzoyl)amino]methyl}-4-fluoropiperidin-1-yl)methyl]cyclopropanecarboxylate;
3,5-dichloro-N-{[1-(cyclopentylmethyl)-4-fluoropiperidin-4-yl]methyl}benzamide;
N-{[1-(3,3-dimethylbutyl)-4-fluoropiperidin-4-yl]methyl}-3-(1,1,2,2-tetrafluoroethoxy)benzamide;
3,5-dichloro-N-({1-[(2,2-dimethyltetrahydro-2H-pyran-4-yl)methyl]-4-fluoropiperidin-4-yl}methyl)benzamide;
N-{[1-(3,3-dimethylbutyl)-4-fluoropiperidin-4-yl]methyl}-3-(trifluoromethoxy)benzamide;
3,5-dichloro-N-{[1-(cyclohex-3-en-1-ylmethyl)-4-fluoropiperidin-4-yl]methyl}benzamide;
3,5-dichloro-N-({4-fluoro-1-[(2E)-hex-2-en-1-yl]piperidin-4-yl}methyl)benzamide;
3,5-dichloro-N-[(4-fluoro-1-hexylpiperidin-4-yl)methyl]benzamide;
3-chloro-N-{[1-(3,3-dimethylbutyl)-4-fluoropiperidin-4-yl]methyl}-5-methylbenzamide;
3,5-dichloro-N-{[1-(2,6-dimethylhept-5-en-1-yl)-4-fluoropiperidin-4-yl]methyl}benzamide;
3,5-dichloro-N-{[1-(2-ethylhexyl)-4-fluoropiperidin-4-yl]methyl}benzamide;
N-({1-[(2,2-dimethyltetrahydro-2H-pyran-4-yl)methyl]-4-fluoropiperidin-4-yl}methyl)adamantane-1-carboxamide;
3,5-dichloro-N-({1-[(2E)-2,4-dimethylhepta-2,6-dien-1-yl]-4-fluoropiperidin-4-yl}methyl)benzamide;
3-tert-butyl-N-{[1-(3,3-dimethylbutyl)-4-fluoropiperidin-4-yl]methyl}-5-methoxybenzamide;
3,5-dichloro-N-{[1-(cyclohexylmethyl)-4-fluoropiperidin-4-yl]methyl}benzamide;
3-chloro-N-{[1-(3,3-dimethylbutyl)-4-fluoropiperidin-4-yl]methyl}-5-fluorobenzamide;
3,5-dichloro-N-{[4-fluoro-1-(3,5,5-trimethylhexyl)piperidin-4-yl]methyl}benzamide;
3,5-dichloro-N-{[4-fluoro-1-(2-methylpentyl)piperidin-4-yl]methyl}benzamide;
N-{[1-(3,3-dimethylbutyl)-4-fluoropiperidin-4-yl]methyl}-3-fluoro-5-(trifluoromethyl)benzamide;

3,5-dichloro-N-{[1-(3,3-dimethylbutyl)-4-fluoropiperidin-4-yl]methyl}benzamide;
3,5-dichloro-N-({4-fluoro-1-[2-(2,6,6-trimethylcyclohex-1-en-1-yl)ethyl]piperidin-4-yl}methyl)benzamide;
3,5-dibromo-N-{[1-(3,3-dimethylbutyl)-4-fluoropiperidin-4-yl]methyl}benzamide;
N-{[1-(1-adamantylmethyl)-4-fluoropiperidin-4-yl]methyl}-3,5-dichlorobenzamide;
3-chloro-5-fluoro-N-({4-fluoro-1-[2-(2,6,6-trimethylcyclohex-1-en-1-yl)ethyl]piperidin-4-yl}methyl)benzamide;
3-chloro-5-fluoro-N-({4-fluoro-1-[(2,6,6-trimethylcyclohex-1-en-1-yl)methyl]piperidin-4-yl}methyl)benzamide;
N-{[1-(1-adamantylmethyl)-4-fluoropiperidin-4-yl]methyl}-3-chloro-5-fluorobenzamide;
3,5-dichloro-N-{[1-(2,3-dimethylpentyl)-4-fluoropiperidin-4-yl]methyl}benzamide;
3,5-dichloro-N-({4-fluoro-1-[(2,6,6-trimethylcyclohex-1-en-1-yl)methyl]piperidin-4-yl}methyl)benzamide;
N-{[1-(3,3-dimethylbutyl)-4-fluoropiperidin-4-yl]methyl}-3,5-dimethoxybenzamide;
3,5-dichloro-N-[(1-{[(1R,5S)-6,6-dimethylbicyclo [3.1.1]hept-2-en-2-yl]methyl}-4-fluoropiperidin-4-yl)methyl]benzamide;
3-chloro-N-[(1-{[(1R,5S)-6,6-dimethylbicyclo[3.1.1]hept-2-en-2-yl]methyl}-4-fluoropiperidin-4-yl)methyl]-5-fluorobenzamide;
N-({1-[(2,2-dimethyltetrahydro-2H-pyran-4-yl)methyl]-4-fluoropiperidin-4-yl}methyl)-1-(4-methylphenyl)cyclopropanecarboxamide;
1-(4-chlorophenyl)-N-({1-[(2,2-dimethyltetrahydro-2H-pyran-4-yl)methyl]-4-fluoropiperidin-4-yl}methyl)cyclopropanecarboxamide;
1-(2,4-dichlorophenyl)-N-({1-[(2,2-dimethyltetrahydro-2H-pyran-4-yl)methyl]-4-fluoropiperidin-4-yl}methyl)cyclopropanecarboxamide;
1-(4-chlorophenyl)-N-({1-[(2,2-dimethyltetrahydro-2H-pyran-4-yl)methyl]-4-fluoropiperidin-4-yl}methyl)cyclobutanecarboxamide;
N-({1-[(2,2-dimethyltetrahydro-2H-pyran-4-yl)methyl]-4-fluoropiperidin-4-yl}methyl)-1-phenylcyclopentanecarboxamide;
N-({1-[(2,2-dimethyltetrahydro-2H-pyran-4-yl)methyl]-4-fluoropiperidin-4-yl}methyl)-1-(4-methylphenyl)cyclopentanecarboxamide;
N-({1-[(2,2-dimethyltetrahydro-2H-pyran-4-yl)methyl]-4-fluoropiperidin-4-yl}methyl)-1-(3-fluorophenyl)cyclopentanecarboxamide;
1-(4-chlorophenyl)-N-({1-[(2,2-dimethyltetrahydro-2H-pyran-4-yl)methyl]-4-fluoropiperidin-4-yl}methyl)cyclopentanecarboxamide;
1-(2-chloro-6-fluorophenyl)-N-({1-[(2,2-dimethyltetrahydro-2H-pyran-4-yl)methyl]-4-fluoropiperidin-4-yl}methyl)cyclopentanecarboxamide;
N-({1-[(2,2-dimethyltetrahydro-2H-pyran-4-yl)methyl]-4-fluoropiperidin-4-yl}methyl)-1-phenylcyclohexanecarboxamide;
N-({1-[(2,2-dimethyltetrahydro-2H-pyran-4-yl)methyl]-4-fluoropiperidin-4-yl}methyl)-1-(4-methylphenyl)cyclohexanecarboxamide;
N-({1-[(2,2-dimethyltetrahydro-2H-pyran-4-yl)methyl]-4-fluoropiperidin-4-yl}methyl)-1-(4-fluorophenyl)cyclohexanecarboxamide;
1-(4-chlorophenyl)-N-({1-[(2,2-dimethyltetrahydro-2H-pyran-4-yl)methyl]-4-fluoropiperidin-4-yl}methyl)cyclohexanecarboxamide;
1-(2-chloro-4-fluorophenyl)-N-({1-[(2,2-dimethyltetrahydro-2H-pyran-4-yl)methyl]-4-fluoropiperidin-4-yl}methyl)cyclohexanecarboxamide;
1-(2-chloro-6-fluorophenyl)-N-({1-[(2,2-dimethyltetrahydro-2H-pyran-4-yl)methyl]-4-fluoropiperidin-4-yl}methyl)cyclohexanecarboxamide;
N-{[1-(3,3-dimethylbutyl)-4-fluoropiperidin-4-yl]methyl}-1-(4-methylphenyl)cyclopropanecarboxamide;
1-(4-chlorophenyl)-N-{[1-(3,3-dimethylbutyl)-4-fluoropiperidin-4-yl]methyl}cyclopropanecarboxamide;
1-(2,4-dichlorophenyl)-N-{[1-(3,3-dimethylbutyl)-4-fluoropiperidin-4-yl]methyl}cyclopropanecarboxamide;
1-(4-chlorophenyl)-N-{[1-(3,3-dimethylbutyl)-4-fluoropiperidin-4-yl]methyl}cyclobutanecarboxamide;
N-{[1-(3,3-dimethylbutyl)-4-fluoropiperidin-4-yl]methyl}-1-phenylcyclopentanecarboxamide;
N-{[1-(3,3-dimethylbutyl)-4-fluoropiperidin-4-yl]methyl}-1-(4-methylphenyl)cyclopentanecarboxamide;
N-{[1-(3,3-dimethylbutyl)-4-fluoropiperidin-4-yl]methyl}-1-(4-methoxyphenyl)cyclopentane-carboxamide;
N-{[1-(3,3-dimethylbutyl)-4-fluoropiperidin-4-yl]methyl}-1-(2-fluorophenyl)cyclopentanecarboxamide;
N-{[1-(3,3-dimethylbutyl)-4-fluoropiperidin-4-yl]methyl}-1-(3-fluorophenyl)cyclopentanecarboxamide;
1-(4-chlorophenyl)-N-{[1-(3,3-dimethylbutyl)-4-fluoropiperidin-4-yl]methyl}cyclopentanecarboxamide;
trans-1-(4-chlorophenyl)-N-{[1-(3,3-dimethylbutyl)-4-fluoropiperidin-4-yl]methyl}-3-fluorocyclobutane-carboxamide;
1-(2-chloro-6-fluorophenyl)-N-{[1-(3,3-dimethylbutyl)-4-fluoropiperidin-4-yl]methyl}cyclopentane-carboxamide;
N-{[1-(3,3-dimethylbutyl)-4-fluoropiperidin-4-yl]methyl}-1-phenylcyclohexanecarboxamide;
N-{[1-(3,3-dimethylbutyl)-4-fluoropiperidin-4-yl]methyl}-1-(4-methylphenyl)cyclohexanecarboxamide;
N-{[1-(3,3-dimethylbutyl)-4-fluoropiperidin-4-yl]methyl}-1-(4-methoxyphenyl)cyclohexane-carboxamide;
N-{[1-(3,3-dimethylbutyl)-4-fluoropiperidin-4-yl]methyl}-1-(2-fluorophenyl)cyclohexanecarboxamide;
N-{[1-(3,3-dimethylbutyl)-4-fluoropiperidin-4-yl]methyl}-1-(4-fluorophenyl)cyclohexanecarboxamide;
1-(4-chlorophenyl)-N-{[1-(3,3-dimethylbutyl)-4-fluoropiperidin-4-yl]methyl}cyclohexanecarboxamide;
1-(2-chloro-4-fluorophenyl)-N-{[1-(3,3-dimethylbutyl)-4-fluoropiperidin-4-yl]methyl}cyclohexane-carboxamide 1-(2-chloro-6-fluorophenyl)-N-{[1-(3,3-dimethylbutyl)-4-fluoropiperidin-4-yl]methyl}cyclohexane-carboxamide;
N-{[1-(3,3-dimethylbutyl)-4-fluoropiperidin-4-yl]methyl}-3-hydroxy-5-methoxybenzamide;
3,5-dichloro-N-{1-[1-(3,3-dimethylbutyl)-4-fluoropiperidin-4-yl]ethyl}benzamide;
N-{[1-(3,3-dimethylbutyl)-4-fluoropiperidin-4-yl]methyl}-3-(2-fluoroethoxy)-5-methoxybenzamide;
N-{[1-(3,3-dimethylbutyl)-4-fluoropiperidin-4-yl]methyl}-3-(fluoromethoxy)-5-methoxybenzamide;
N-({1-[(2,2-dimethyltetrahydro-2H-pyran-4-yl)methyl]-4-fluoropiperidin-4-yl}methyl)-3,5-dimethoxybenzamide;
N-({1-[(2,2-dimethyltetrahydrofuran-3-yl)methyl]-4-fluoropiperidin-4-yl}methyl)-3,5-dimethoxybenzamide;
3-chloro-N-{[1-(3,3-dimethylbutyl)-4-fluoropiperidin-4-yl]methyl}-4-methoxybenzamide;

4-chloro-N-{[1-(3,3-dimethylbutyl)-4-fluoropiperidin-4-yl]methyl}-2-methoxybenzamide;

3-chloro-N-{[1-(3,3-dimethylbutyl)-4-fluoropiperidin-4-yl]methyl}-5-hydroxybenzamide;

3-chloro-N-({1-[(2,2-dimethyltetrahydro-2H-pyran-4-yl)methyl]-4-fluoropiperidin-4-yl}methyl)-4-methoxybenzamide;

3-chloro-N-({1-[(2,2-dimethyltetrahydro-2H-pyran-4-yl)methyl]-4-fluoropiperidin-4-yl}methyl)-5-hydroxybenzamide;

N-({1-[2-(tert-butylsulfonyl)ethyl]-4-fluoropiperidin-4-yl}methyl)-3,5-dichlorobenzamide;

3,5-dichloro-N-[(4-fluoro-1-{2-oxo-2-[2-(trifluoromethyl)pyrrolidin-1-yl]ethyl}piperidin-4-yl)methyl]benzamide;

3,5-dichloro-N-({1-[2-(4,4-dimethyl-1,3-oxazolidin-3-yl)-2-oxoethyl]-4-fluoropiperidin-4-yl}methyl)benzamide;

N-[(1-{2-[tert-butyl(2-methoxyethyl)amino]-2-oxoethyl}-4-fluoropiperidin-4-yl)methyl]-3,5-dichlorobenzamide;

3-chloro-N-{[1-(3,3-dimethylbutyl)-4-fluoropiperidin-4-yl]methyl}-5-(fluoromethoxy)benzamide;

3-chloro-N-{[1-(3,3-dimethylbutyl)-4-fluoropiperidin-4-yl]methyl}-5-methoxybenzamide;

3-chloro-N-({4-fluoro-1-[(2R)-2-hydroxy-3,3-dimethylbutyl]piperidin-4-yl}methyl)-5-methoxy-benzamide;

3-chloro-N-({4-fluoro-1-[(2S)-2-hydroxy-3,3-dimethylbutyl]piperidin-4-yl}methyl)-5-methoxybenzamide;

3-chloro-N-{[4-fluoro-1-(2-hydroxy-3,3-dimethylbutyl)piperidin-4-yl]methyl}-5-methoxybenzamide;

3-chloro-N-{[1-(3,3-dimethyl-2-oxobutyl)-4-fluoropiperidin-4-yl]methyl}-5-methoxybenzamide;

3,5-dichloro-N-({4-fluoro-1-[(2R)-2-hydroxy-3,3-dimethylbutyl]piperidin-4-yl}methyl)benzamide;

3,5-dichloro-N-({4-fluoro-1-[(2S)-2-hydroxy-3,3-dimethylbutyl]piperidin-4-yl}methyl)benzamide;

3-chloro-N-[(4-fluoro-1-{2-oxo-2-[2-(trifluoromethyl)pyrrolidin-1-yl]ethyl}piperidin-4-yl)methyl]-5-methoxybenzamide;

N-[(4-fluoro-1-{2-oxo-2-[2-(trifluoromethyl)pyrrolidin-1-yl]ethyl}piperidin-4-yl)methyl]-3,5-dimethoxybenzamide;

3-chloro-5-fluoro-N-[(4-fluoro-1-{2-oxo-2-[2-(trifluoromethyl)pyrrolidin-1-yl]ethyl}piperidin-4-yl)methyl]benzamide;

3-chloro-N-[(1-{2-[(1-cyclopropyl-1-methylethyl)amino]-2-oxoethyl}-4-fluoropiperidin-4-yl)methyl]-5-methoxybenzamide;

N-({1-[2-(tert-butylamino)-2-oxoethyl]-4-fluoropiperidin-4-yl}methyl)-3-chloro-5-methoxybenzamide;

3,5-dichloro-N-{[4-fluoro-1-(2-hydroxy-3,3-dimethylbutyl)piperidin-4-yl]methyl}benzamide;

3,5-dichloro-N-({1-[(6,6-dimethyltetrahydro-2H-pyran-2-yl)methyl]-4-fluoropiperidin-4-yl}methyl)-benzamide;

3,5-dichloro-N-{[1-(3,3-dimethyl-2-oxobutyl)-4-fluoropiperidin-4-yl]methyl}benzamide;

N-({1-[2-(tert-butylamino)-2-oxoethyl]-4-fluoropiperidin-4-yl}methyl)-2-(4-tert-butylphenyl)acetamide;

N-({1-[2-(4,4-dimethyl-1,3-oxazolidin-3-yl)-2-oxoethyl]-4-fluoropiperidin-4-yl}methyl)-3,5-dimethoxybenzamide;

N-({1-[2-(3,3-dimethylmorpholin-4-yl)-2-oxoethyl]-4-fluoropiperidin-4-yl}methyl)-3,5-dimethoxy-benzamide;

N-[(4-fluoro-1-{2-[(2-methoxy-1,1-dimethylethyl)amino]-2-oxoethyl}piperidin-4-yl)methyl]-3,5-dimethoxybenzamide;

N-[(1-{2-[(3R,5R)-3,5-dimethylmorpholin-4-yl]-2-oxoethyl}-4-fluoropiperidin-4-yl)methyl]-3,5-dimethoxybenzamide;

3-chloro-N-({1-[2-(4,4-dimethyl-1,3-oxazolidin-3-yl)-2-oxoethyl]-4-fluoropiperidin-4-yl}methyl)-5-fluorobenzamide;

3-chloro-N-({1-[2-(3,3-dimethylmorpholin-4-yl)-2-oxoethyl]-4-fluoropiperidin-4-yl}methyl)-5-fluorobenzamide;

3-chloro-5-fluoro-N-[(4-fluoro-1-{2-[(2-methoxy-1,1-dimethylethyl)amino]-2-oxoethyl}piperidin-4-yl)methyl]benzamide;

3-chloro-N-[(1-{2-[(3R,5R)-3,5-dimethylmorpholin-4-yl]-2-oxoethyl}-4-fluoropiperidin-4-yl)methyl]-5-fluorobenzamide;

3-chloro-N-({1-[2-(4,4-dimethyl-1,3-oxazolidin-3-yl)-2-oxoethyl]-4-fluoropiperidin-4-yl}methyl) -5-methoxybenzamide;

3-chloro-N-({1-[2-(3,3-dimethylmorpholin-4-yl)-2-oxoethyl]-4-fluoropiperidin-4-yl}methyl)-5-methoxybenzamide;

3-chloro-N-[(4-fluoro-1-{2-[(2-methoxy-1,1-dimethylethyl)amino]-2-oxoethyl}piperidin-4-yl)methyl]-5-methoxybenzamide;

3-chloro-N-[(1-{2-[(3R,5R)-3,5-dimethylmorpholin-4-yl]-2-oxoethyl}-4-fluoropiperidin-4-yl)methyl]-5-methoxybenzamide3,5-dichloro-N-({4-fluoro-1-[(6-hydroxy-2,2-dimethyltetrahydro-2H-pyran-4-yl)methyl]piperidin-4-yl}methyl)benzamide;

3-[(4-{[(3,5-dichlorobenzoyl)amino]methyl}-4-fluoropiperidin-1-yl)methyl]-5-hydroxy-5-methylhexanoic acid;

3,5-dichloro-N-({1-[(2,2-dimethyl-6-oxotetrahydro-2H-pyran-4-yl)methyl]-4-fluoropiperidin-4-yl}methyl)benzamide;

3,5-dichloro-N-[(1-{2-[(3R,5S)-3,5-dimethylmorpholin-4-yl]-2-oxoethyl}-4-fluoropiperidin-4-yl)methyl]benzamide;

3,5-dichloro-N-[(1-{2-[(3R,5R)-3,5-dimethylmorpholin-4-yl]-2-oxoethyl}-4-fluoropiperidin-4-yl)methyl]benzamide;

3,5-dichloro-N-[(4-fluoro-1-{2-[(2-methoxy-1,1-dimethylethyl)amino]-2-oxoethyl}piperidin-4-yl)methyl]benzamide;

3,5-dichloro-N-[(1-{2-[(1-cyclopropyl-1-methylethyl)amino]-2-oxoethyl}-4-fluoropiperidin-4-yl)methyl]benzamide;

3,5-dichloro-N-({1-[2-(3,3-dimethylmorpholin-4-yl)-2-oxoethyl]-4-fluoropiperidin-4-yl}methyl)benzamide; and N-({1-[2-(tert-butylamino)-2-oxoethyl]-4-fluoropiperidin-4-yl}methyl)-3,5-dichlorobenzamide;

or a pharmaceutically acceptable salt thereof.

2. A compound which is:

3,5-dichloro-N-((1-((2,2-dimethyl-tetrahydro-2H-pyran-4-yl)methyl)-4-fluoropiperidin-4-yl)methyl)benzamide;

or a pharmaceutically acceptable salt thereof.

3. The compound of claim 2 which is:

(+)-3,5-dichloro-N-((14(2,2-dimethyl-tetrahydro-2H-pyran-4-yl)methyl)-4-fluoropiperidin-4-yl)methyl)benzamide;

or a pharmaceutically acceptable salt thereof.

4. The compound of claim 2 which is:

(−)-3,5-dichloro-N-((1-((2,2-dimethyl-tetrahydro-2H-pyran-4-yl)methyl)-4-fluoropiperidin-4-yl)methyl)benzamide;

or a pharmaceutically acceptable salt thereof.

5. The compound of claim 1 which is:

3,5-dichloro -N-{[1-(3,3-dimethylbutyl)-4-fluoropiperidin-4-yl]methyl}benzamide ;

or a pharmaceutically acceptable salt thereof.

6. A pharmaceutical composition which comprises an inert carrier and a compound of claim 1 or a pharmaceutically acceptable salt thereof.

7. A pharmaceutical composition which comprises an inert carrier and a compound of claim 2 or a pharmaceutically acceptable salt thereof.

8. A pharmaceutical composition which comprises an inert carrier and a compound of claim 3 or a pharmaceutically acceptable salt thereof.

9. A pharmaceutical composition which comprises an inert carrier and a compound of claim 4 or a pharmaceutically acceptable salt thereof.

10. A pharmaceutical composition which comprises an inert carrier and a compound of claim 5 or a pharmaceutically acceptable salt thereof.

\* \* \* \* \*